United States Patent
Stoessel et al.

(10) Patent No.: US 10,374,167 B2
(45) Date of Patent: Aug. 6, 2019

(54) COMPOUND WITH NOVEL SIX-MEMBERED RING STRUCTURE FOR USE IN ORGANIC ELECTRONIC DEVICES

(71) Applicant: Merck Patent GmbH, Darmstadt (DE)

(72) Inventors: Philipp Stoessel, Frankfurt am Main (DE); Amir Hossain Parham, Frankfurt am Main (DE); Christof Pflumm, Darmstadt (DE); Anja Jatsch, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 10 days.

(21) Appl. No.: 15/036,311

(22) PCT Filed: Oct. 20, 2014

(86) PCT No.: PCT/EP2014/002825
§ 371 (c)(1),
(2) Date: May 12, 2016

(87) PCT Pub. No.: WO2015/070944
PCT Pub. Date: May 21, 2015

(65) Prior Publication Data
US 2016/0301016 A1  Oct. 13, 2016

(30) Foreign Application Priority Data
Nov. 15, 2013 (EP) .................................... 13005398

(51) Int. Cl.
*H01L 51/00* (2006.01)
*H01L 51/50* (2006.01)
(Continued)

(52) U.S. Cl.
CPC ........ *H01L 51/0072* (2013.01); *C07D 209/86* (2013.01); *C07D 219/14* (2013.01); C07D 491/107; C07D 307/87; C07D 471/04; C07D 487/04; C07D 219/14; C07D 209/86
See application file for complete search history.

(58) Field of Classification Search
CPC . H01L 51/0073; H01L 51/5012; H01L 51/56; H01L 51/5092; H01L 51/5096; H01L 51/5024; H01L 51/006; H01L 51/005; H01L 51/5076; H01L 51/0058; H01L 51/0072; H01L 51/0052; H01L 51/0061; H01L 51/0071; C09K 2211/1029; C09K 2211/1033; C09K 2211/1044; C09K 2211/1088; C09K 2211/1007; C09K 2211/1011; C09K 2211/1014; C09K 11/06; Y02P 70/521; Y02E 10/549;
(Continued)

(56) References Cited

U.S. PATENT DOCUMENTS

| 2,573,733 A | 11/1951 | Salvin et al. |
| 6,511,971 B1 | 1/2003 | Gorun |

(Continued)

FOREIGN PATENT DOCUMENTS

| JP | 2002527553 | 8/2002 |
| JP | 200651666 A | 7/2006 |

(Continued)

OTHER PUBLICATIONS

Richard J. Lewis, Sr. "Hawley's Condensed Chemical Dictionary, 12th Edition", John Wiley & Sons, Inc., New York p. 937 (1993).*
International Search Report for PCT/EP2014/002825[7] dated Jan. 16, 2015.
Uoyama, H., et al., "Highly efficient organic light-emitting diodes from delayed fluorescence", Nature, vol. 492, No. 7428, (2012), pp. 234-238.
Carpenter et al., "Nitro Musks. II. tert-Amyl Homologs of the Commercial Musks", *Contribution from the Research Laboratories of the Givaudan Corporation*, 4 pages (1950).
European Office Action for EP Patent Application No. 14 789 994.2 dated Jun. 8, 2017.
English Translation of Chinese Office Action for Chinese Application No. 201480061468, dated Feb. 9, 2018.
Volkov, K.A., "Phthalocyanines and Related Compounds: XLVIII. 1 Stepwise Nucleophilic Substitution in Tetrachlorophthalonitrile: Synthesis of Polysubstituted Phthalonitriles", Russian Journal of General Chemistry, 2008, vol. 78, No. 9, pp. 1794-1801.

*Primary Examiner* — Alexander C Kollias
(74) *Attorney, Agent, or Firm* — Drinker Biddle & Reath LLP

(57) ABSTRACT

The present invention relates to novel compounds according to formula (I) having a six-membered ring structure substituted with electron donor, electron acceptor and sterically demanding groups. Said compound is suited for use in organic electronic devices, particularly in organic electroluminescent devices (OLEDs). Formula (I) wherein $Q^1$ and $Q^2$ are independently of each other selected from the group consisting of N, $CR^A$, $CR^D$, and $CR^S$; $Z^1$ and $Z^2$ are independently of each other selected from the group consisting of N, $CR^A$ and $CR^D$; $R^A$ is a group with −M-effect; $R^D$ is a group with +M-effect; and $R^S$ is a sterically demanding group, with the provision that the compound of general formula (I) comprises at least one group $CR^A$ and at least one group $CR^D$.

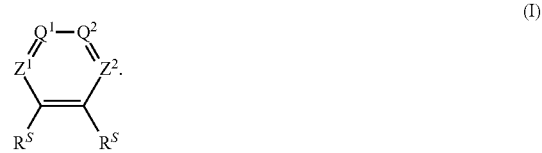

(I)

15 Claims, No Drawings

(51) Int. Cl.
- *C07D 209/86* (2006.01)
- *C07D 219/14* (2006.01)
- *C07D 307/87* (2006.01)
- *C07D 471/04* (2006.01)
- *C07D 487/04* (2006.01)
- *C07D 491/107* (2006.01)
- *C09K 11/06* (2006.01)
- *H01L 51/56* (2006.01)

(52) U.S. Cl.
CPC ......... *C07D 307/87* (2013.01); *C07D 471/04* (2013.01); *C07D 487/04* (2013.01); *C07D 491/107* (2013.01); *C09K 11/06* (2013.01); *H01L 51/005* (2013.01); *H01L 51/006* (2013.01); *H01L 51/0052* (2013.01); *H01L 51/0061* (2013.01); *H01L 51/0071* (2013.01); *H01L 51/5024* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1044* (2013.01); *C09K 2211/1088* (2013.01); *H01L 51/0058* (2013.01); *H01L 51/0073* (2013.01); *H01L 51/5012* (2013.01); *H01L 51/5076* (2013.01); *H01L 51/5092* (2013.01); *H01L 51/5096* (2013.01); *H01L 51/56* (2013.01); *Y02E 10/549* (2013.01); *Y02P 70/521* (2015.11)

(56) References Cited

U.S. PATENT DOCUMENTS

| | | | |
|---|---|---|---|
| 6,653,438 | B1 | 11/2003 | Spreitzer et al. |
| 7,834,136 | B2 | 11/2010 | Parham et al. |
| 7,927,718 | B2 | 4/2011 | Kamatani et al. |
| 8,323,804 | B2 | 12/2012 | Heun et al. |
| 8,343,637 | B2 | 1/2013 | Parham et al. |
| 2009/0302752 | A1* | 12/2009 | Parham ............... C07D 209/80 313/504 |
| 2013/0291930 | A1 | 11/2013 | Braun et al. |
| 2015/0105564 | A1* | 4/2015 | Adachi ............... C07D 209/18 548/440 |
| 2016/0093812 | A1 | 3/2016 | Stoessel et al. |

FOREIGN PATENT DOCUMENTS

| | | |
|---|---|---|
| JP | 2008013474 A | 1/2008 |
| JP | 2008525533 A | 7/2008 |
| JP | 2010516637 A | 5/2010 |
| WO | WO-2012095524 A1 | 7/2012 |
| WO | WO-2013154064 A1 | 10/2013 |
| WO | WO-2014166586 A1 | 10/2014 |

* cited by examiner

COMPOUND WITH NOVEL SIX-MEMBERED RING STRUCTURE FOR USE IN ORGANIC ELECTRONIC DEVICES

CROSS-REFERENCE TO RELATED APPLICATIONS

This application is a national stage application (under 35 U.S.C, § 371) of PCT/EP2014/002825, filed Oct. 20, 2014, which claims benefit of European Application No. 13005398.6, filed Nov. 15, 2013, both applications of which are incorporated herein by reference in their entirety.

TECHNICAL FIELD

The present invention relates to a novel compound having a six-membered ring structure substituted with electron donor, electron acceptor and sterically demanding groups. Said compound is suited for use in organic electronic devices, particularly in organic electroluminescent devices.

BACKGROUND

Organic electronic devices, i.e. electronic devices comprising a layer which is mostly made of an organic material, offer a number of advantages over conventional electronic devices based on inorganic materials. Organic electronic devices allow for example good processability in combination with improved final properties such as flexibility and/or reduced weight. Frequently, such devices are also characterized by extremely low energy consumption. Properties like these are of considerable interest for example for handheld devices, such as tablet-PCs and smart phones.

A particular example of organic electronic devices are organic electroluminescent devices (OLEDs). The term "organic electroluminescent device" is generally used for an electronic device which comprises at least one organic material that emits light when an electric current is applied. OLEDs in general as well as their structure are for example disclosed in U.S. Pat. Nos. 4,539,507, 5,151,629, EP 0676461 and WO 98/27136.

Though progress has been made there remains considerable interest in improving the properties of organic electronic devices, particularly of organic electroluminescent devices, such as for example in terms of life time, efficiency and operating voltage. Important factors in this respect are organic light emitting layers, and particularly the materials comprised therein, as well as organic charge transporting layers.

It is therefore an object of the present invention to find novel materials having improved properties. Additionally, it is an object of the present invention to further increase the pool of available materials suited for use in organic electronic devices in general and organic electroluminescent devices in particular. Furthermore, it is a particular object of the present invention to increase the pool of materials emitting light of blue color. Further objects of the present invention will become evident from the following description as well as from the examples.

SUMMARY

The present inventors have now surprisingly found that the above objects may be attained either individually or in any combination by the present compound as well as by further aspects of the present application.

The present application therefore provides for a compound of general formula (I)

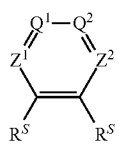

(I)

wherein $Q^1$ and $Q^2$ are independently of each other selected from the group consisting of N, $CR^A$, $CR^D$, and $CR^S$; $Z^1$ and $Z^2$ are independently of each other selected from the group consisting of N, $CR^A$ and $CR^D$; $R^A$ is a group with −M-effect; $R^D$ is a group with +M-effect; and $R^S$ is a sterically demanding group, with the provision that the compound of general formula (I) comprises at least one group $CR^A$ and at least one group $CR^D$.

The present application also provides for a formulation comprising a solvent and said compound.

Further, the present application provides for a method for producing an electronic device, said process comprising the steps of
(a) providing said compound or an oligomer, polymer or dendrimer comprising such compound; and
(b) depositing said compound or said oligomer, polymer or dendrimer on a supporting layer In addition, the present application provides for organic electronic devices, particularly for organic electroluminescent devices, comprising said compound.

DETAILED DESCRIPTION

Definitions

For the purposes of the present application the terms "organic light emitting device" and "organic electroluminescent device" are used interchangeably.

For the purposes of the present application the terms "group" and "substituent" are used synonymously.

For the purposes of the present application the term "substituted" is meant to denote a substituent $R^2$ as defined in the present application.

In the formulae of the present application a double bond may be used to denote an aromatic bond in an aromatic or heteroaromatic ring system.

The mesomeric effect, in the present application denoted as "M-effect", is attributed to a substituent or group due to overlap of its p- or π-orbitals with the p- or π-orbitals of the rest of the molecular entity. Delocalization is thereby introduced or extended, and electronic charge may flow to or from the substituent. See International Union of Pure and Applied Chemistry, Compendium of Chemical Technology, Gold Book, Version 2.3.2, Aug. 19, 2012. Groups with a +M-effect ("positive M-effect") donate electron density to the mesomeric system. Groups with a −M-effect ("negative M-effect") accept electron density from the mesomeric system.

In the present application $R^1$ is at each occurrence independently selected from the group consisting of H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, OH, SH, linear alkyl-, alkoxy- or thioalkyl-group with 1 to 20 C-atoms or a branched or cyclic alkyl-, alkoxy- or thioalkyl-group with 3 to 20 C-atoms or a alkenyl- or alkinyl-group with 2 to 20 C-atoms, wherein these groups may be substituted with one or more of groups $R^2$ and wherein one or more $CH_2$-groups in these groups may be replaced by $—R^2C=CR^2—$, $—C≡C—$, $Si(R^2)_2$, $C=O$, $C=S$, $C=NR^2$, $—C(=O)O—$, $—C(=O)NR^2—$, $NR^2$, $P(=O)(R^2)$, $—O—$, $—S—$, $SO$ or $SO_2$, and wherein one or more H-atoms in these groups may be replaced by D, F, Cl, Br, I, CN or $NO_2$, or an aromatic or heteroaromatic ring system with 5 to 60 aromatic ring atoms, which can be substituted with one or more groups $R^2$, or an aryloxy- or heteroaryloxy-group with 5 to 60 aromatic ring atoms, which can be substituted with one or more groups $R^2$, or an aralkyl- or heteroaralkyl-group with 5 to 60 aromatic ring atoms, which can be substituted with one or more groups $R^2$, wherein two or more groups $R^2$ may be linked with each other and form an aliphatic or aromatic or heteroaromatic ring.

In the present application $R^2$ is at each occurrence independently selected from the group consisting of H, D, F, alkyl having from 1 to 20 C-atoms, aromatic groups having from 1 to 20 aromatic carbon atoms and heteroaromatic groups having from 1 to 20 aromatic ring atoms, wherein the aromatic groups and the heteroaromatic groups may be substituted with an alkyl having from 1 to 20 carbon atoms. For $R^2$ preferred exemplary alkyls having from 1 to 20 C-atoms may be selected from the group consisting of methyl, ethyl, n-propyl, i-propyl, n-butyl, i-butyl, s-butyl, t-butyl, 2-methylbutyl, n-pentyl, s-pentyl, cyclopentyl, neo-pentyl, n-hexyl, cyclohexyl, neo-hexyl, n-heptyl, cycloheptyl, n-octyl, cyclooctyl, and 2-ethylhexyl. For $R^2$ preferred exemplary aromatic groups having from 1 to 20 aromatic carbon atoms and heteroaromatic groups having from 1 to 20 aromatic ring atoms may be selected from the group consisting of benzene, naphthaline, anthracene, benzanthracene, phenanthrene, benzphenanthrene, pyrene, chrysene, perylene, fluoranthene, naphthacene, pentacene, benzpyrene, biphenyl, biphenylene, terphenyl, terphenylene, quaterphenyl, fluorene, spirobifluorene, dihydrophenanthrene, dihydropyrene, tetrahydropyrene, cis-oder trans-indenofluorene, truxene, isotruxene, spirotruxene, spiroisotruxene, furane, benzofurane, isobenzofurane, dibenzofurane, thiophene, benzothiophene, isobenzothiophene, dibenzothiophene, pyrrole, indole, isoindole, carbazole, indolocarbazole, indenocarbazole, pyridine, chinoline, isochinoline, acridine, phenanthridine, benzo-5,6-chinoline, benzo-6,7-chinoline, benzo-7,8-chinoline, phenothiazine, phenoxazine, pyrazole, indazole, imidazole, benzimidazole, naphthimidazole, phenanthrimidazole, pyridimidazole, pyrazinimidazole, chinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzpyrimidine, chinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine, benzothiadiazole as well as their alkyl substituted derivatives, with the alkyl having from 1 to 20 C-atoms.

In the present application $R^3$ is at each occurrence independently selected from the group consisting of F, linear alkyl- or alkoxy-group with 1 to 20 C-atoms, a branched or cyclic alkyl- or alkoxy-group with 3 to 20 C-atoms, each of which may be substituted with one or more of groups $R^2$, wherein one or more non-adjacent $CH_2$-groups may be replaced by $R^2C=CR^2$, $C≡C$, $Si(R^2)_2$, $C=O$, $NR^2$, O, S or $CONR^2$, and wherein one or more H-atom may be replaced with D or F, or an aromatic or heteroaromatic ring system with 5 to 24 aromatic ring atoms, each of which may each be substituted with one or more of groups $R^2$, or an aryloxy- or heteroaryloxy-group with 5 to 24 aromatic ring atoms, which can be substituted with one or more groups $R^2$, or an aralkyl- or heteroaralkyl-group with 5 to 24 aromatic ring atoms, which can be substituted with one or more groups $R^2$, wherein two $R^2$ bound to the same carbon atom may from an aliphatic or aromatic ring system and thus a spiro system; or $R^3$ can form together with a neighboring group $R^1$ or $R^2$ an aliphatic ring system.

For the purposes of the present invention linear, branched or cyclic alkyl-, alkenyl- and alkinyl-groups may preferably be selected from the group consisting of methyl, ethyl, n-propyl, i-propyl, n-butyl, i-butyl, s-butyl, t-butyl, 2-methylbutyl, n-pentyl, s-pentyl, cyclopentyl, neo-pentyl, n-hexyl, cyclohexyl, neo-hexyl, n-heptyl, cycloheptyl, n-octyl, cyclooctyl, 2-ethylhexyl, trifluoromethyl, pentafluoroethyl, 2,2,2-trifluorethyl, ethenyl, propenyl, butenyl, pentenyl, cyclopentenyl, hexenyl, cyclohexenyl, heptenyl, cycloheptenyl, octenyl, cyclooctenyl, ethinyl, propinyl, butinyl, pentinyl, hexinyl, octinyl, and the respective substituted derivatives, wherein they may be substituted with one or more of groups $R^2$ and wherein one or more $CH_2$-groups in these groups may be replaced by $—R^2C=CR^2—$, $—C≡C—$, $Si(R^2)_2$, $C=O$, $C=S$, $C=NR^2$, $—C(=O)O—$, $—C(=O)NR^2—$, $NR^2$, $P(=O)(R^2)$, $—O—$, $—S—$, $SO$ or $SO_2$, and wherein one or more H-atoms in these groups may be replaced by D, F, Cl, Br, I, CN or $NO_2$.

For the purposes of the present invention, linear or branched alkoxy- and thioalkyl-, alkenyl- and alkinyl-groups may preferably be selected from the group consisting of methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluorethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluorethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethinylthio, propinylthio, butinylthio, pentinylthio, hexinylthio, heptinylthio, octinylthio, and the respective substituted derivatives, wherein they may be substituted with one or more of groups $R^2$ and wherein one or more $CH_2$-groups in these groups may be replaced by $—R^2C=CR^2—$, $—C≡C—$, $Si(R^2)_2$, $C=O$, $C=S$, $C=NR^2$, $—C(=O)O—$, $—C(=O)NR^2—$, $NR^2$, $P(=O)(R^2)$, $—O—$, $—S—$, $SO$ or $SO_2$, and wherein one or more H-atoms in these groups may be replaced by D, F, Cl, Br, I, CN or $NO_2$.

For the purposes of the present invention an aromatic ring system preferably has from 6 to 60 aromatic ring atoms, most preferably from 6 to 30 aromatic ring atoms. For the purposes of the present invention a heteroaromatic ring system preferably has from 5 to 60 aromatic ring atoms, most preferably from 5 to 30 aromatic ring atoms, at least one of which is a heteroatom. Suitable heteroatoms may be selected from the group consisting of N, O and S. The terms "aromatic ring system" and "heteroaromatic ring system" as used herein may also denote a system in which several aryl- or heteroaryl-groups are connected by non-aromatic units. Preferably such non-aromatic units comprise at most 10% of the atoms comprised in the aromatic or heteroaromatic ring system, which are different from H and D. Examples of suitable non-aromatic units may be selected from the group consisting of sp$^3$-hybridized atoms with the atom selected from the group consisting of C, Si, N and O, sp$^2$-hybridized C-atom, sp$^2$-hybridized N-atom, and sp-hybridized C-atom. For the purposes of the present application systems such as for example 9,9'-spirobifluorene, 9,9'-diarylfluorene, tri-arylamine, diarylether, stilbene as well as systems, in which two or more aryl groups are connected for example by means of a linear or cyclic alkyl-, alkenyl- or alkinyl-group of a silyl-group, are to be considered as aromatic rings systems. Furthermore for the purposes of the present application systems, in which one or more aryl- or heteroaryl-groups are connected by means of one or more single bonds, such as for example biphenyl, terphenyl or diphenyltriazine, are to be considered as aromatic or heteroaromatic systems.

Examples of suitable aromatic or heteroaromatic ring systems, which may optionally be substituted as defined above and optionally being linked at any position on the aromatic or heteroaromatic ring as defined in the present application, are preferably selected from the group consisting of benzene, naphthaline, anthracene, benzanthracene, phenanthrene, benzphenanthrene, pyrene, chrysene, perylene, fluoranthene, naphthacene, pentacene, benz-pyrene, biphenyl, biphenylene, terphenyl, terphenylene, quaterphenyl, fluorene, spirobifluorene, dihydrophenan-threne, dihydropyrene, tetrahydropyrene, cis-oder trans-in-denofluorene, truxene, isotruxene, spirotruxene, spiroisotruxene, furane, benzofurane, isobenzofurane, dibenzofurane, thiophene, benzothiophene, isobenzothio-phene, dibenzothiophene, pyrrole, indole, isoindole, carba-zole, indolocarbazole, indenocarbazole, pyridine, chinoline, isochinoline, acridine, phenanthridine, benzo-5,6-chinoline, benzo-6,7-chinoline, benzo-7,8-chinoline, phenothiazine, phenoxazine, pyrazole, indazole, imidazole, benzimidazole, naphthimidazole, phenanthrimidazole, pyridimidazole, pyrazinimidazole, chinoxalinimidazole, oxazole, benzox-azole, naphthoxazole, anthroxazole, phenanthroxazole, isoxazole, 1,2-thiazole, 1,3-thiazole, benzothiazole, pyridazine, benzopyridazine, pyrimidine, benzpyrimidine, chinoxaline, 1,5-diazaanthracene, 2,7-diazapyrene, 2,3-di-azapyrene, 1,6-diazapyrene, 1,8-diazapyrene, 4,5-diazapy-rene, 4,5,9,10-tetraazaperylene, pyrazine, phenazine, phe-noxazine, phenothiazine, fluorubin, naphthyridine, azacarbazole, benzocarboline, phenanthroline, 1,2,3-triaz-ole, 1,2,4-triazole, benzotriazole, 1,2,3-oxadiazole, 1,2,4-oxadiazole, 1,2,5-oxadiazole, 1,3,4-oxadiazole, 1,2,3-thiadi-azole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pte-ridine, indolizine, benzothiadiazole and any combination as well as derivatives thereof.

Examples of aryl and heteroaryl groups, said groups optionally being substituted as defined above and optionally being linked at any position on the aromatic or heteroa-romatic ring as defined in the present application, are prefer-ably selected from the group consisting of benzene, naph-thaline, anthracene, phenanthrene, pyrene, dihydropyrene, chrysene, perylene, fluoranthene, benzanthracene, benz-phenanthrene, tetracene, pentacene, benzpyrene, furane, benzofurane, isobenzofurane, dibenzofurane, thiophene, benzothiophene, isobenzothiophene, dibenzothiophene, pyr-role, indole, isoindole, carbazole, pyridine, chinoline, iso-chinoline, acridine, phenanthridine, benzo-5,6-chinoline, benzo-6,7-chinoline, benzo-7,8-chinoline, phenothiazine, phenoxazine, pyrazole, indazole, imidazole, benzimidazole, naphthimidazole, phenanthrimidazole, pyridimidazole, pyrazinimidazole, chinoxalinimidazole, oxazole, benzox-azole, naphthoxazole, anthroxazole, phenanthroxazole, isoxazole, 1,2-thiazole, 1,3-thiazole, benzothiazole, pyridazine, benzopyridazine, pyrimidine, benzpyrimidine, chinoxaline, pyrazine, phenazine, naphthyridine, azacarba-zole, benzocarboline, phenanthroline, 1,2,3-triazole, 1,2,4-triazol, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triaz-ine, 1,2,4-triazine, 1,2,3-triazine, tetrazole, 1,2,4,5-tetrazine, 1,2,3,4-tetrazine, 1,2,3,5-tetrazine, purine, pteridine, indol-izine and benzothiadiazole.

For the purposes of the present application the terms "aryloxy-group" and "heteroaryloxy-group" are used to denote aryl- and heteroaryl-groups, respectively, as defined above, which are covalently bound via a divalent (ether-type) O-atom.

For the purposes of the present application, the terms "aralkyl-group" and "heteroaralkyl-group" are used to denote aryl- and heteroaryl-groups, respectively, wherein the aryl- or heteroaryl-group is substituted with an alkyl-group having from 1 to 20 C-atoms, wherein in the alkyl-group any H- or D-atom or any $CH_2$-group may be substi-tuted with the above mentioned groups, and wherein the alkyl-group is used to bond the aryl- or heteroaryl-group to the remainder of the compound.

Compound

Stated in a general way, the compounds of the present invention are characterized by a six-membered ring struc-ture, which is substituted with electron donor, electron acceptor and sterically demanding groups as defined herein.

Similar compounds have recently been disclosed by H. Uoyama et al., Nature, Vol. 492, 13 Dec. 2012, pages 234-238.

The compound of the present invention can be repre-sented by the following general formula (I)

(I)

wherein groups $Q^1$, $Q^2$, $Z^1$, $Z^2$ and $R^S$ are as defined below with the provision that the compound of formula (I) com-prises at least one group $CR^A$ and at least one group $CR^D$ as defined below.

Groups $Q^1$ and $Q^2$ are independently of each other selected from the group consisting of N, $CR^A$, $CR^D$ and $CR^S$. More preferably they are independently of each other selected from the group consisting of N, $CR^A$, and $CR^D$. Most preferably they are independently of each other $CR^A$ or $CR^D$.

Groups $Z^1$ and $Z^2$ are independently of each other selected from the group consisting of N, $CR^A$ and $CR^D$. Most preferably, they are independently of each other $CR^A$ or $CR^D$.

Group $R^A$ is a group with a −M-effect. Group $R^D$ is a group with a +M-effect. Such groups are well known to the skilled person and can be found in any common textbook on organic chemistry. The groups $R^A$ are at each occurrence—if more than one such group is present—chosen independently of each other. Also, the groups $R^D$ are at each occurrence—if more than one such group is present—chosen independently of each other.

Examples of compounds of formula (I) are illustrated by the following formulae (I-a) to (I-h)

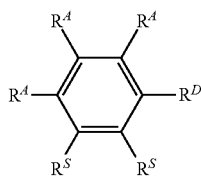
(I-a)

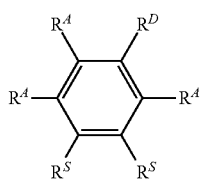
(I-b)

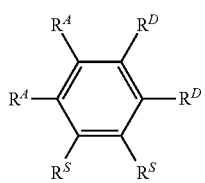
(I-c)

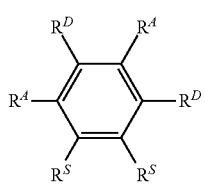
(I-d)

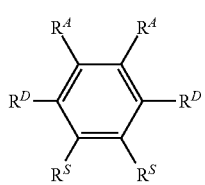
(I-e)

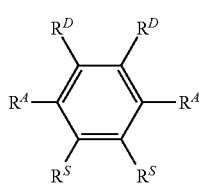
(I-f)

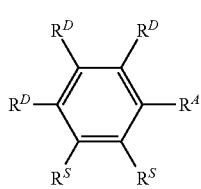
(I-g)

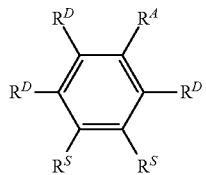
(I-h)

with $R^A$, $R^D$ and $R^S$ as defined herein. Formula (I-e) is particularly well suited.

Preferably the compound of formula (I) comprises at least two groups $R^A$ as defined herein. More preferably the compound of formula (I) comprises at least two identical groups $R^A$. Most preferably the compound of formula (I) comprises two identical groups $R^A$.

Preferably the compound of formula (I) comprises at least two groups $R^D$ as defined herein. More preferably the compound of formula (I) comprises at least two identical groups $R^D$. Most preferably the compound of formula (I) comprises two identical groups $R^D$.

Group $R^A$

Preferred examples of groups $R^A$ may be selected from the group consisting of fluoroalkyl, F, $BR^1_2$, $B(OR^1)_2$, CHO, $C(=O)R^1$, CN, $C(=O)OR^1$, $C(=O)N(R^1)_2$, $CR^1=C(CN)_2$, $N_3$, $NO_2$, $P(=O)(R^1)_2$, $S(=O)R^1$, $S(=O)_2R^1$, heteroaryl, heteroaryl substituted with one or more electron withdrawing groups and aryl substituted with one or more electron withdrawing groups, wherein the electron withdrawing groups are selected from the group consisting of fluoroalkyl, F, $B(OR^1)_2$, CHO, $C(=O)R^1$, CN, $C(=O)OR^1$, $C(=O)N(R^1)_2$, $NO_2$, $P(=O)(R^1)_2$, $S(=O)R^1$, and $S(=O)_2R^1$, with $R^1$ as defined above.

More preferably, at each occurrence $R^A$ is independently selected from the group consisting of fluoroalkyl, F, $C(=O)R^1$, CN, heteroaryl, heteroaryl substituted with one or more electron withdrawing groups and aryl substituted with one or more electron withdrawing groups, wherein the electron withdrawing groups are selected from the group consisting of fluoroalkyl, F, $C(=O)R^1$, and CN, with $R^1$ as defined above.

Even more preferably at each occurrence $R^A$ is independently selected from the group consisting of fluoroalkyl, F, CN, heteroaryl, heteroaryl substituted with one or more electron withdrawing groups and aryl substituted with one or more electron withdrawing groups, wherein the electron withdrawing groups are selected from the group consisting of fluoroalkyl, F, CN.

Still even more preferably at each occurrence $R^A$ is independently selected from the group consisting of F and CN.

Most preferably $R^A$ is CN.

Group $R^D$

Preferred examples of groups $R^D$ may be selected from the group consisting of groups of general formula (N-a)

(N-a)

wherein m is 0 or 1, $Ar^1$ is a substituted or unsubstituted aromatic or heteroaromatic ring system with 5 to 30 aromatic ring atoms, and $R^1$ is as defined above. If m is 0 then no group $Ar^1$ is present in the group of formula (N-a).

Other preferred examples of group $R^D$ may be selected from the group consisting of groups of general formula (N-b)

(N-b)

wherein m and Ar¹ are as defined above, and Ar² is a substituted or unsubstituted aromatic or heteroaromatic ring system with 5 to 30 aromatic carbon atoms, wherein the two groups Ar² may be linked by a group Y, so that together with the N-atom of the NAr²₂-group a ring is formed.

Suitable linking groups Y may for example be selected from the group consisting of a single bond, BR¹, C(R¹)₂, Si(R¹)₂, NR¹, PR¹, P(=O)R¹, P(=S)R¹, O, S, S=O and S(=O)₂.

Preferably said linking group Y may be selected from the group consisting of a single bond, BR¹, C(R¹)₂, Si(R¹)₂, NR¹, P(=O)R¹, O, S, and S(=O)₂.

More preferably said linking group Y may be selected from the group consisting of a single bond, BR¹, C(R¹)₂, NR¹, P(=O)R¹, O, and S(=O)₂.

Even more preferably said linking group Y may be selected from the group consisting of a single bond, C(R¹)₂, NR¹, and O, or alternatively from the group consisting of a single bond, NR¹, and O.

Still even more preferably said linking group Y may be selected from the group consisting of a single bond, and O.

Most preferably said linking group Y is a single bond.

R¹ and R² are as defined above.

At each occurrence said linking group Y may be the same or different. Preferably it is the same at each occurrence.

Particularly suited are groups of formula (N-b), wherein group —NAr²₂ is selected from the group consisting of aromatic amines, heteroaromatic amines, carbazoles, azacarbazoles, annealed carbazoles, annealed azacarbazoles, 5,10-dihydro-phenazaboranes, 9,10-dihydroacridines, 9,10-dihydro-10-sila-acridines, 9,10-dihydro-phenazine, 10-hydro-phenoxazine, and 10-hydro-phentiazine, all of which may be substituted or unsubstituted.

Examples of suitable aromatic amines are illustrated by the following formulae (N-1) to (N-6)

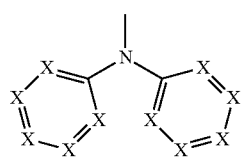
(N-1)

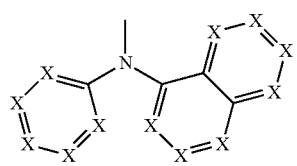
(N-2)

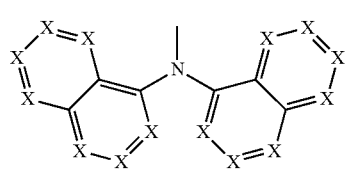
(N-3)

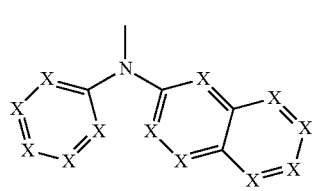
(N-4)

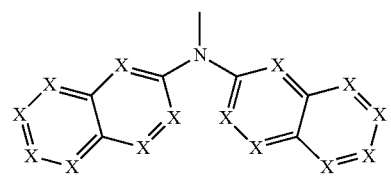
(N-5)

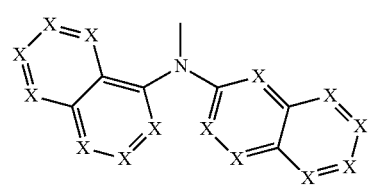
(N-6)

Suitable examples of carbazoles and azacarbazoles and respective annealed derivatives are illustrated by the following formulae (N-7) to (N-17):

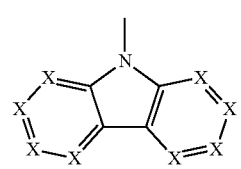
(N-7)

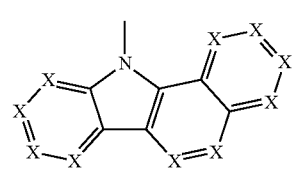
(N-8)

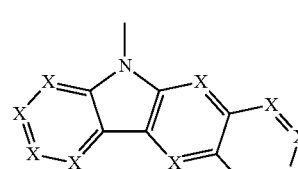
(N-9)

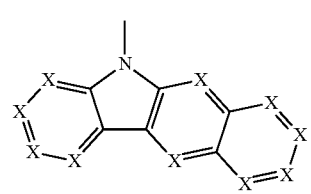
(N-10)

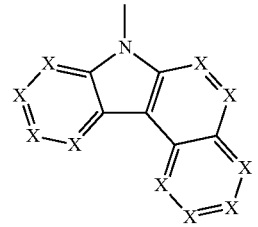
(N-11)

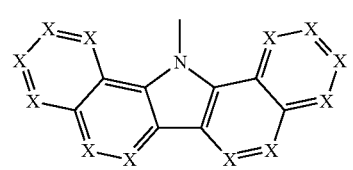
(N-12)

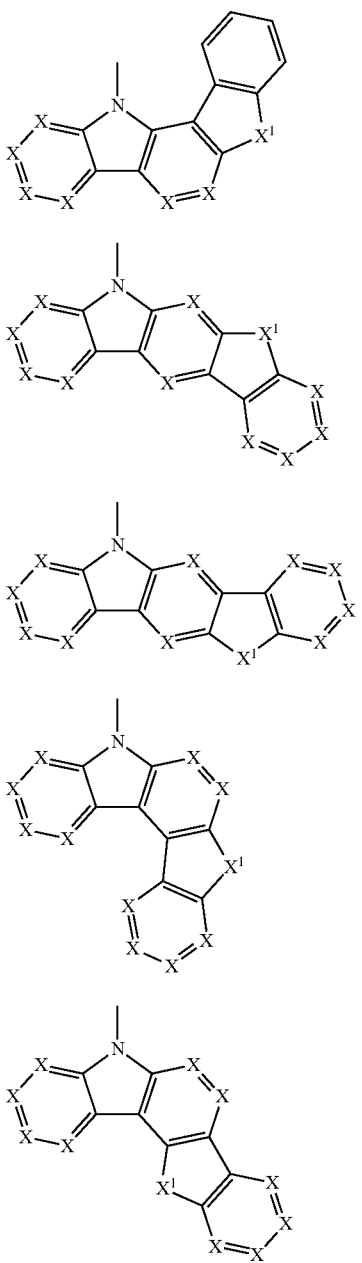

Suitable examples of 5,10-dihydro-phenazaboranes, 9,10-dihydroacridines, 9,10-dihydro-10-sila-acridines, 9,10-dihydro-phenazine, 10-hydro-phenoxazine, and 10-hydro-phentiazine are illustrated by the following formulae (N-18) to (N-23):

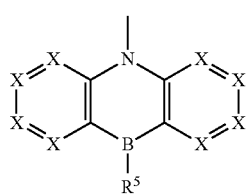
(N-18)

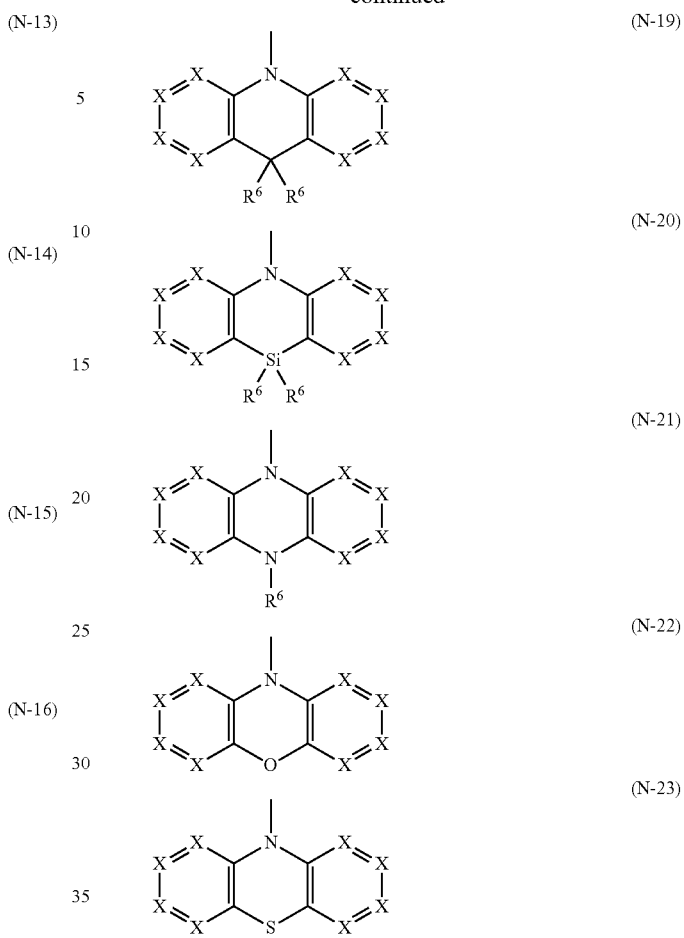

In above formulae (N-1) to (N-23)

X is N or CR⁴ with R⁴ being as defined above for R²;

X¹ is BR², CR¹₂, NR², O or S; preferably CR¹₂, NR², O or S; most preferably CR¹₂ or NR², with R² as defined above;

R⁵ is unsubstituted aryl, unsubstituted hetaryl, substituted aryl or substituted hetaryl, which—if substituted—are preferably substituted in the 2- and 6-positions with alkyl, aryl or CN; and R⁶ is alkyl, unsubstituted aryl, unsubstituted hetaryl, substituted aryl or substituted hetaryl, which optionally may be linked by a group Y as defined above.

Group Rˢ

Group Rˢ is a sterically demanding group. In the present application the term "sterically demanding" is used to denote a group requiring a substantial spatial volume and essentially blocking physical access from the side of the molecule where such groups Rˢ are located.

Suitable groups Rˢ may independently be selected from the group consisting of sec-alkyl, tert-alkyl, sec-fluoroalkyl and tert-fluoroalkyl, or two adjacent groups C—Rˢ together form a five-, six- or seven-membered ring.

Particular examples of Rˢ are isopropyl and tert-butyl.

Examples wherein two adjacent groups C—Rˢ together form a five-, six- or seven-membered ring are illustrated by the following formulae (II-A) to (II-G)

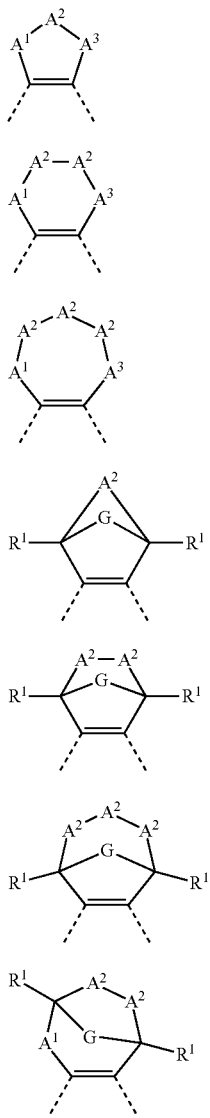

(II-A)

(II-B)

(II-C)

(II-D)

(II-E)

(II-F)

(II-G)

wherein $A^1$, $A^2$, $A^3$, G and $R^1$ are as defined above or below. Formulae (II-A), (II-B), (II-D) and (II-E) are preferred. Formulae (II-A) and (II-B) are most preferred.

It is noted that the five-, six- or seven-membered rings of formulae (II-A) to (II-G) are annealed to the six-membered ring structure of formula (I) such that the dashed lines in formulae (II-A) to (II-G) indicate the bonding to the six-membered ring structure of formula (I).

Group G is selected from the group consisting of substituted or unsubstituted alkanediyl with 1, 2 or 3 C-atoms, —$CR^2$=$CR^2$— or a substituted or unsubstituted ortho-linked arylene- or heteroarylene-group with 5 to 14 aromatic ring atoms, which may be substituted with one or more of groups $R^2$, with $R^2$ as defined above.

Groups $A^1$ and $A^3$ are at each occurrence independently selected from the group consisting of $C(R^3)_2$, O, S, $NR^3$ and $C(=O)$, with $R^3$ as defined above.

Group $A^2$ is at each occurrence independently selected from the group consisting of $C(R^1)_2$, O, S, $NR^1$ and $C(=O)$, with $R^1$ as defined above, and in case two groups $A^2$ are adjacent to each other, $A^2$-$A^2$ may also be selected from the group consisting of ortho-linked arylene- or heteroarylene-group with 5 to 14 aromatic ring atoms, each of which may independently of the other be substituted with $R^2$ as defined above.

Groups $A^1$, $A^2$ and $A^3$ may at each occurrence be independently selected from the respective groups as defined above provided that no two groups selected from O, S and $NR^x$ with $R^x$ being $R^1$ in case of $A^2$ and $R^3$ in case of $A^1$ and $A^3$ are adjacent to each other.

Preferred examples of formula (II-A) may be selected from the following formulae (II-A-a) to (II-A-e)

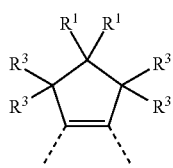
(II-A-a)

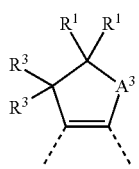
(II-A-b)

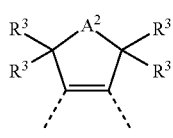
(II-A-c)

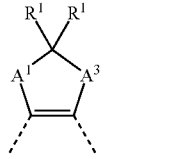
(II-A-d)

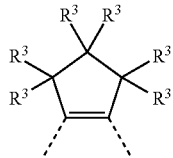
(II-A-e)

with $R^1$ and $R^3$ as defined above, and $A^1$, $A^2$ and $A^3$ are independently of each other selected from the group consisting of O and $NR^3$.

Preferred examples of formula (II-B) may be selected from the following formulae (II-B-a) to (II-B-f)

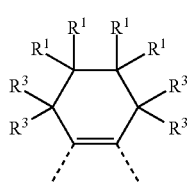
(II-B-a)

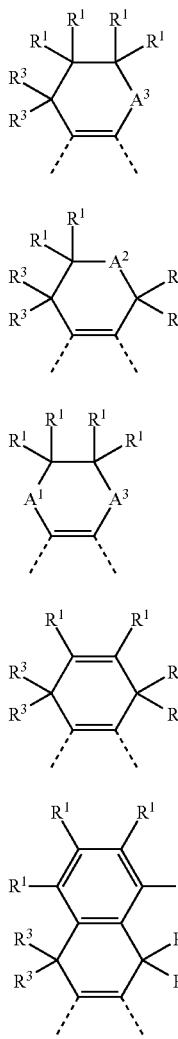

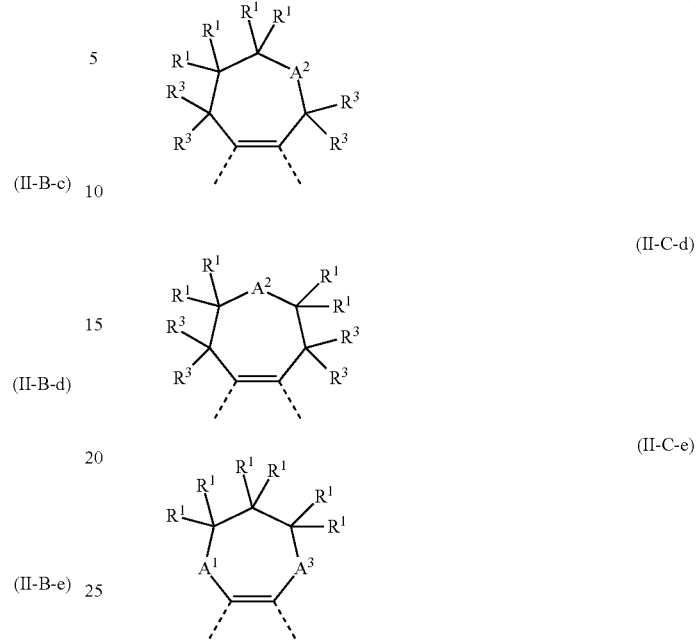

with R¹ and R³ as defined above, and A¹, A² and A³ are independently of each other selected from the group consisting of O and NR³.

Preferred examples of formula (II-C) may be selected from the following formulae (II-C-a) to (II-C-e)

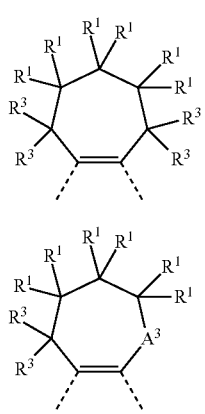

with R¹ and R³ as defined above, and A¹, A² and A³ are independently of each other selected from the group consisting of O and NR³.

Preferred examples of formula (II-D) are those, wherein R¹ is selected from the group consisting of H, D, F and CH₃. Furthermore, A² is preferably C(R¹)₂ or O and most preferably C(R¹)₂. Preferred examples of formula (II-D) may be selected from the following formulae (II-D-a) to (II-D-c)

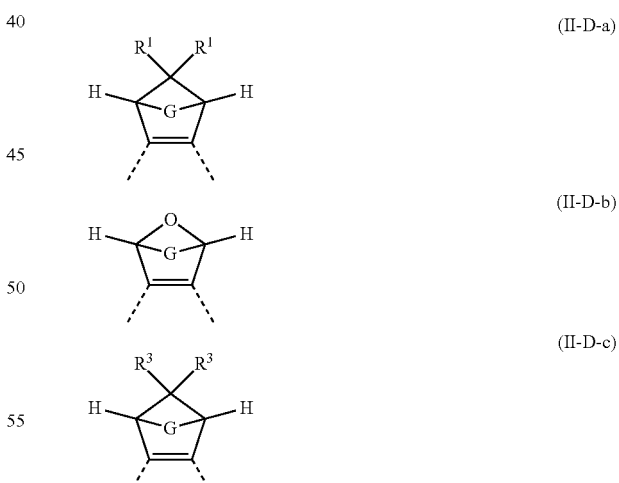

with R¹, R³ and G as defined above.

Preferred examples of formulae (II-E), (II-F) and (II-G) are those, wherein R¹ is selected from the group consisting of H, D, F and CH₃. Preferred A² is C(R¹)₂. Thus, particularly preferred examples of formulae (II-E), (II-F) and (II-G) may be selected from the following formulae (II-E-a), (II-F-a) and (II-G-a)

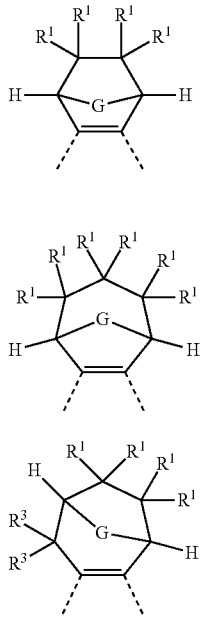

(II-E-a)

(II-F-a)

(II-G-a)

wherein $R^1$, $R^3$ and G are as defined above.

Furthermore, it is preferred that G in formulae (II-C), (II-D), (II-F), (II-G), (II-D-a), (II-D-b), (II-D-c), (II-E-a), (II-F-a) and (II-G-a) is an ethanediyl of formula —$C(R^7)_2$—$C(R^7)_2$—, wherein $R^7$ may at each occurrence be independently selected from the group consisting of H, alkyl having from 1 to 4 C-atoms, and ortho-arylene having from 6 to 10 C-atoms, said ortho-arylene may be substituted with alkyl having from 1 to 4 C-atoms or phenyl. It is, however, preferred that $R^7$ is H.

With regards to formulae (II-A) to (II-G) and their respective examples $R^3$ is preferably at each occurrence independently selected from the group consisting of F, linear alkyl having from 1 to 10 C-atoms, branched or cyclic alkyl having from 3 to 20 C-atoms, and aromatic and heteroaromatic ring systems having from 5 to 14 aromatic ring atoms, wherein two groups $R^3$ on the same C-atom may form an aliphatic or aromatic ring system, thus forming a spirosystem and wherein two groups $R^3$ on adjacent C-atoms may form an aliphatic ring system. In each of these groups one or more H-atom may be replaced by one selected from the group consisting of D, F and alkyl having from 1 to 10 C-atoms.

With regards to formulae (II-A) to (II-G) and their respective examples $R^3$ is most preferably at each occurrence independently selected from the group consisting of F, linear alkyl having from 1 to 3 C-atoms, with methyl being preferred, and aromatic or heteroaromatic ring systems having from 5 to 12 ring atoms, wherein two groups $R^3$ on the same C-atom may form an aliphatic or aromatic ring system, thus forming a spirosystem and wherein two groups $R^3$ on adjacent C-atoms may form an aliphatic ring system. In each of these groups one or more H-atom may be replaced by one selected from the group consisting of D, F and alkyl having from 1 to 10 C-atoms Particularly preferred examples of formula (II-A) may be selected from the following groups:

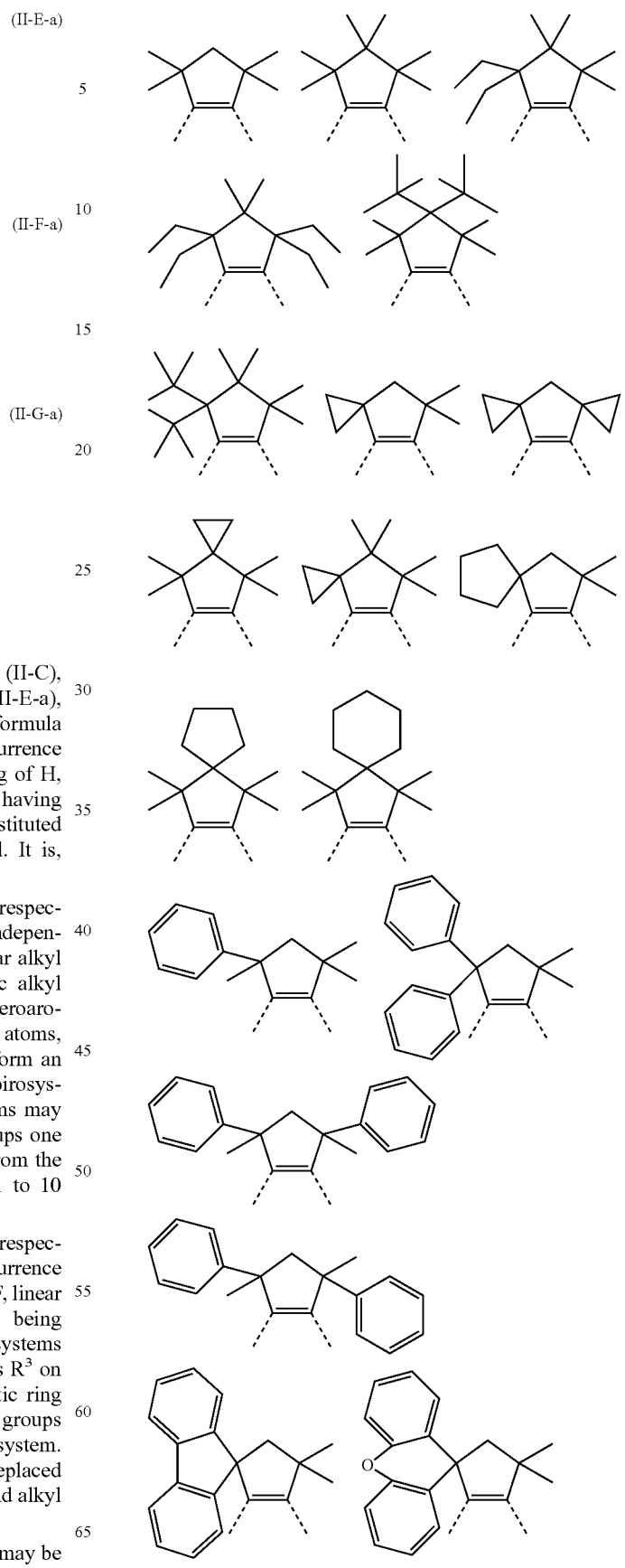

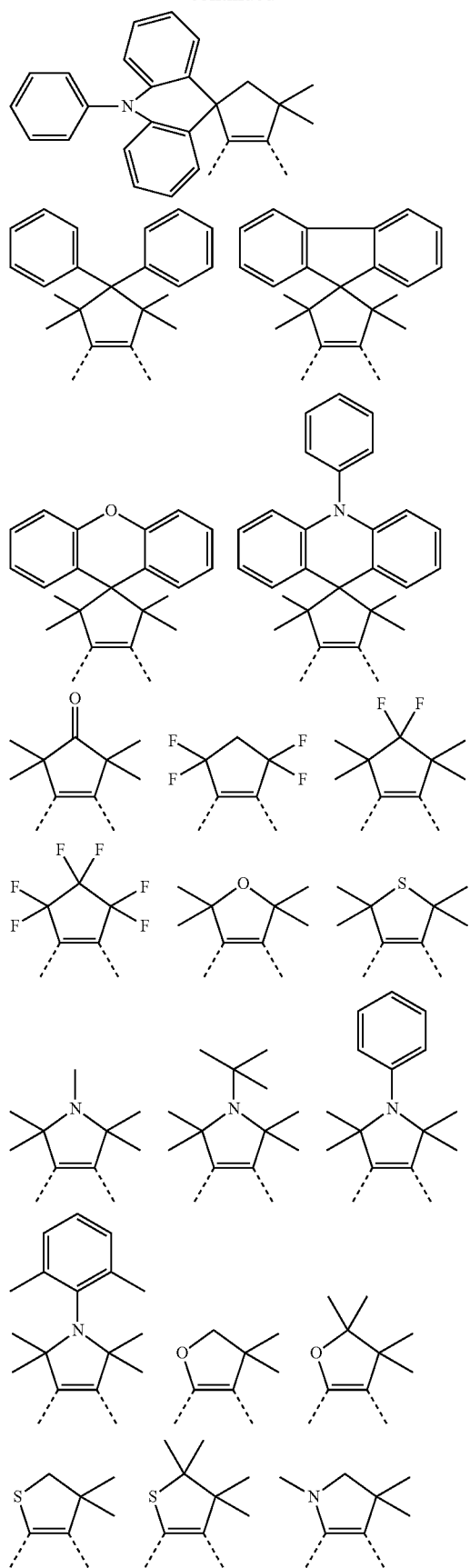
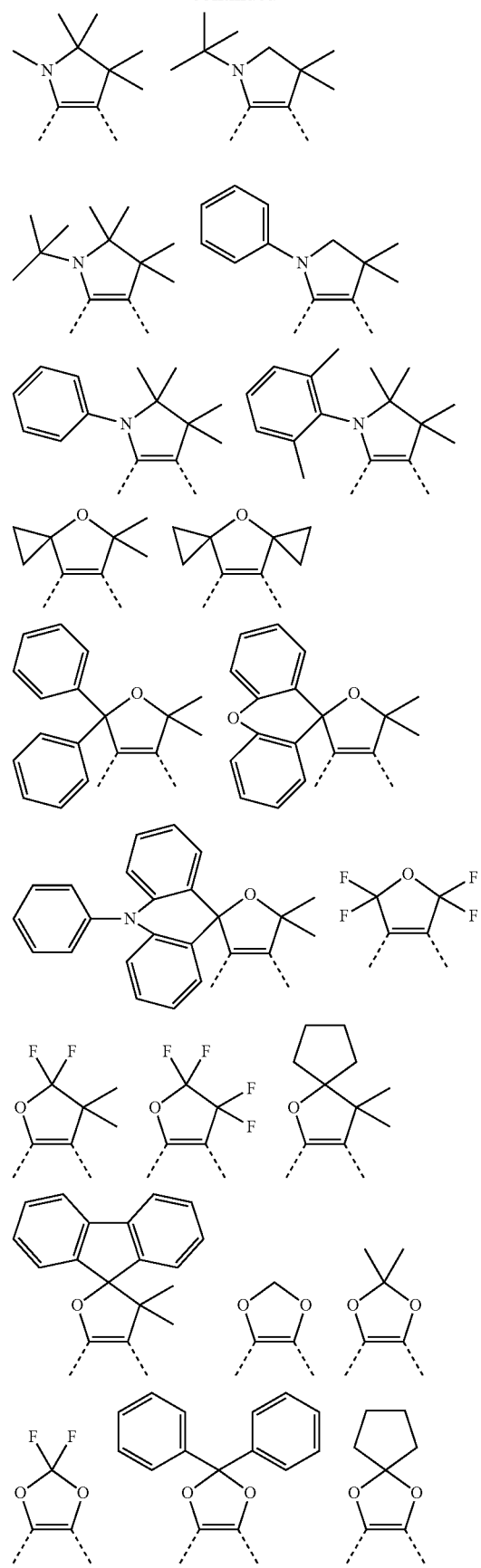

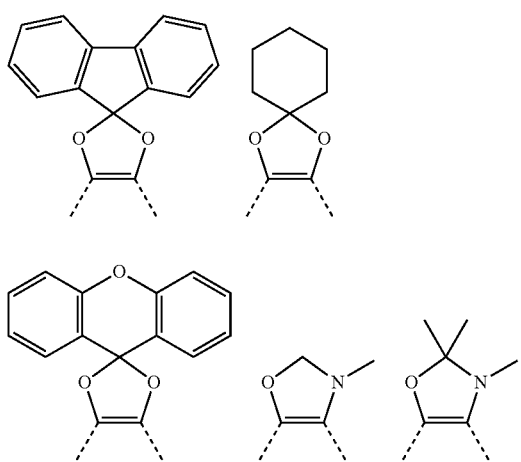
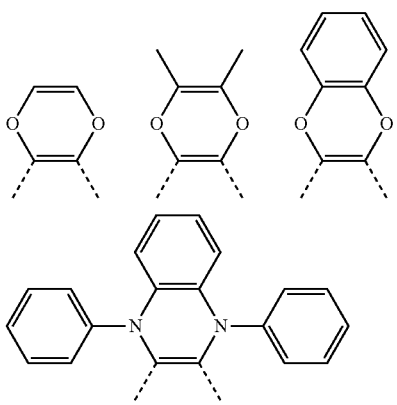
Particularly preferred examples of formula (II-C), (II-F) and (II-G) may be selected from the following groups:
Particularly preferred examples of formula (II-B) may be selected from the following groups:
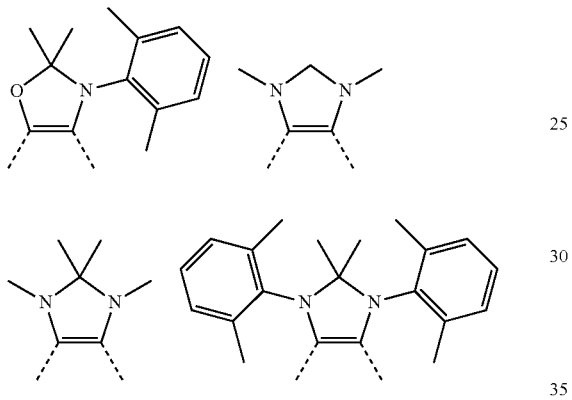
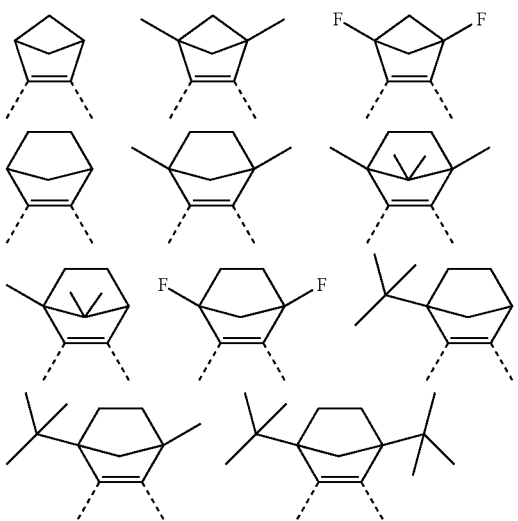
Particularly preferred examples of formula (II-D) may be selected from the following groups:
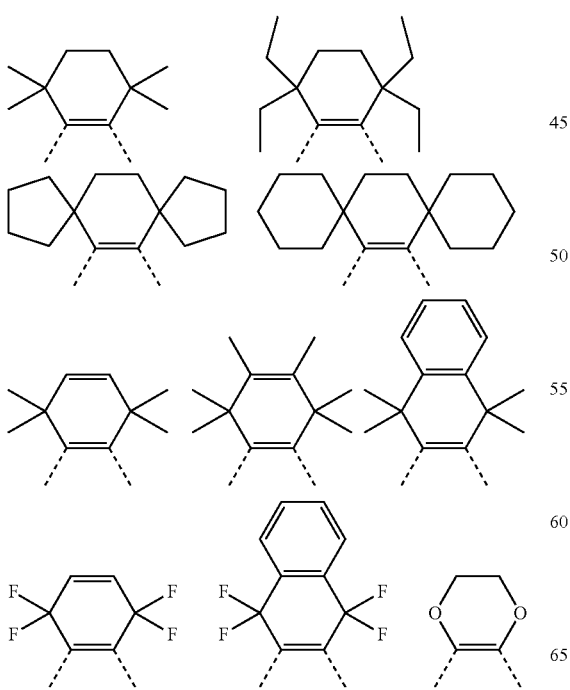

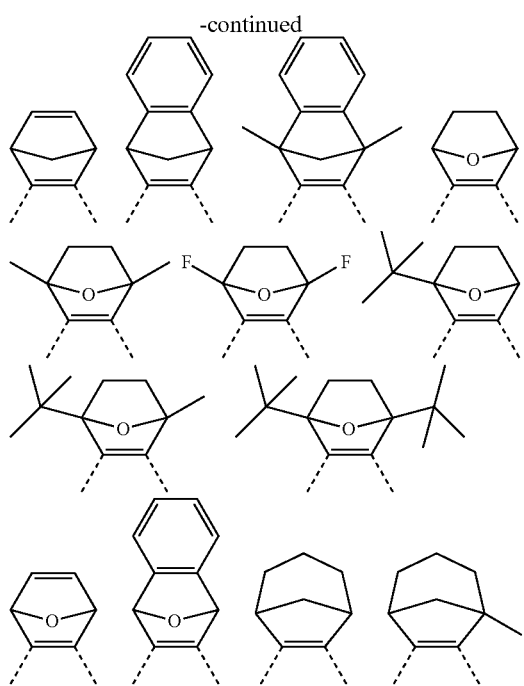

Particularly preferred examples of formula (II-E) may be selected from the following groups:

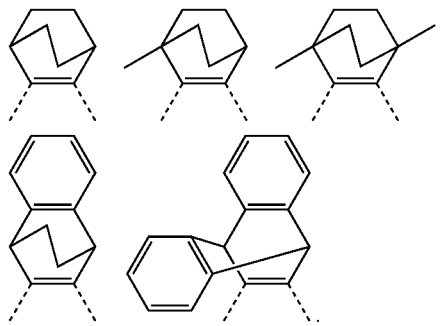

Particularly the use of such annealed bicyclic structures can lead to chiral groups. For reasons of solubility it may be preferred to use of blend of enantiomers, rather than the pure isomers.

Particularly suitable examples of compounds of general formula (I) are illustrated by the following formulae (I-1) to (I-314)

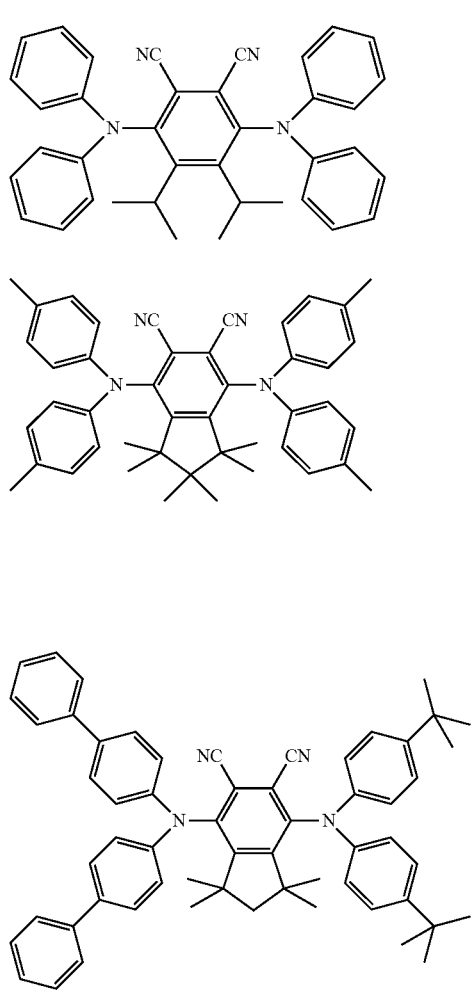

-continued
(I-7)
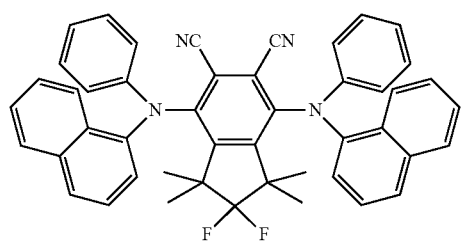
(I-8)
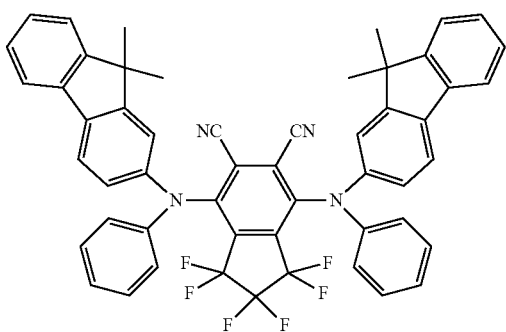
(I-9)
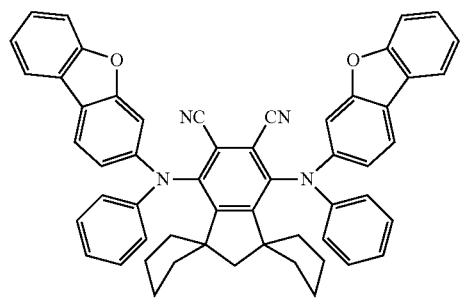
(I-10)
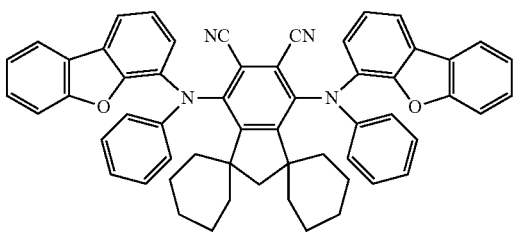
(I-11)
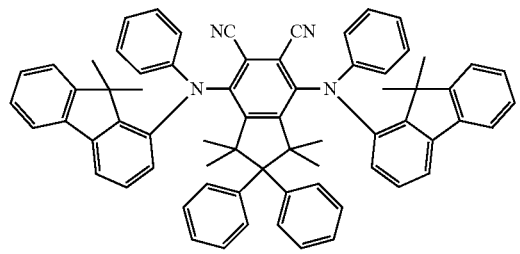
(I-12)
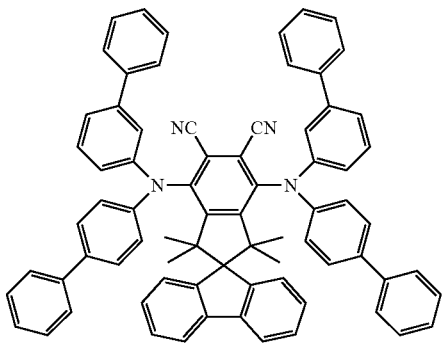
(I-13)
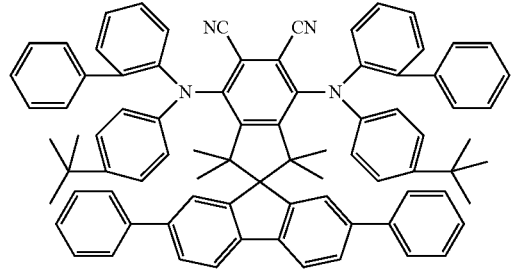
(I-14)
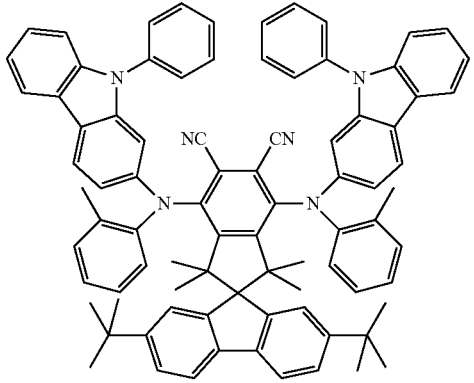

-continued
(I-15)
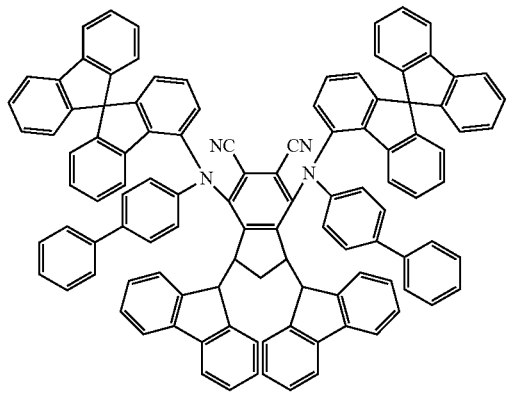
(I-16)
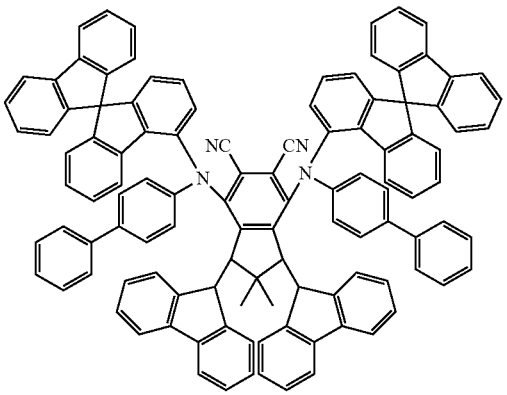
(I-17)
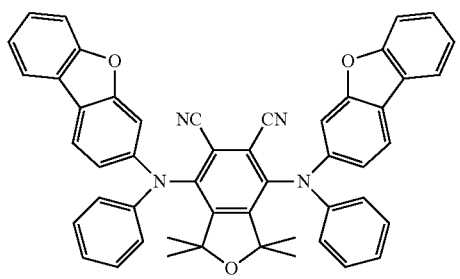
(I-18)
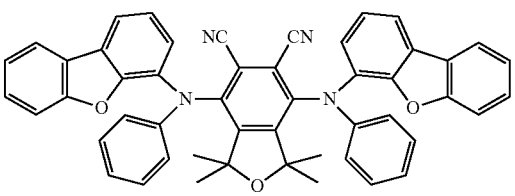
(I-19)
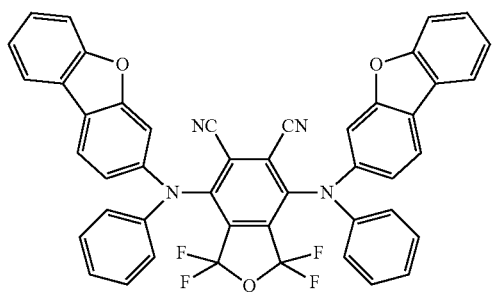
(I-20)
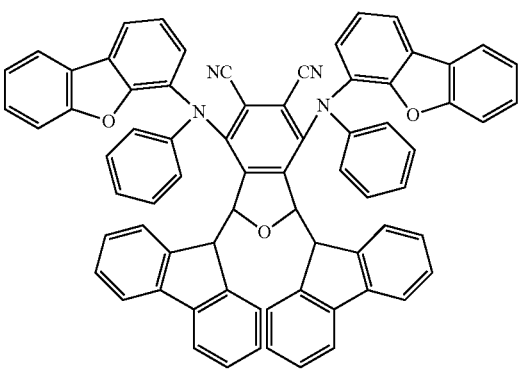
(I-21)
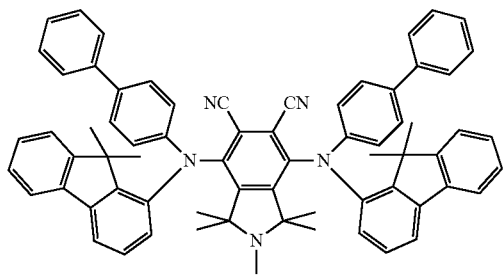
(I-22)
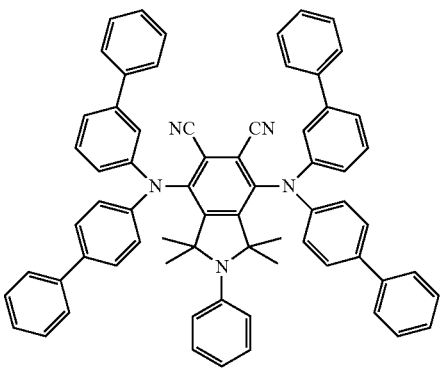

-continued
(I-23)
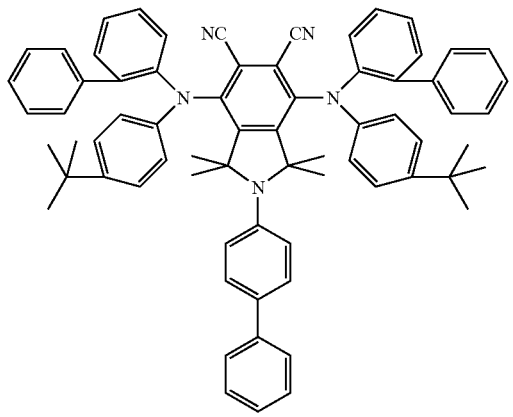
(I-24)
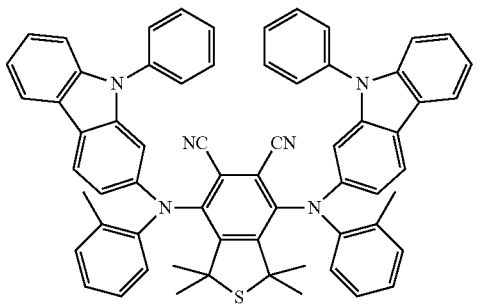
(I-25)
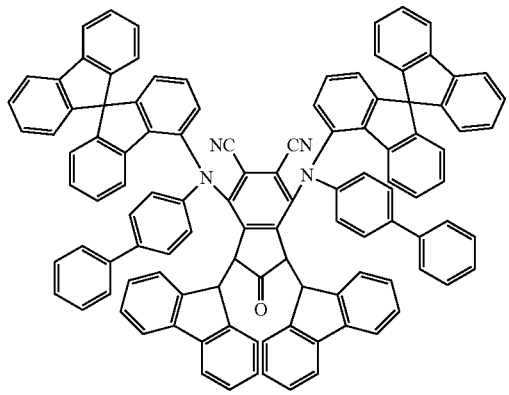
(I-26)
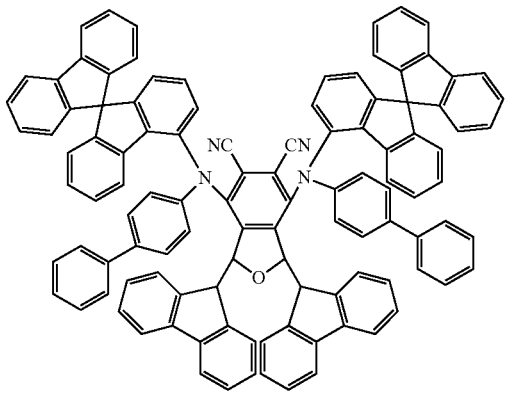
(I-27)
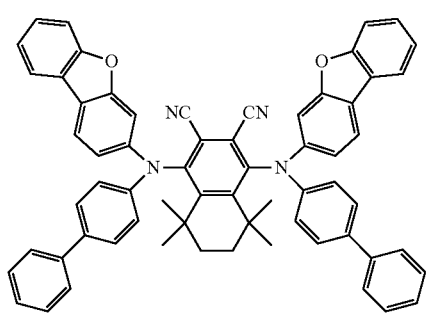
(I-28)
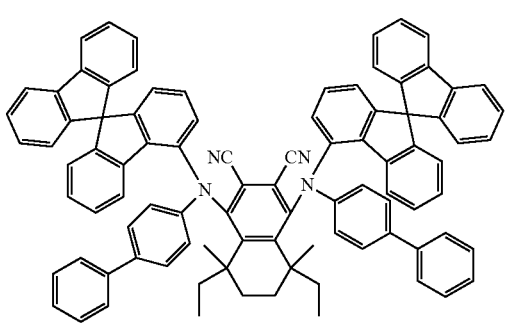
(I-29)
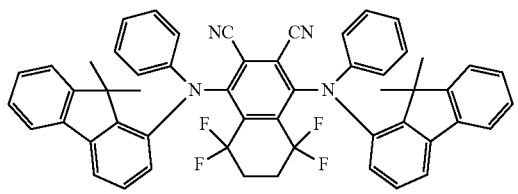
(I-30)
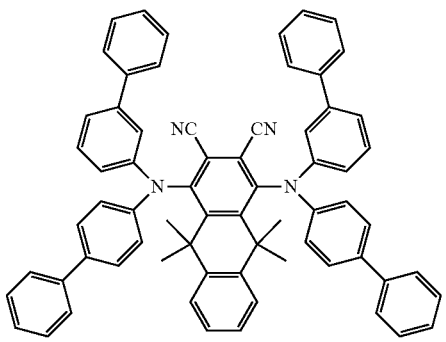

-continued
(I-31)
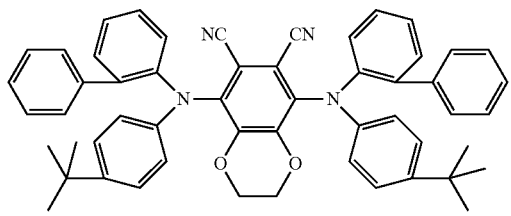
(I-32)
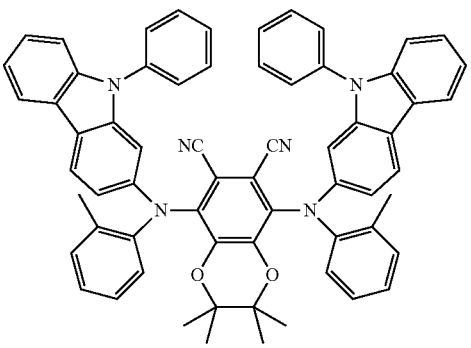
(I-33)
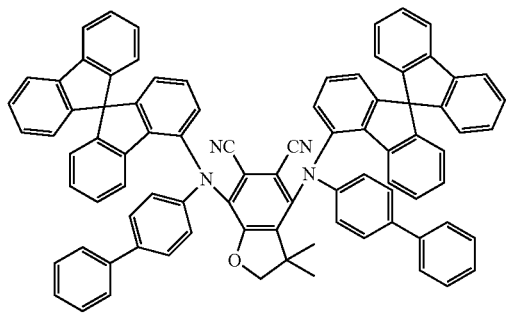
(I-34)
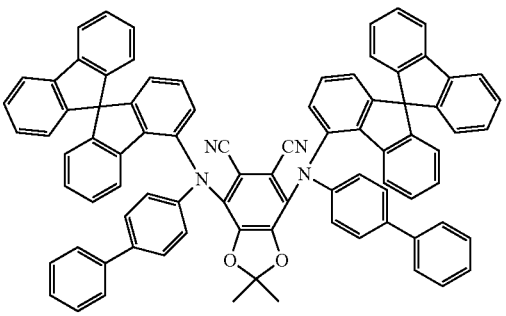
(I-35)
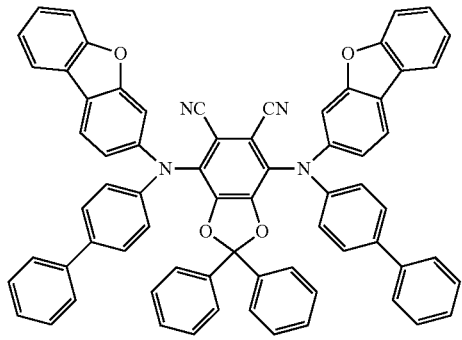
(I-36)
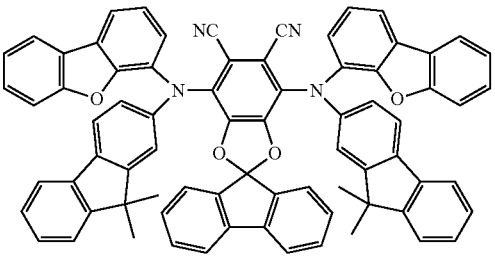
(I-37)
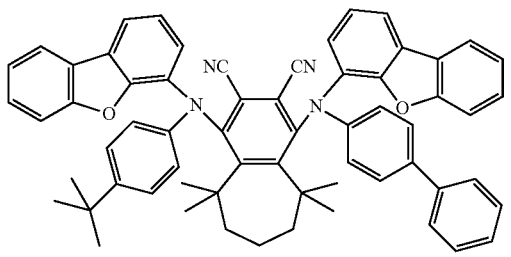
(I-38)
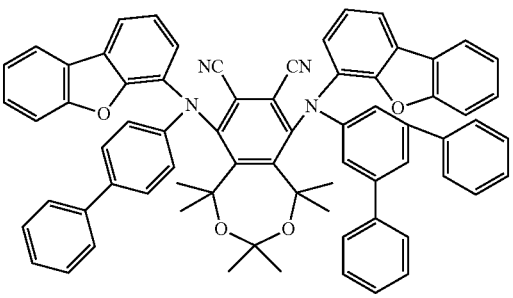
(I-39)
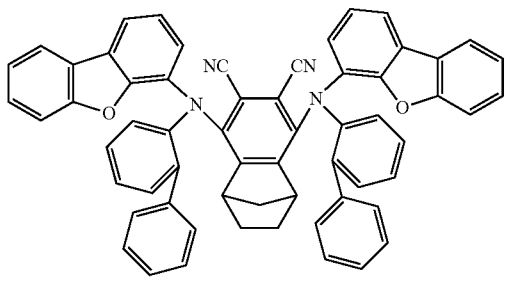
(I-40)
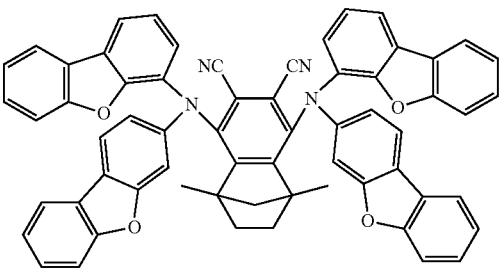

-continued
(I-41) 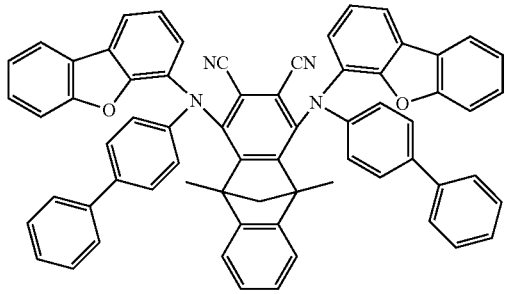
(I-42) 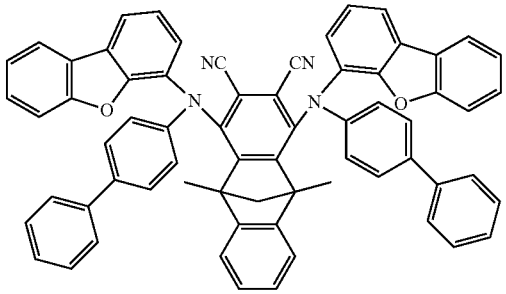
(I-43) 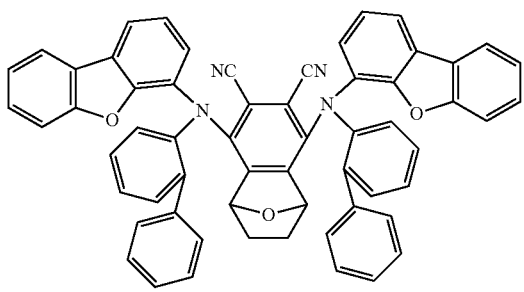
(I-44) 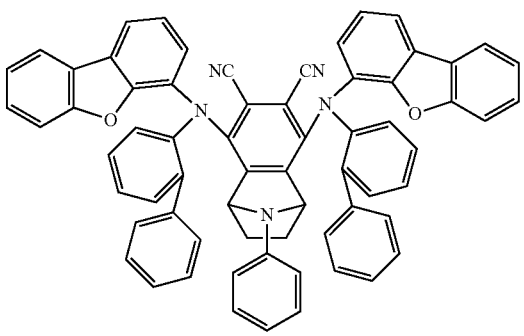
(I-45) 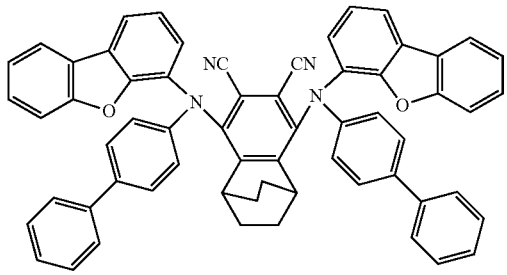
(I-46) 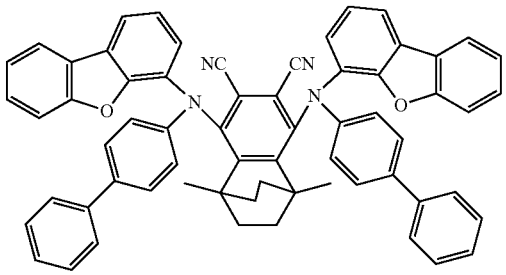
(I-47) 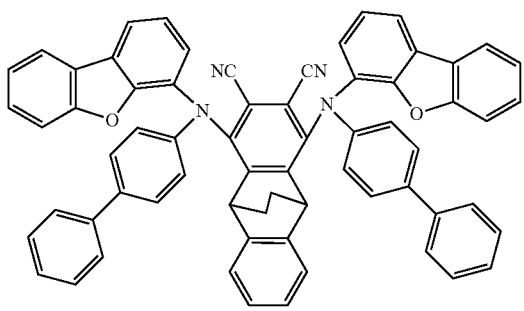
(I-48) 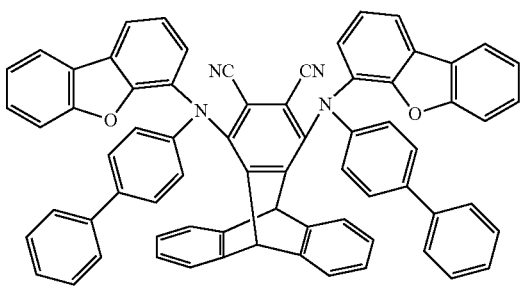
(I-49) 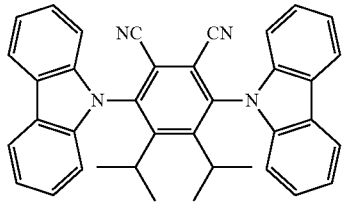
(I-50) 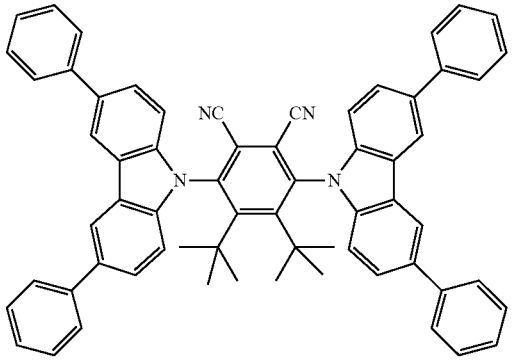

-continued
(I-51)
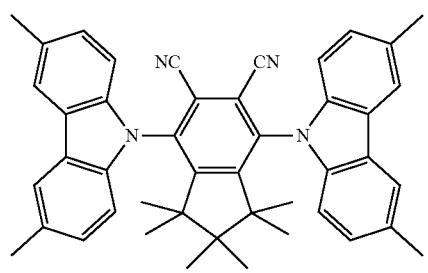
(I-52)
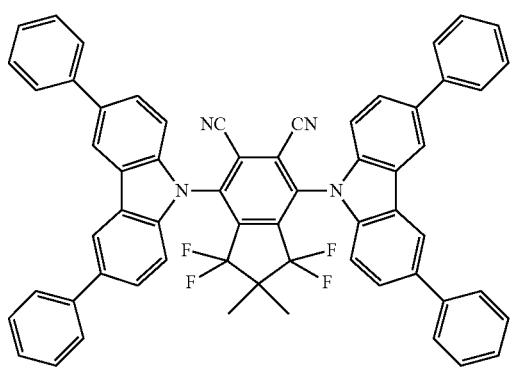
(I-53)
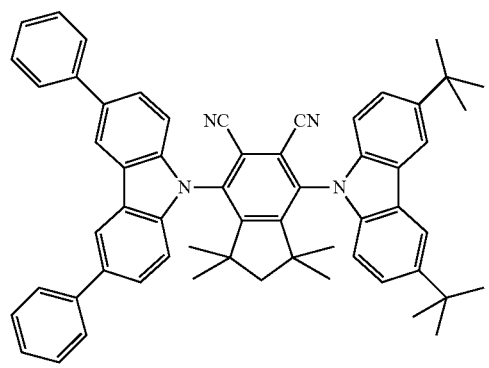
(I-54)
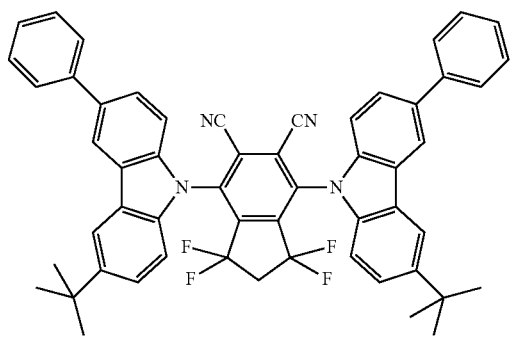
(I-55)
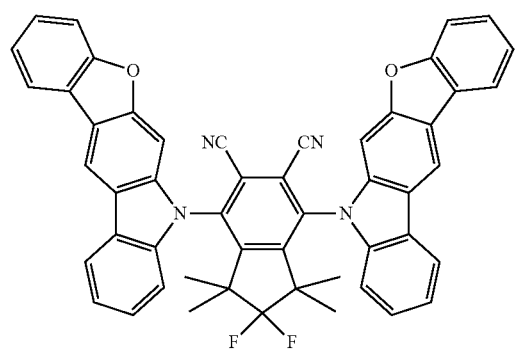
(I-56)
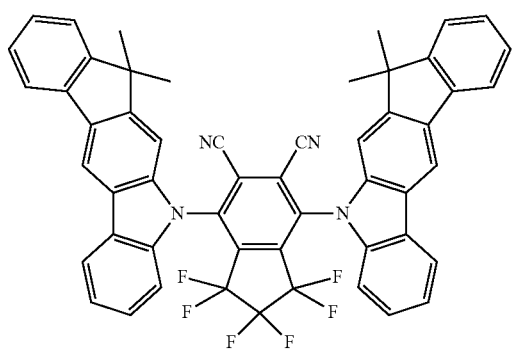
(I-57)
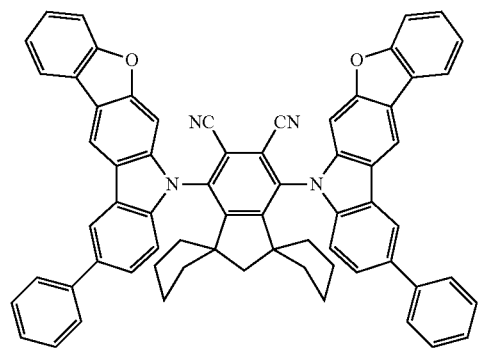
(I-58)
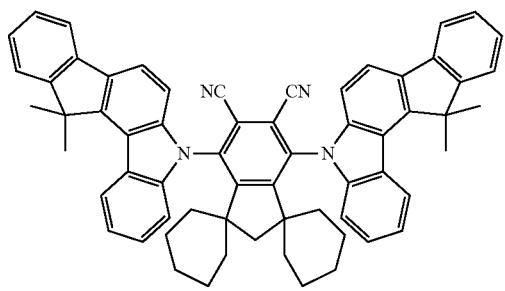

-continued
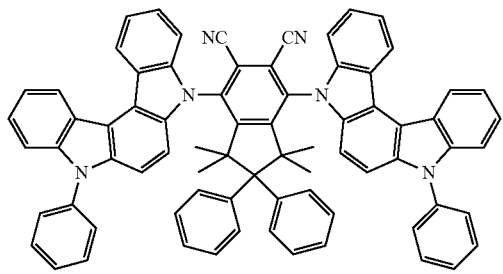
(I-59)
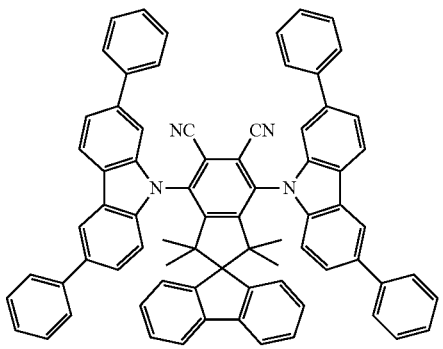
(I-60)
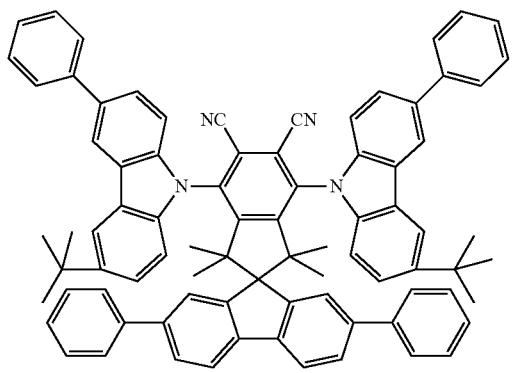
(I-61)
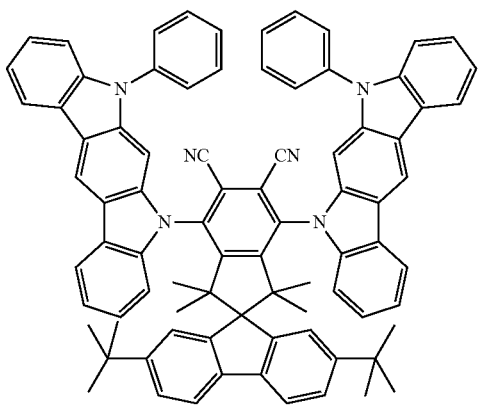
(I-62)
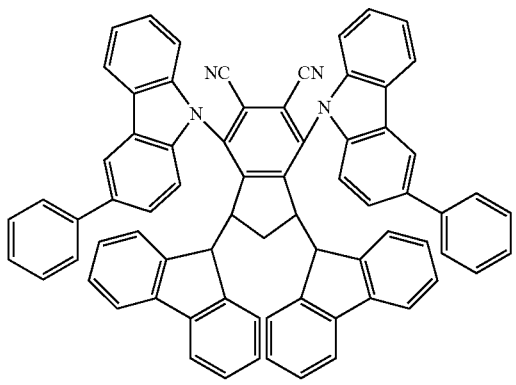
(I-63)
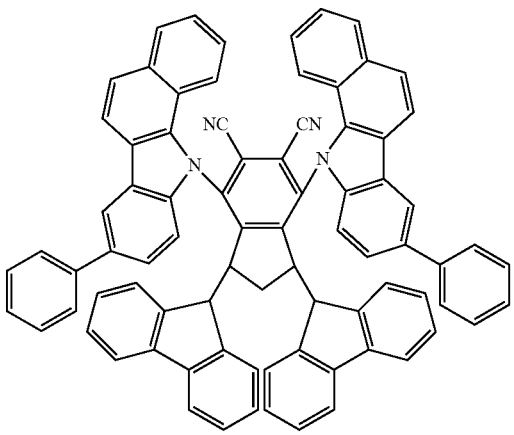
(I-64)
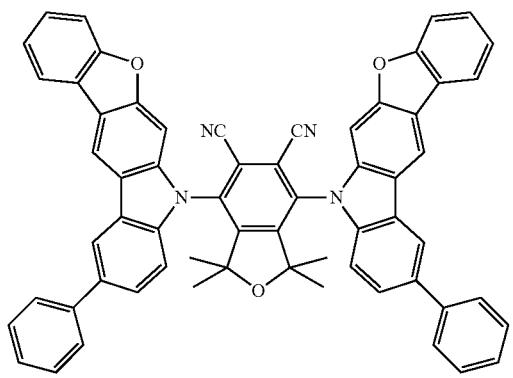
(I-65)
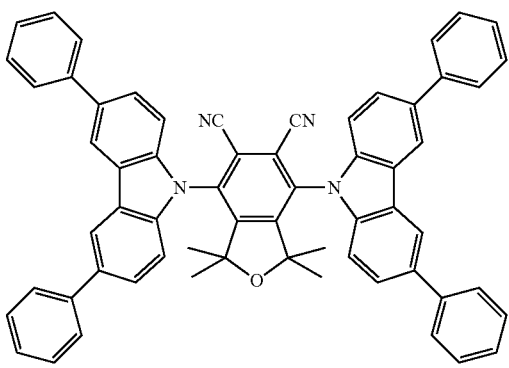
(I-66)

-continued
(I-67)
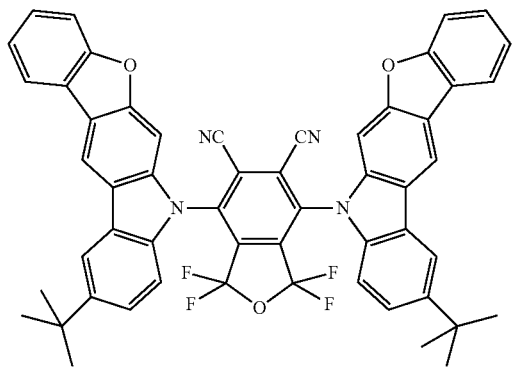
(I-68)
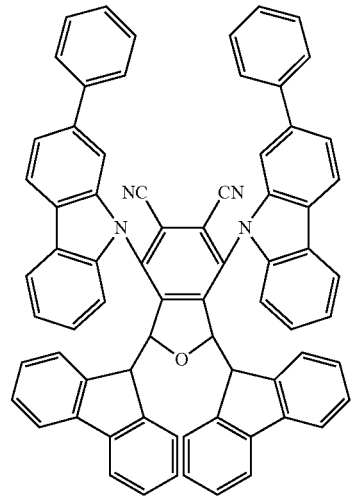
(I-69)
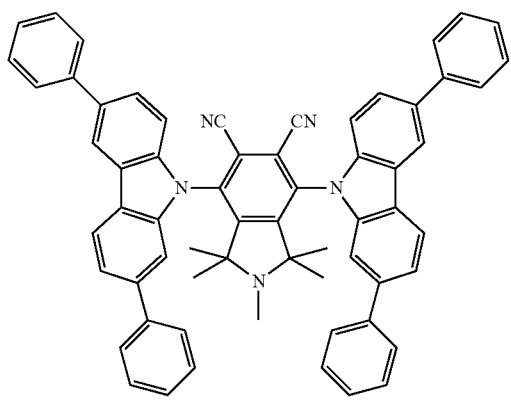
(I-70)
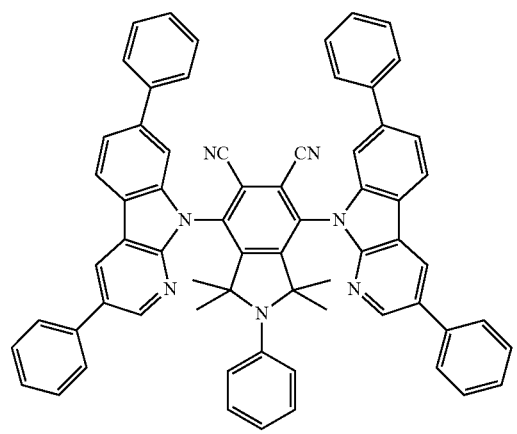
(I-71)
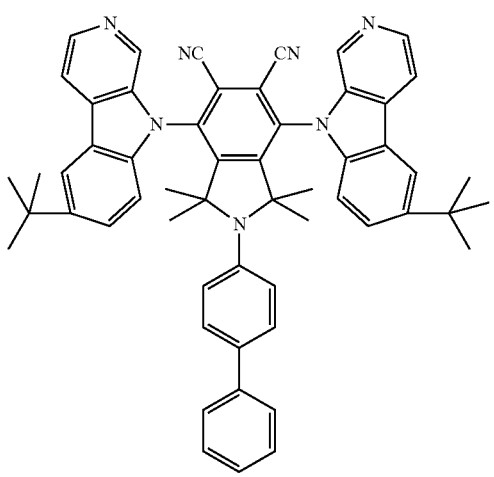
(I-72)
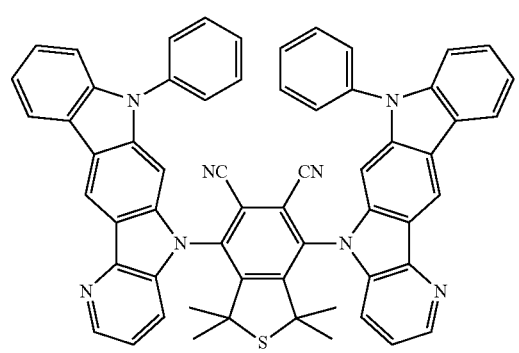

-continued
(I-73)
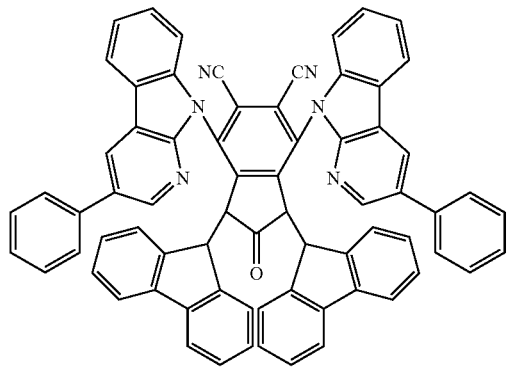
(I-74)
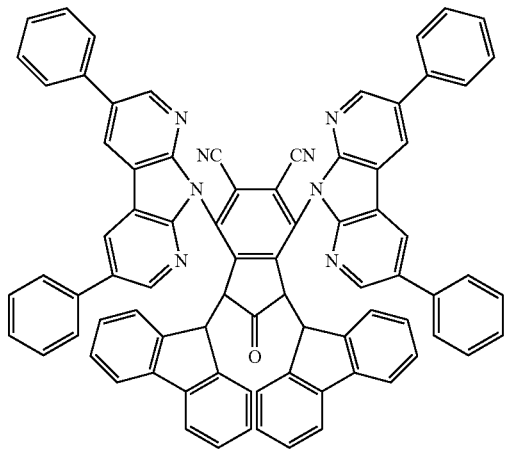
(I-75)
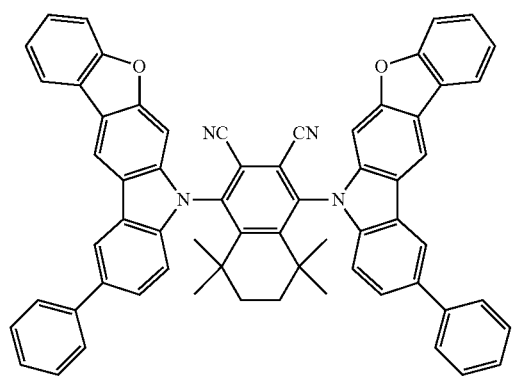
(I-76)
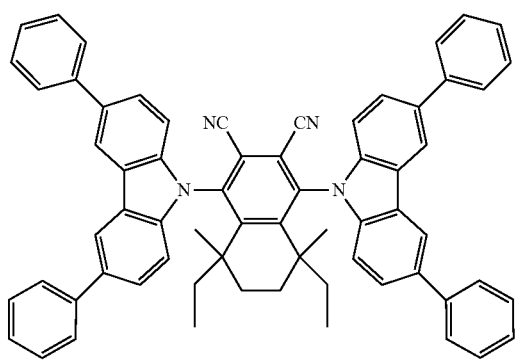
(I-77)
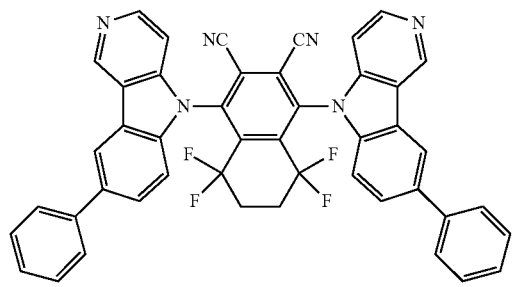
(I-78)
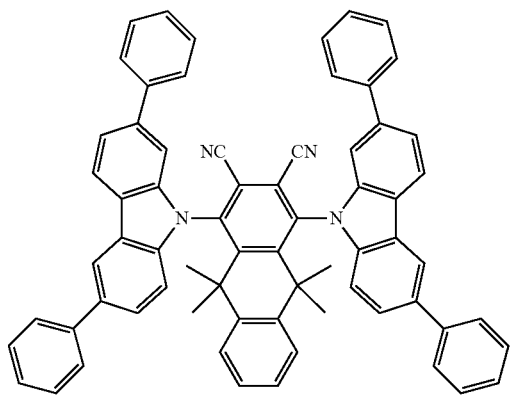
(I-79)
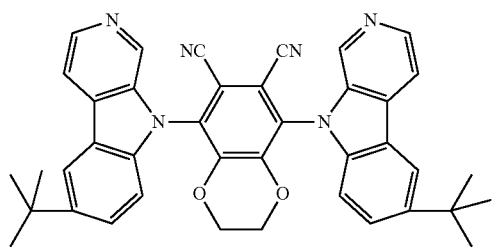
(I-80)
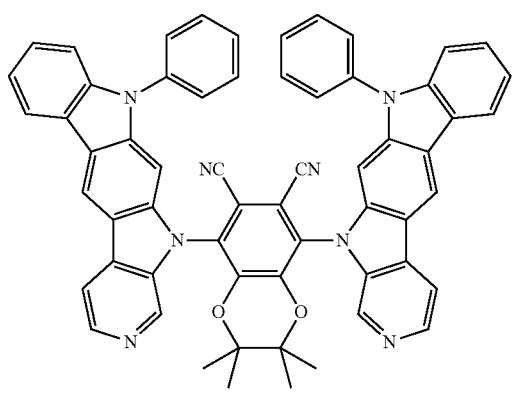

-continued
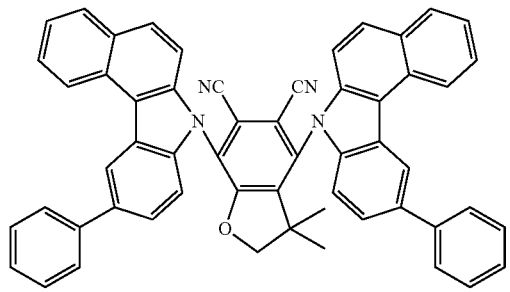
(I-81)
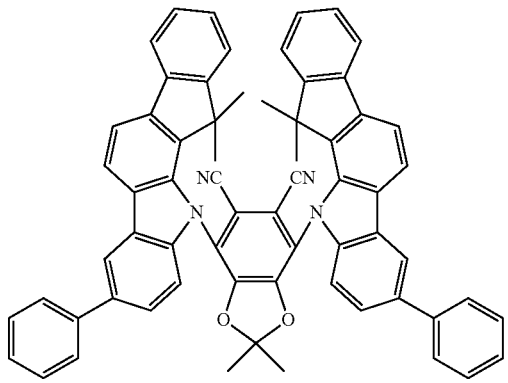
(I-82)
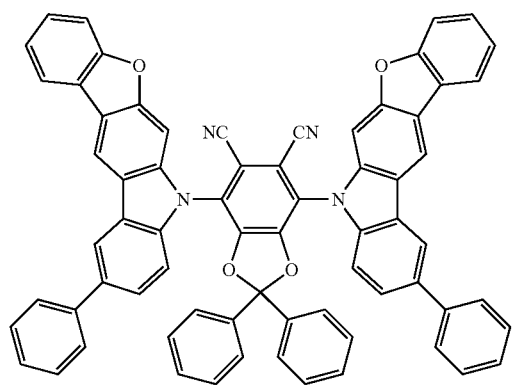
(I-83)
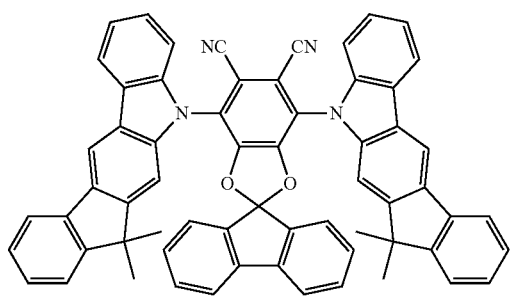
(I-84)
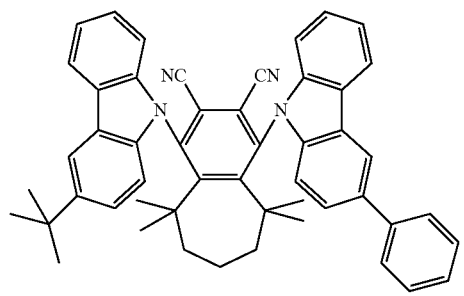
(I-85)
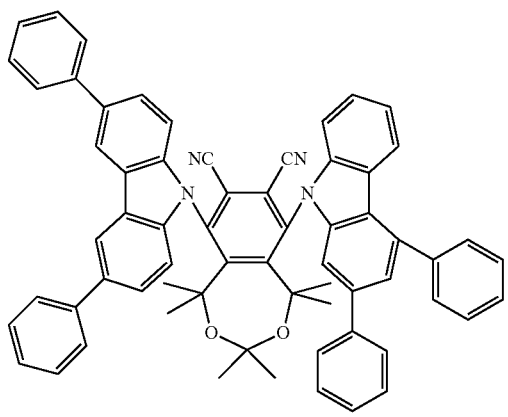
(I-86)
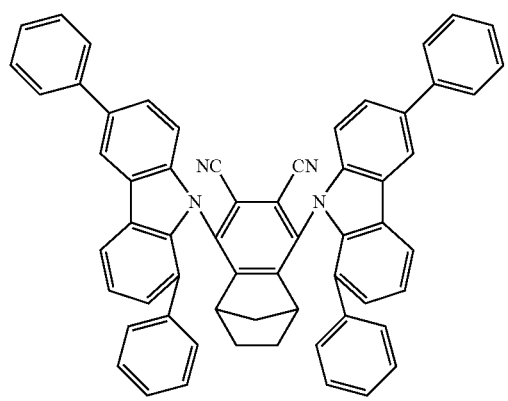
(I-87)
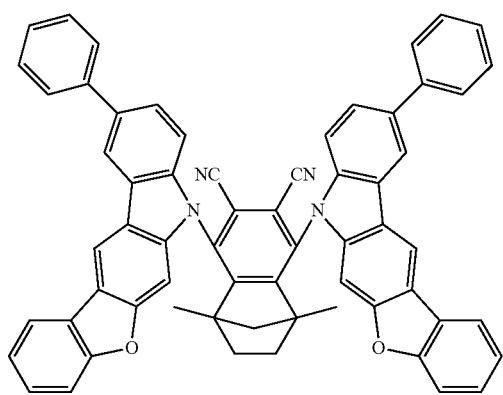
(I-88)

-continued
(I-89)
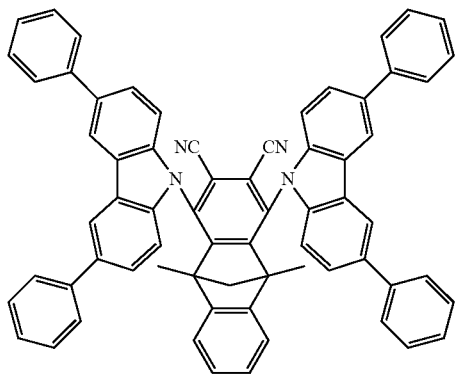
(I-90)
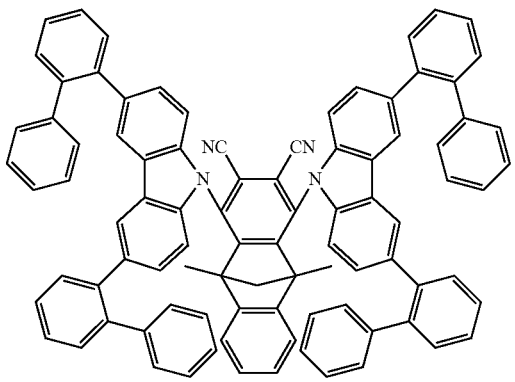
(I-91)
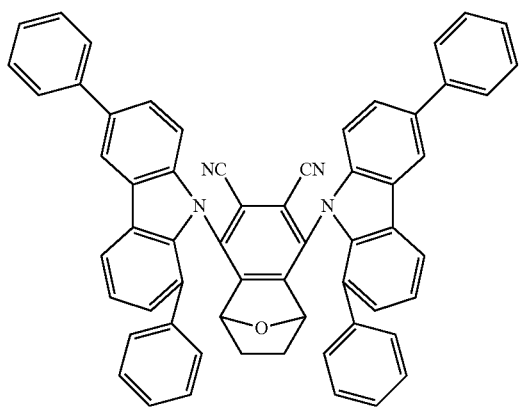
(I-92)
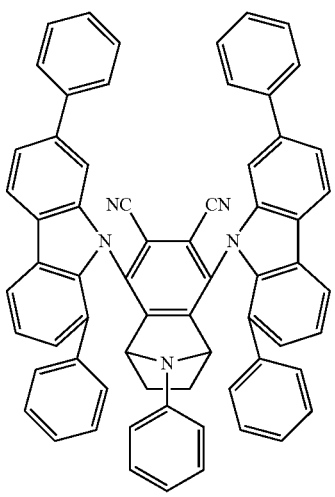
(I-93)
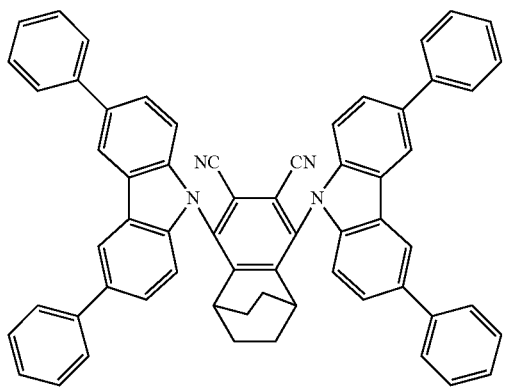
(I-94)
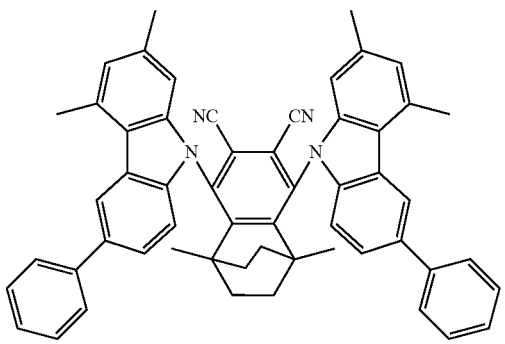

-continued
(I-95)
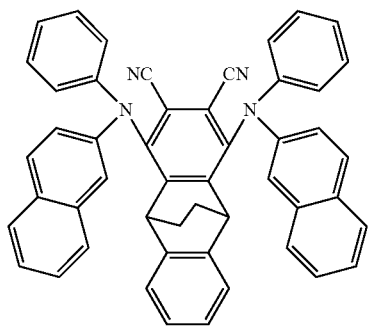
(I-96)
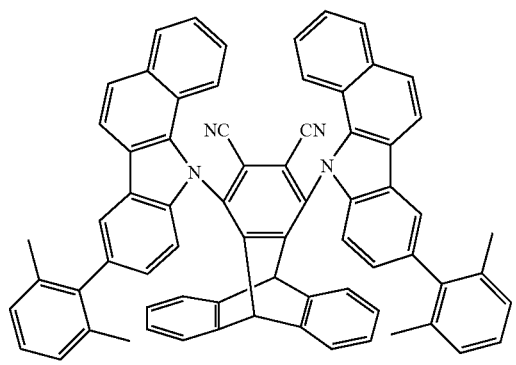
(I-97)
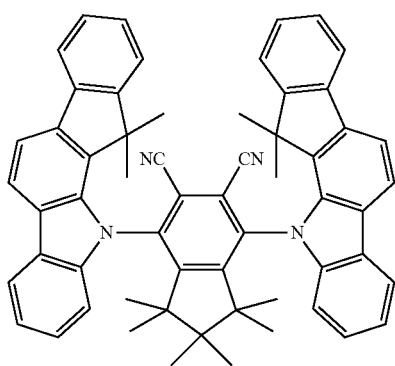
(I-98)
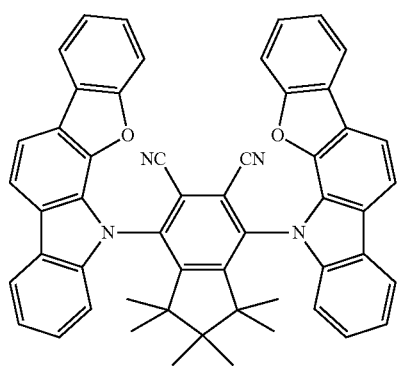
(I-99)
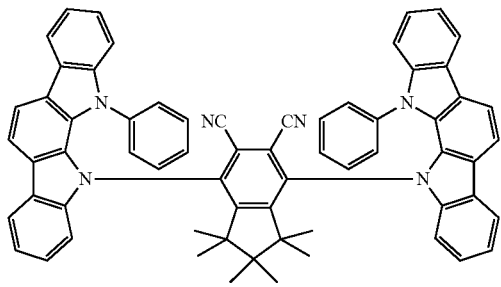
(I-100)
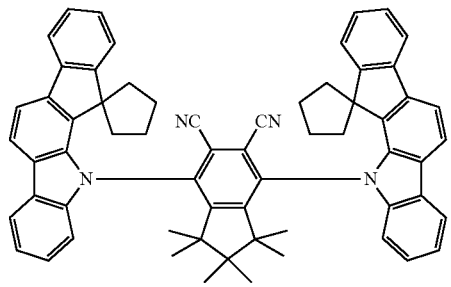
(I-101)
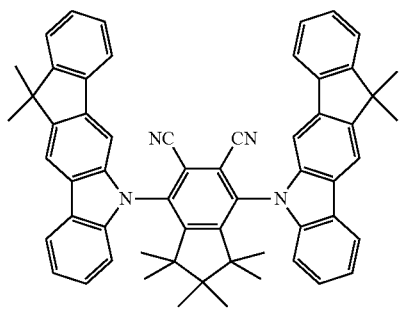
(I-102)
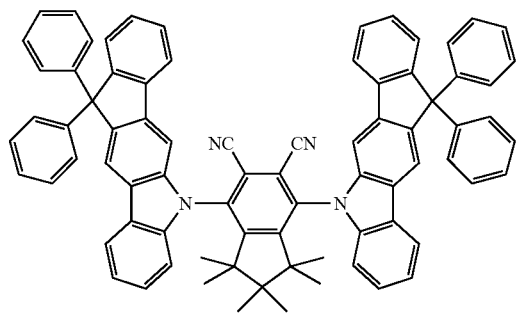

-continued
(I-103)
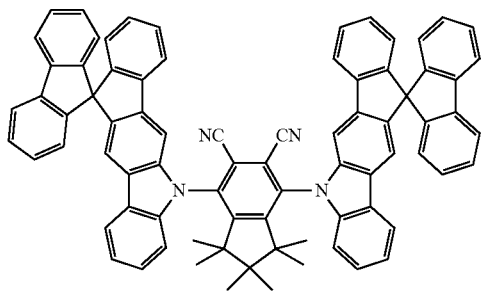
(I-104)
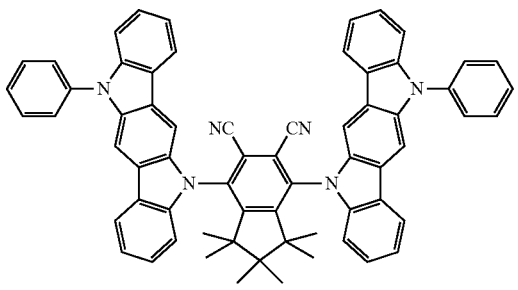
(I-105)
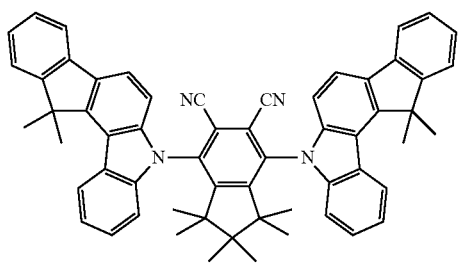
(I-106)
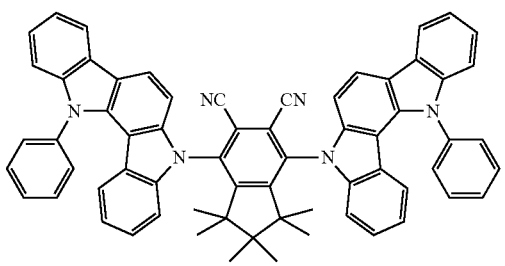
(I-107)
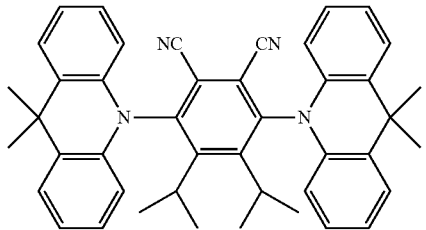
(I-108)
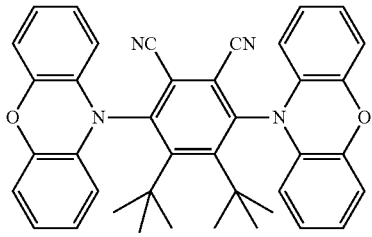
(I-109)
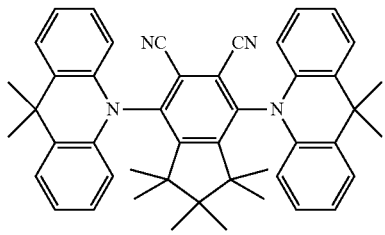
(I-110)
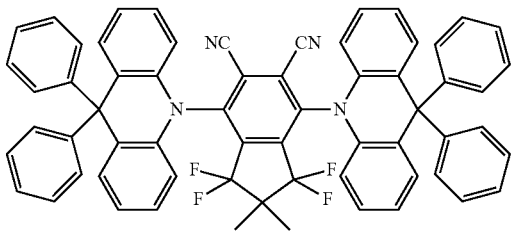
(I-111)
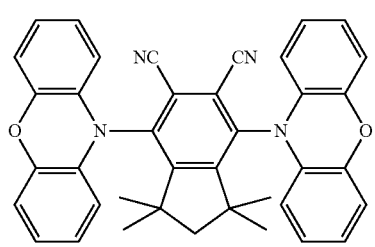

(I-112)
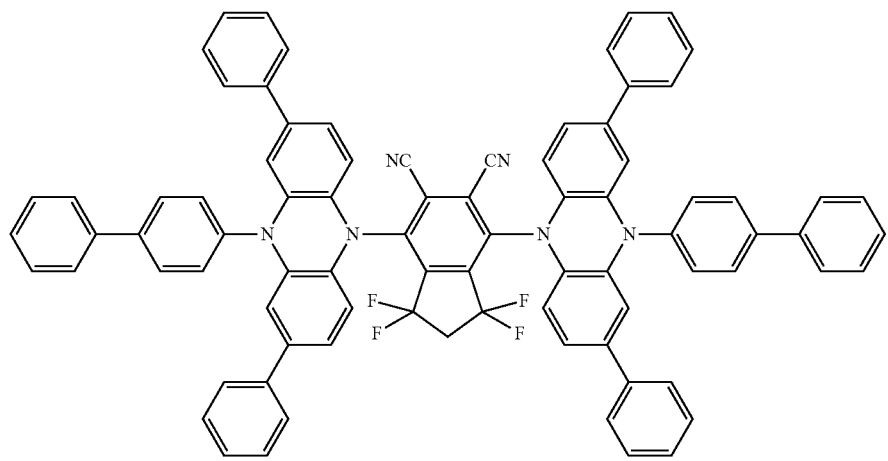
(I-113)
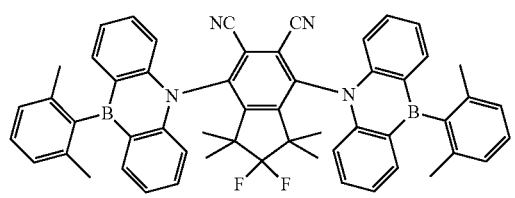
(I-114)
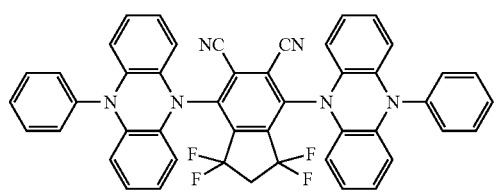
(I-115)
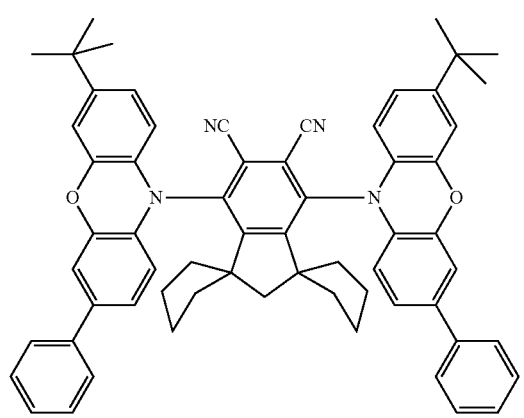
(I-116)
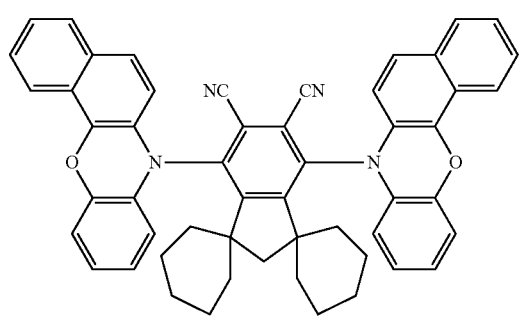
(I-117)
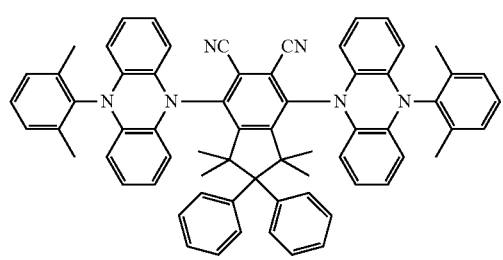
(I-118)
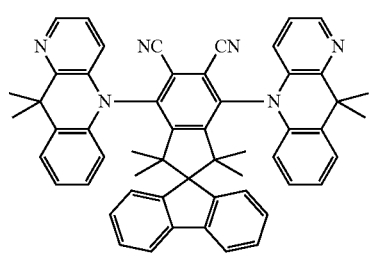
(I-119)
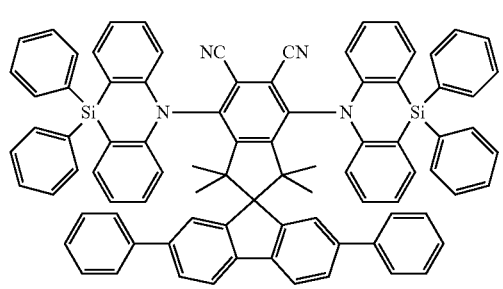
(I-120)
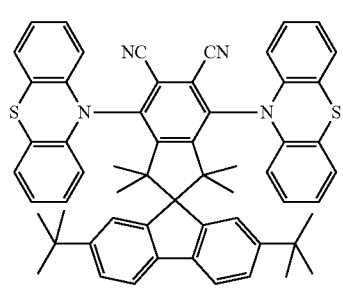

-continued
(I-121)
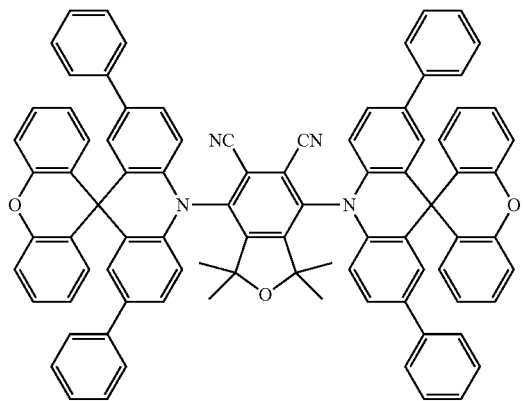
(I-122)
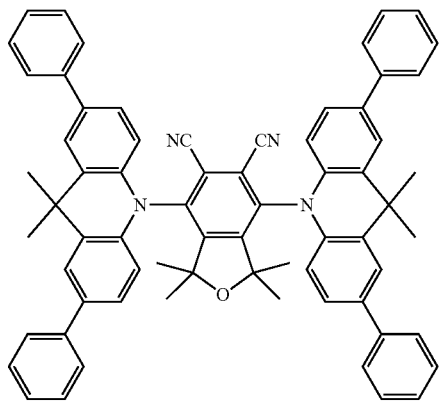
(I-123)
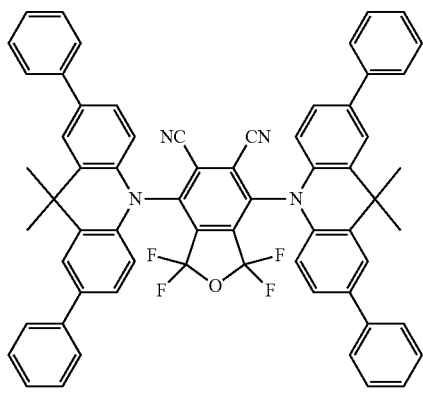
(I-124)
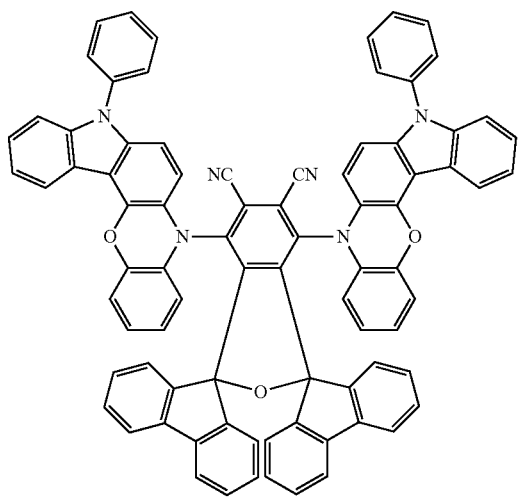
(I-125)
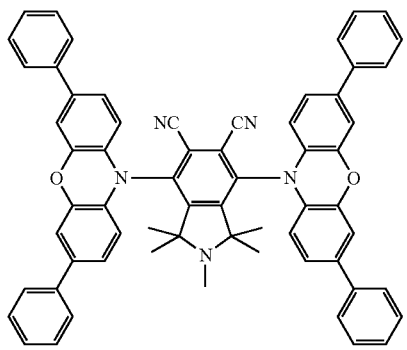
(I-126)
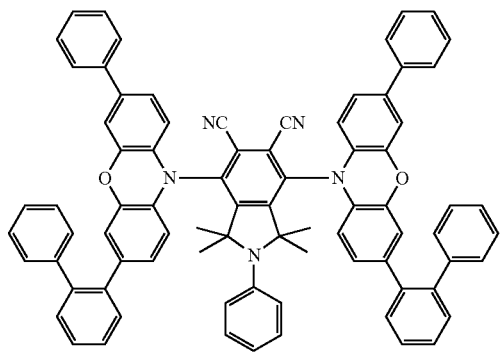

-continued
(I-127)
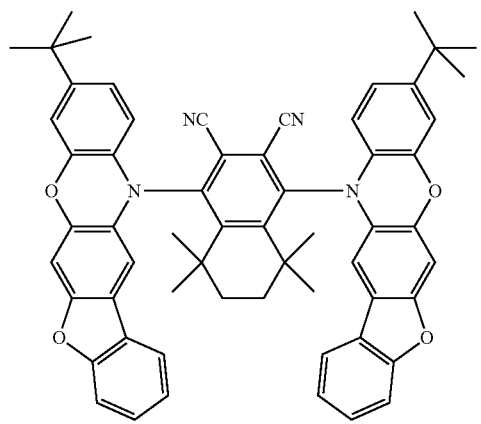
(I-128)
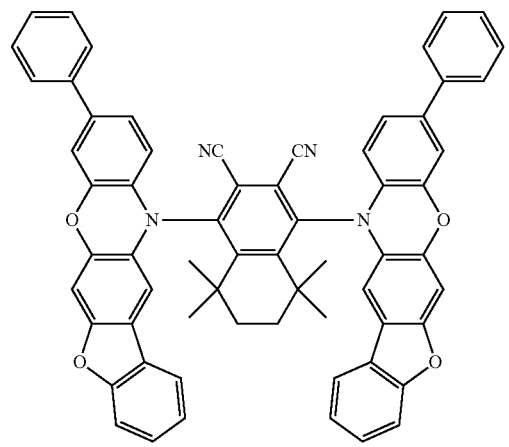
(I-129)
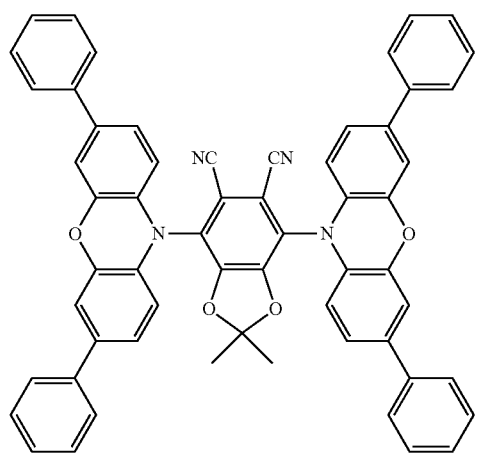
(I-130)
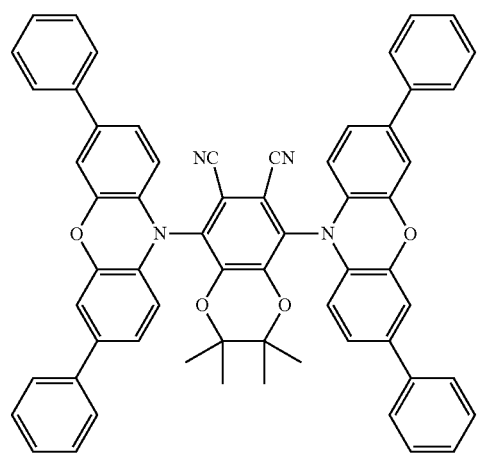
(I-131)
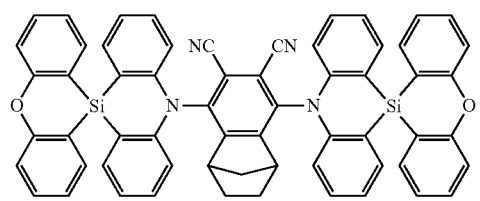
(I-132)
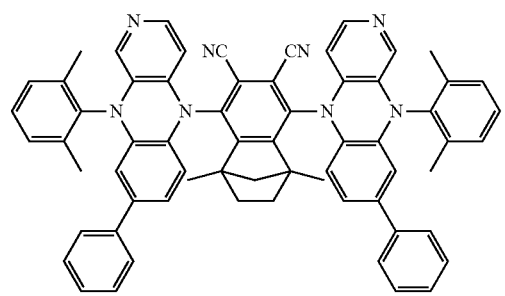

-continued
(I-133)
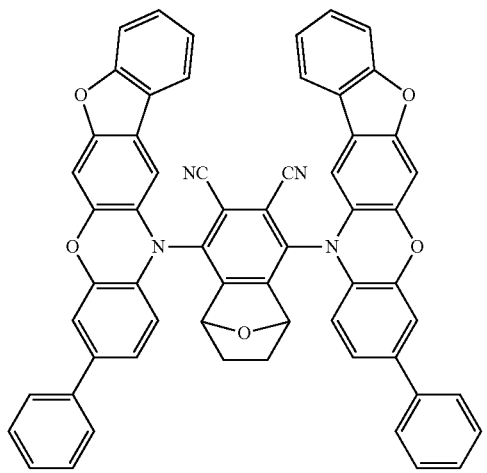
(I-134)
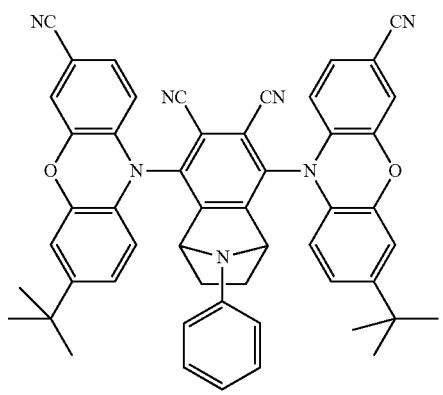
(I-135)
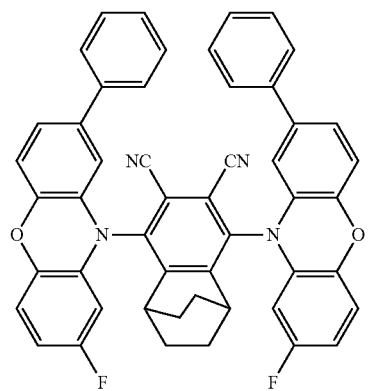
(I-136)
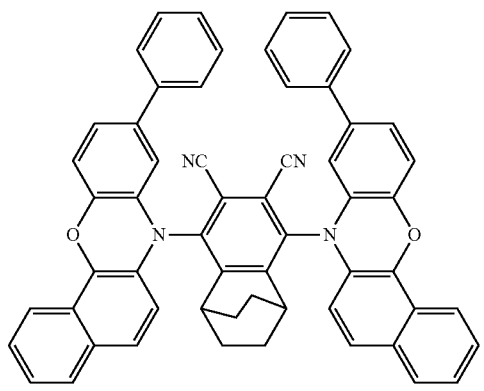
(I-137)
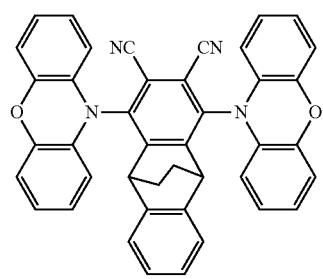
(I-138)
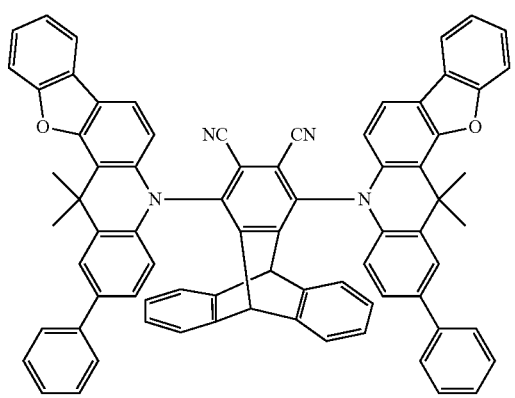

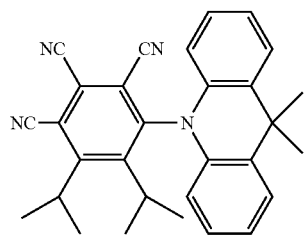
(I-139)
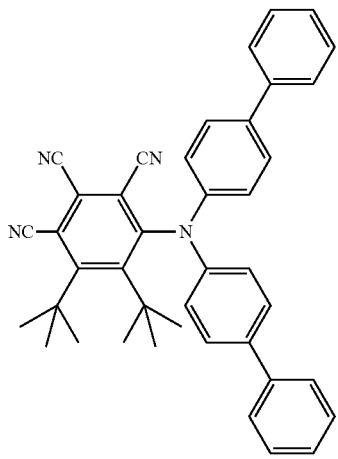
(I-140)
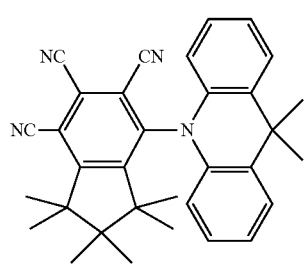
(I-141)
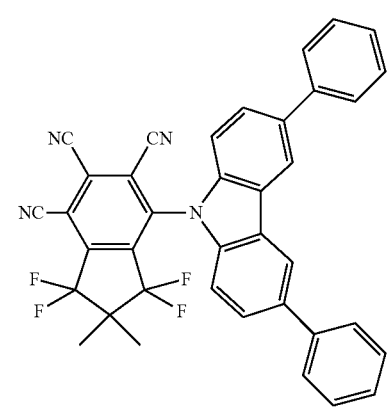
(I-142)
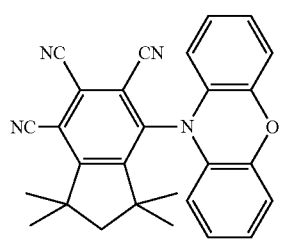
(I-143)
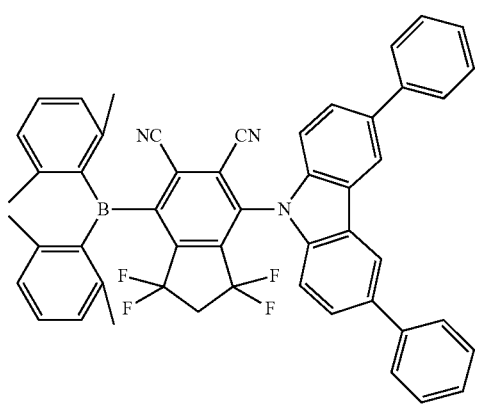
(I-144)

-continued
(I-145)
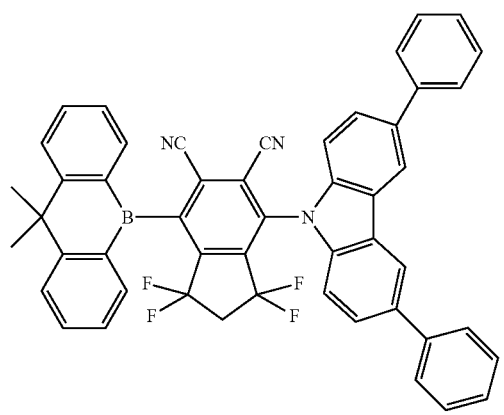
(I-146)
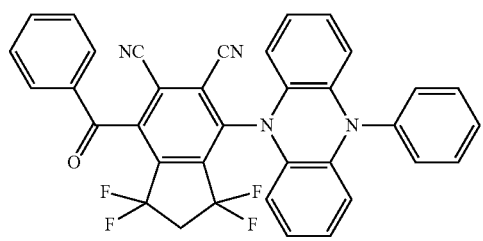
(I-147)
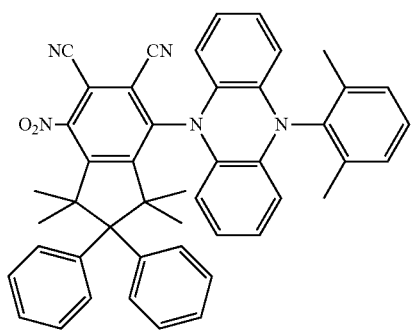
(I-148)
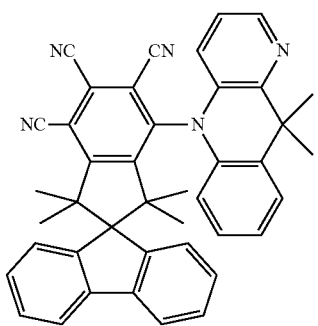
(I-149)
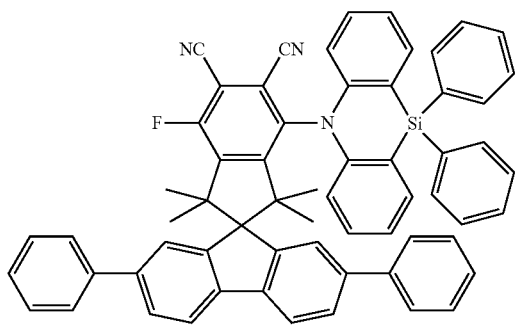
(I-150)
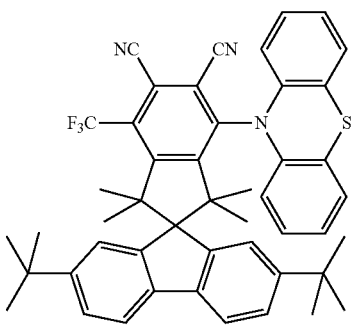
(I-151)
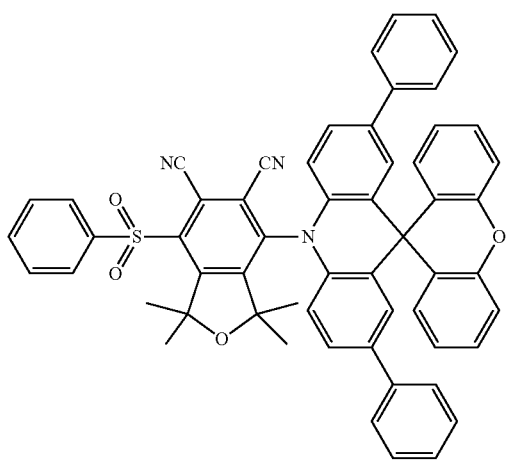
(I-152)
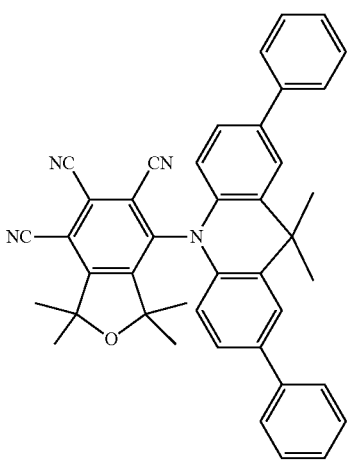

-continued
(I-153)
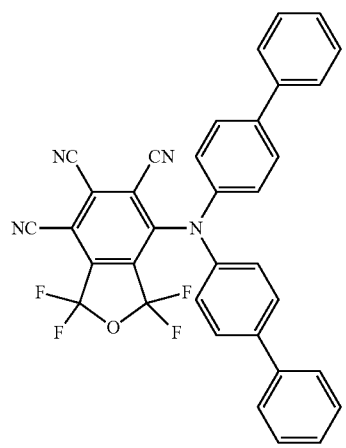
(I-154)
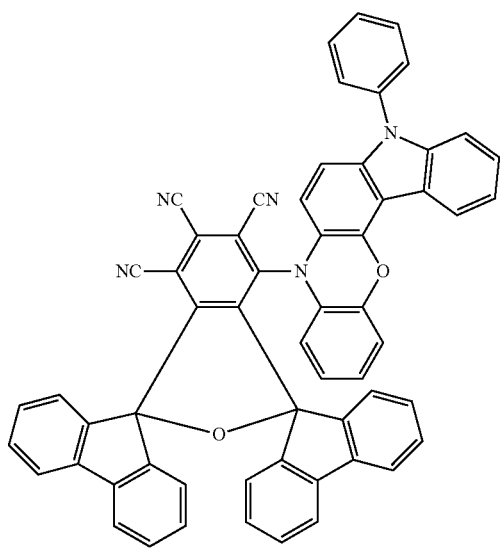
(I-155)
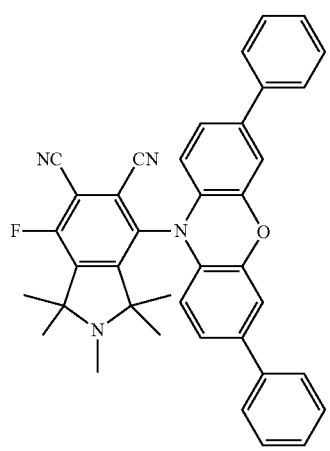
(I-156)
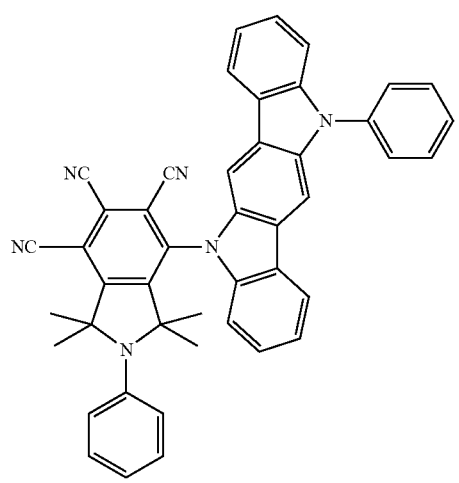
(I-157)
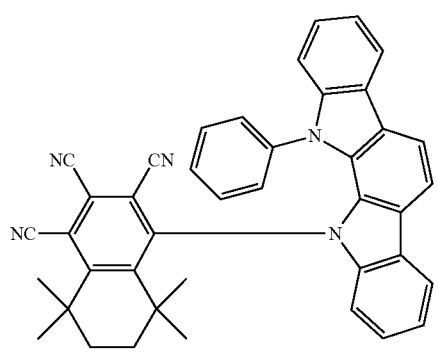
(I-158)
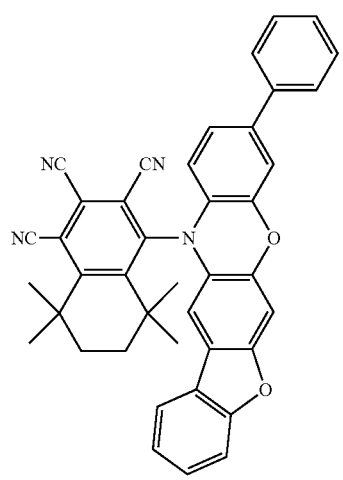

-continued
(I-159)
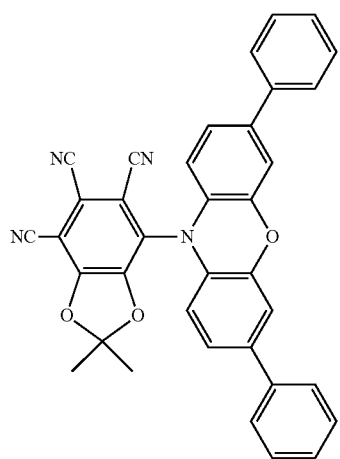
(I-160)
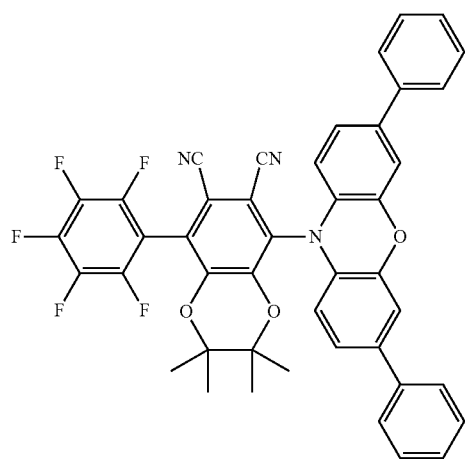
(I-161)
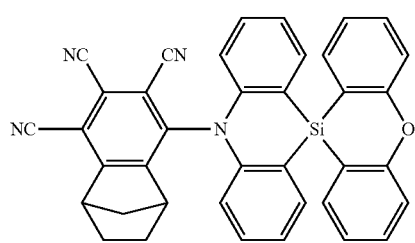
(I-162)
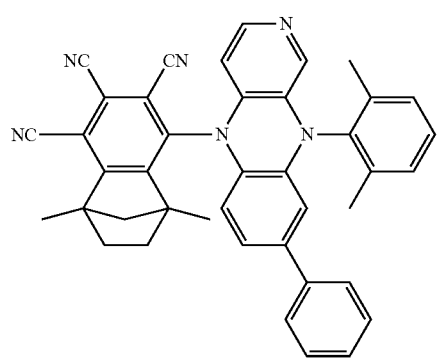
(I-163)
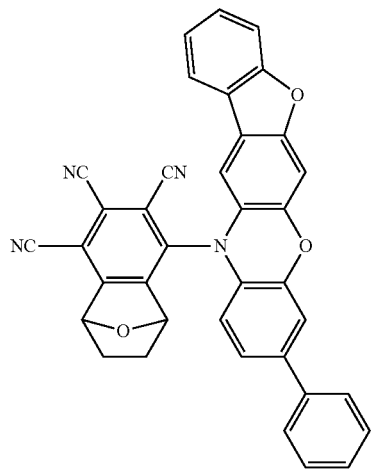
(I-164)
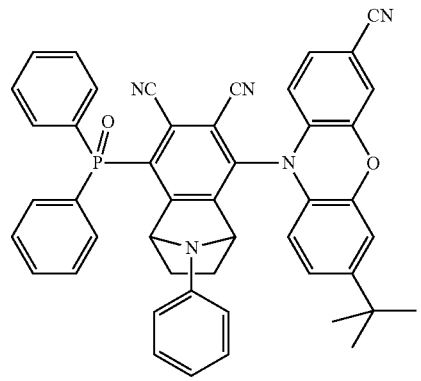
(I-165)
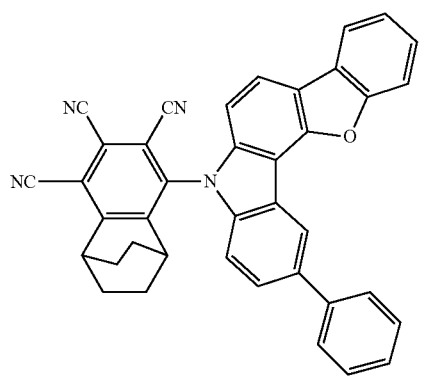
(I-166)
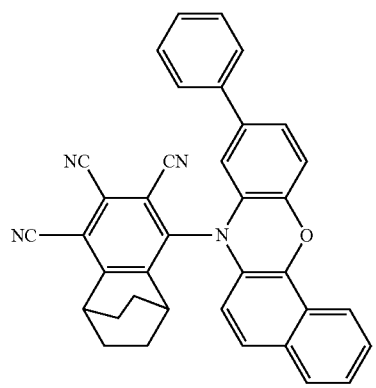

(I-167)
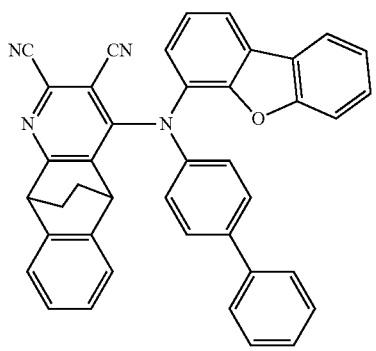
(I-168)
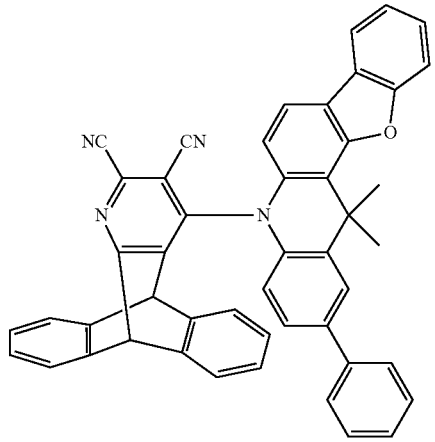
(I-169)
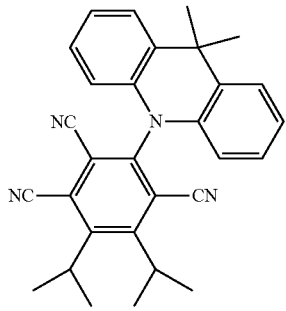
(I-170)
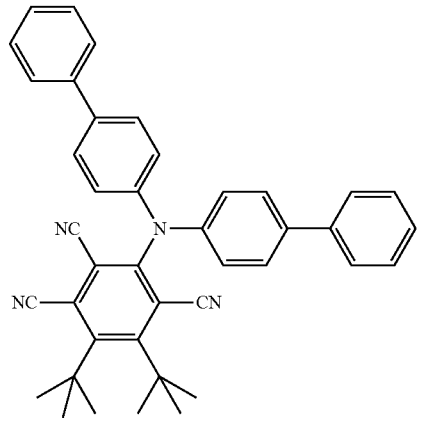
(I-171)
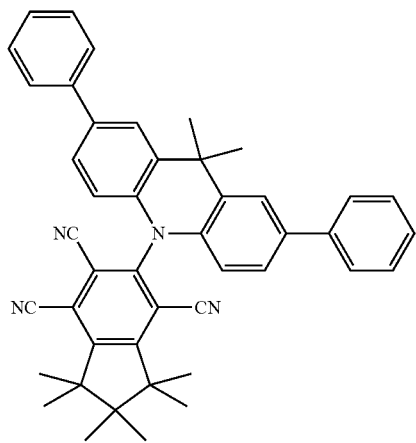
(I-172)
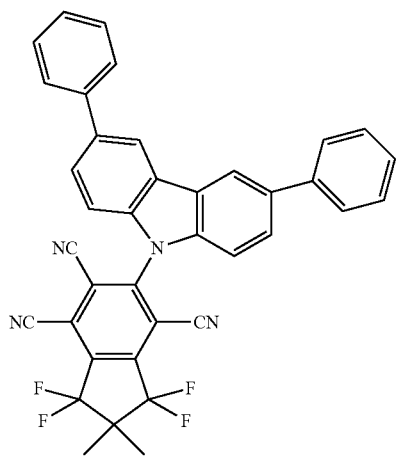

-continued
(I-173)
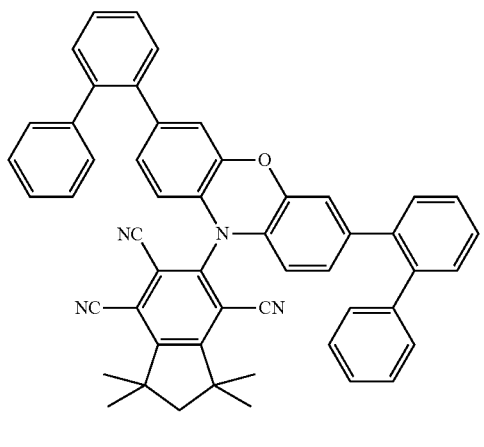
(I-174)
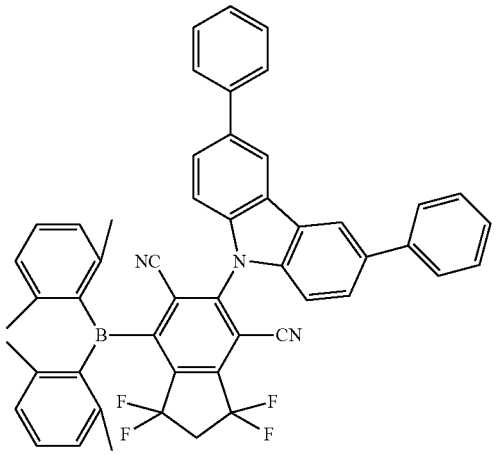
(I-175)
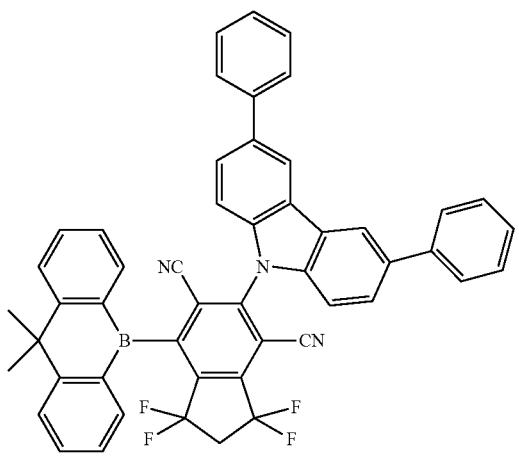
(I-176)
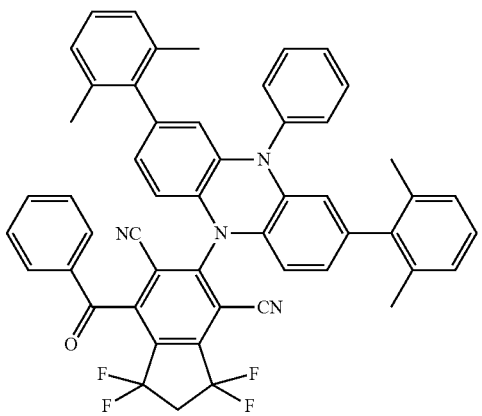
(I-177)
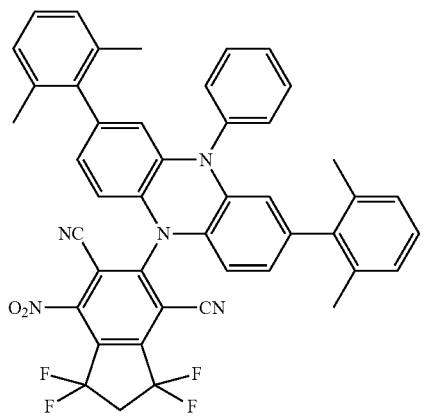
(I-178)
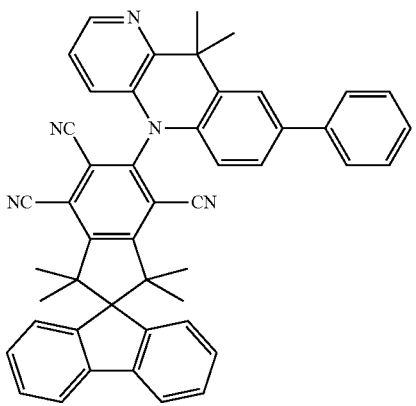

-continued
(I-179)
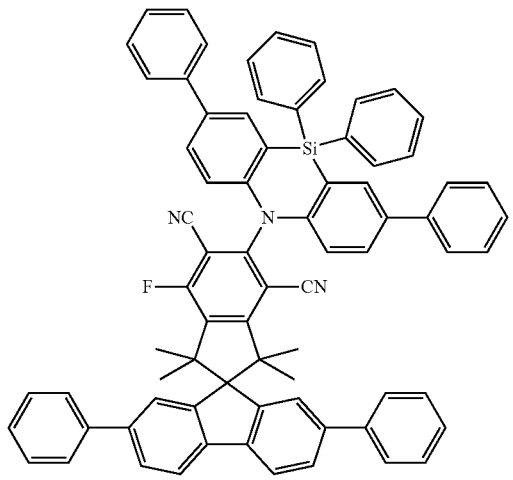
(I-180)
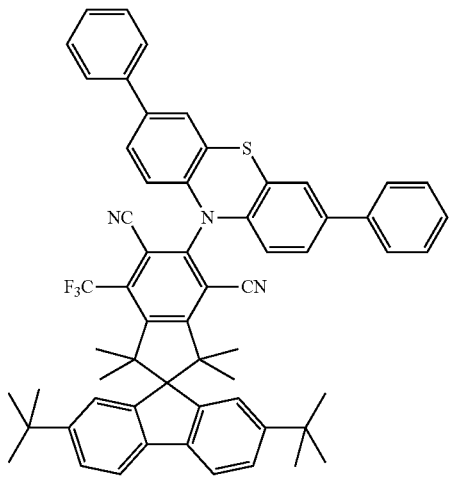
(I-181)
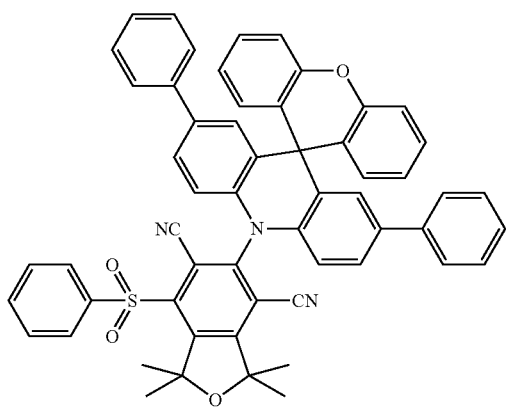
(I-182)
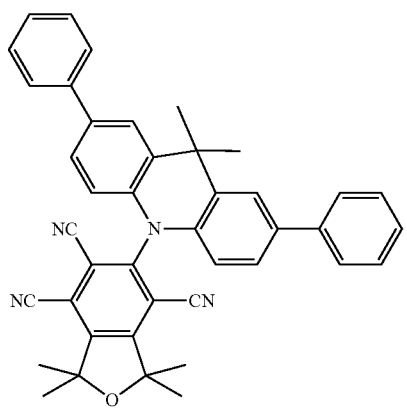
(I-183)
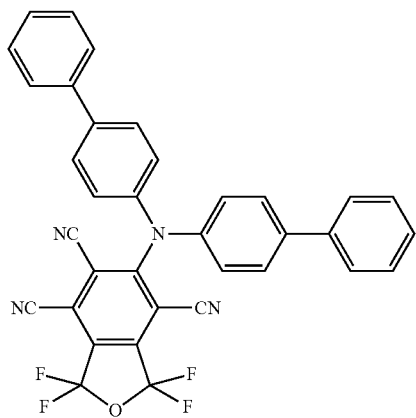
(I-184)
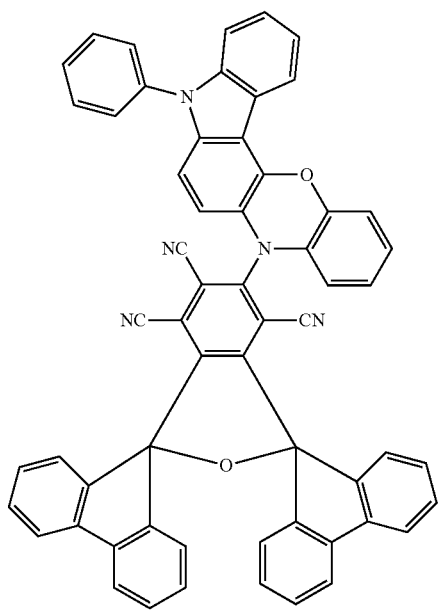

(I-185)
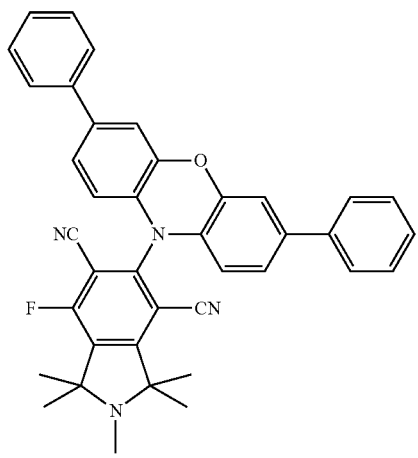
(I-186)
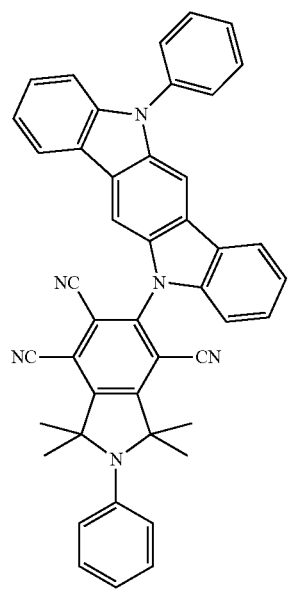
(I-187)
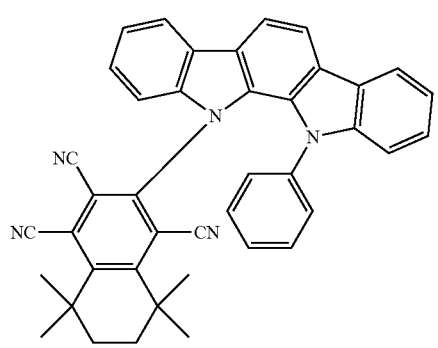
(I-188)
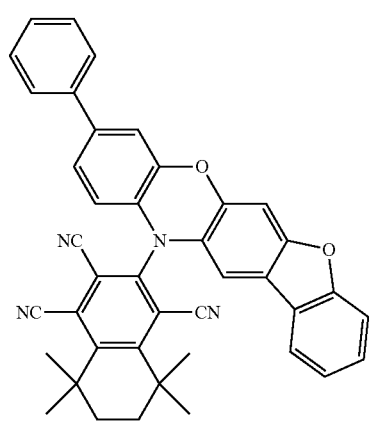
(I-189)
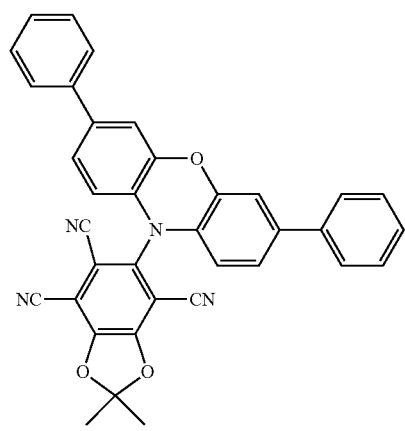
(I-190)
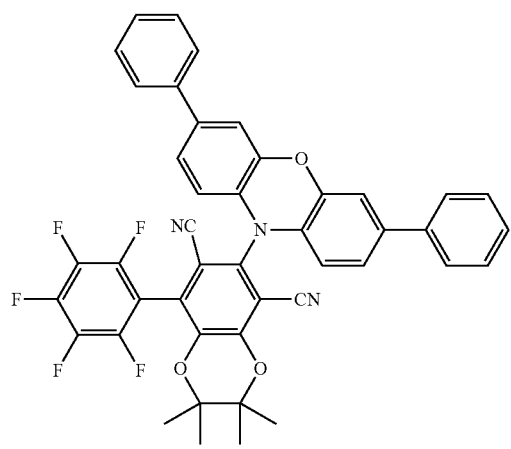

-continued
(I-191)
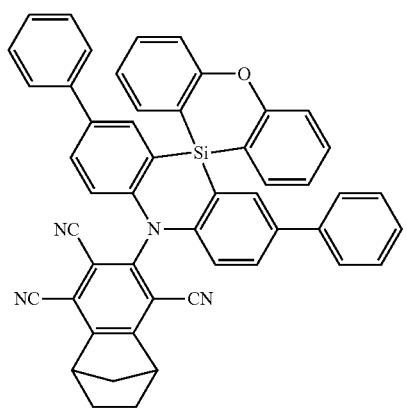
(I-192)
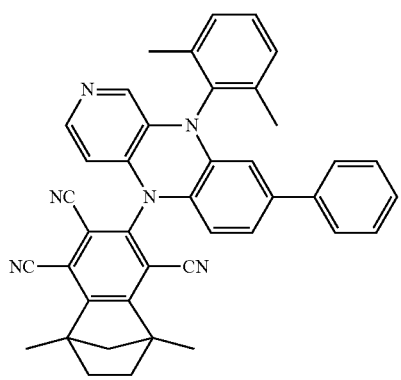
(I-193)
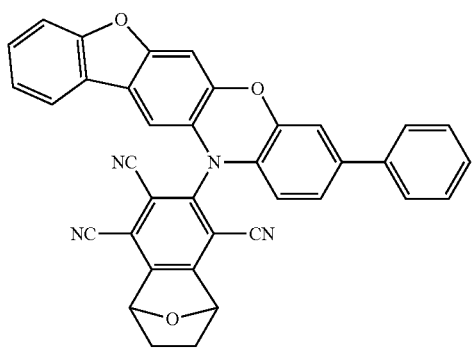
(I-194)
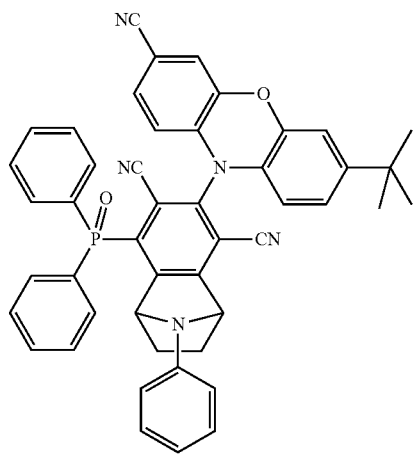
(I-195)
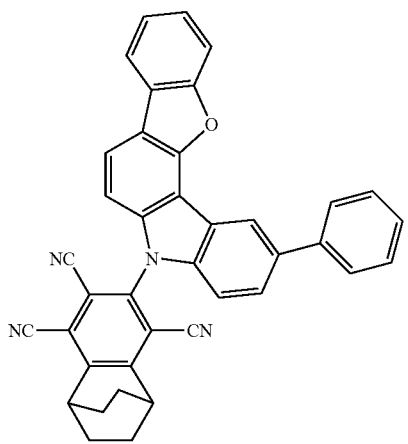
(I-196)
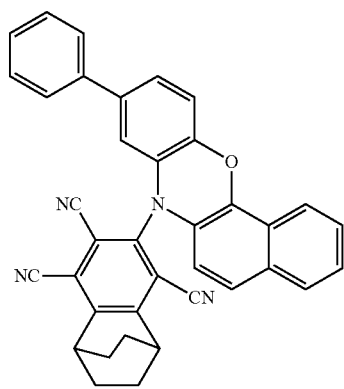

-continued
(I-197)
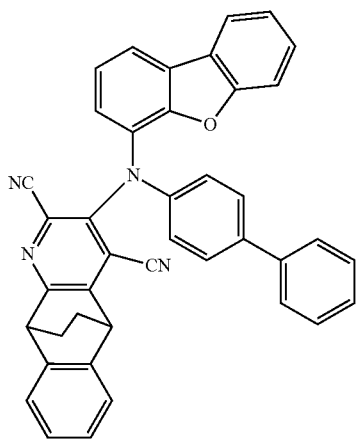
(I-198)
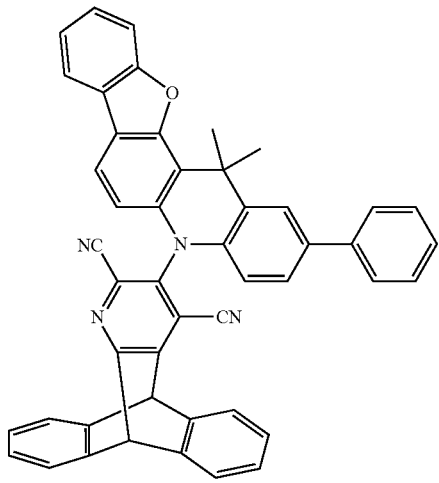
(I-199)
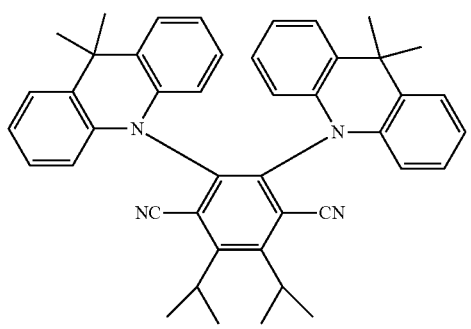
(I-200)
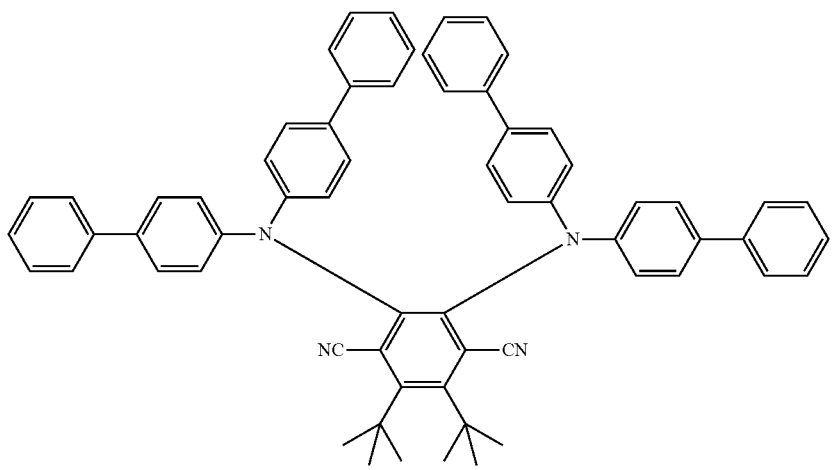

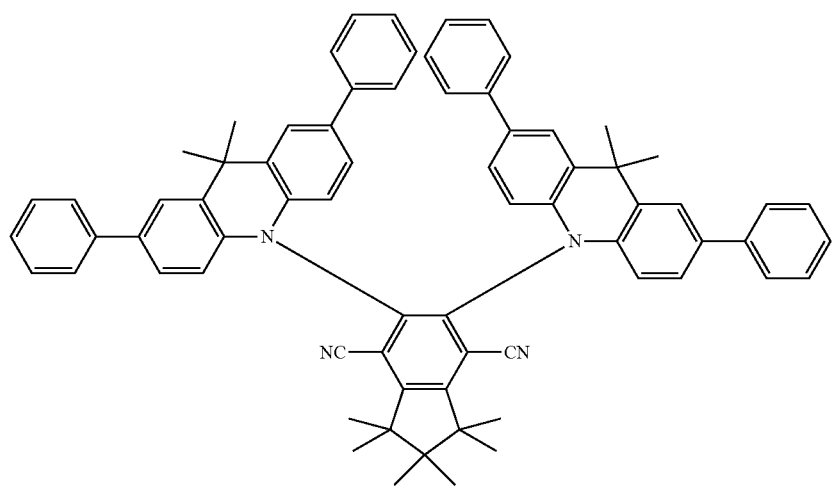
(I-201)
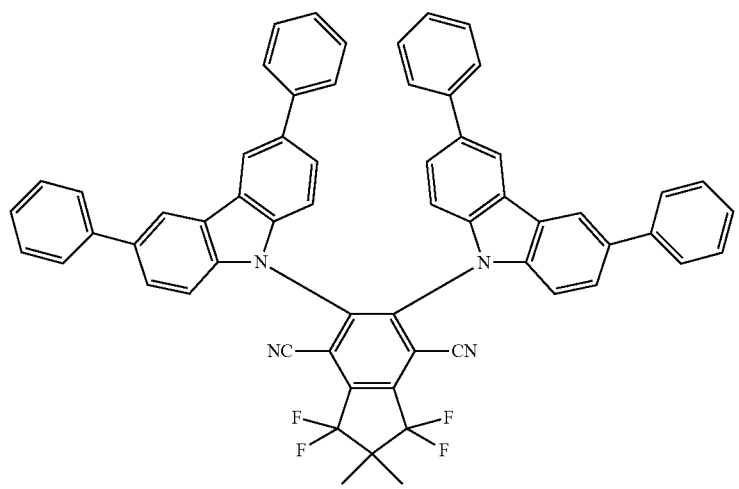
(I-202)
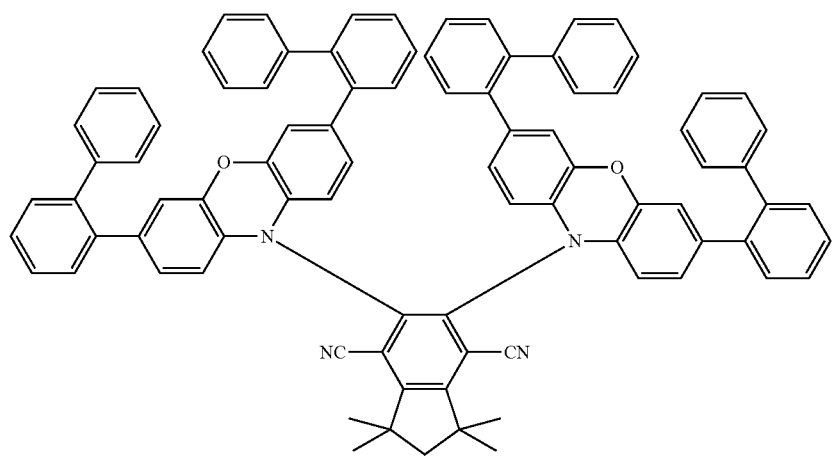
(I-203)

-continued
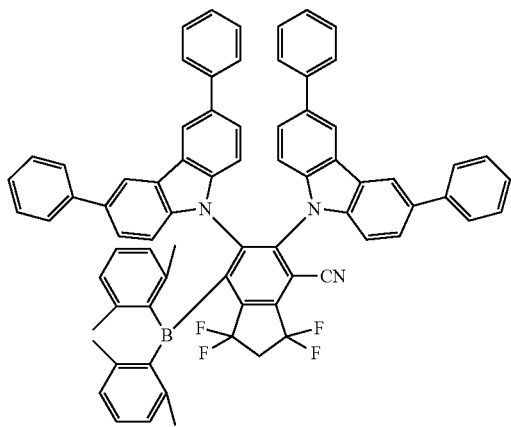
(I-204)
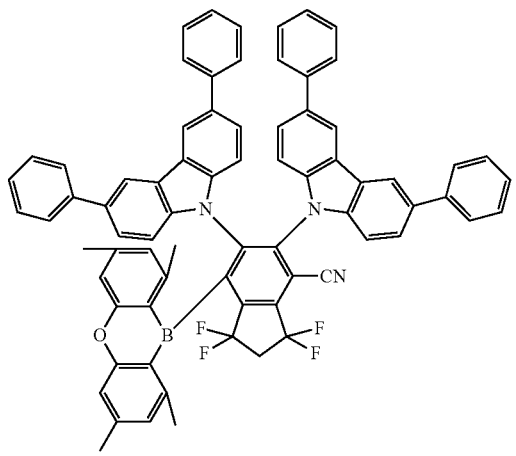
(I-205)
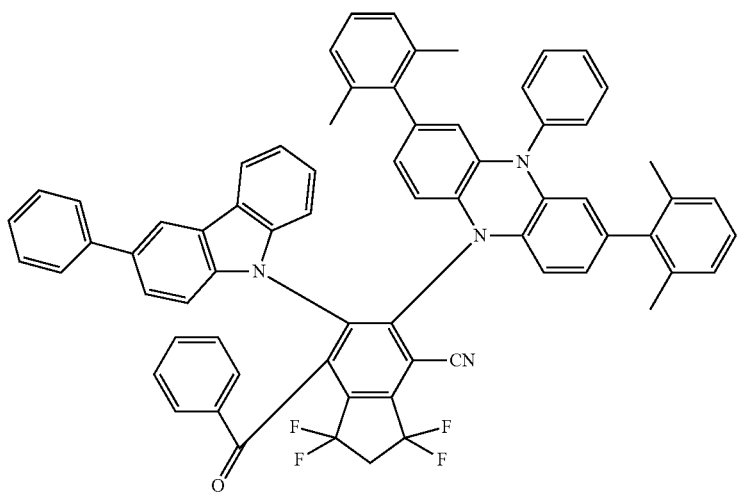
(I-206)
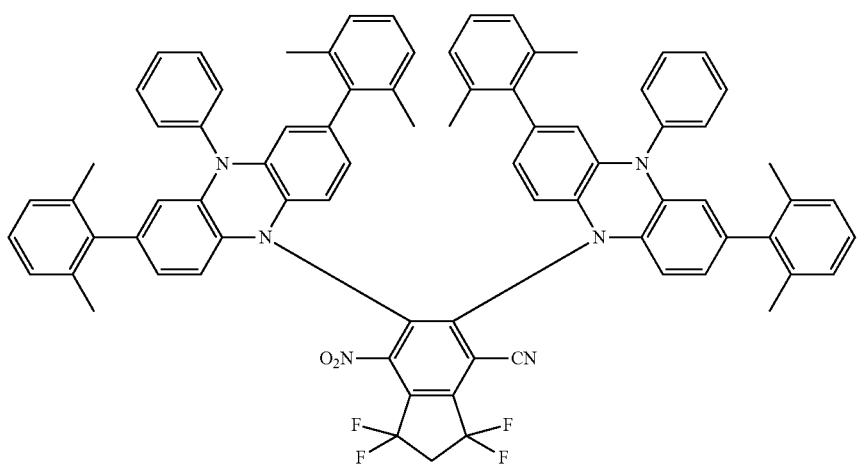
(I-207)

(I-208)
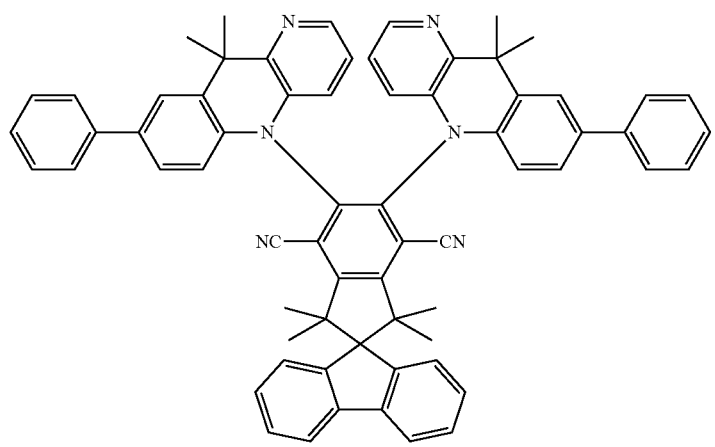
(I-209)
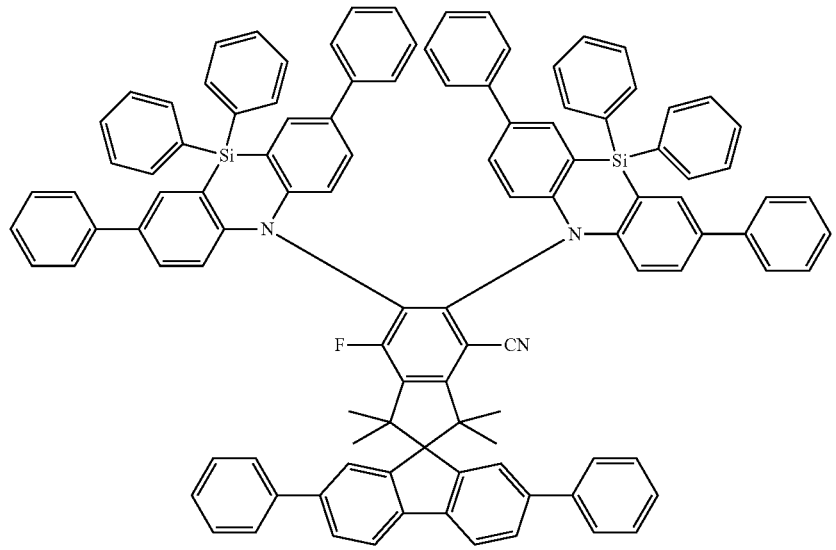
(I-210)
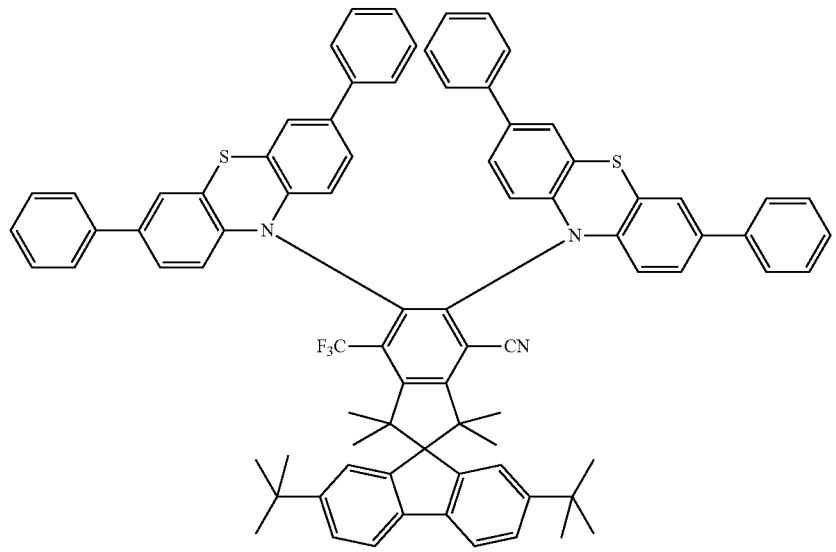

(I-211)
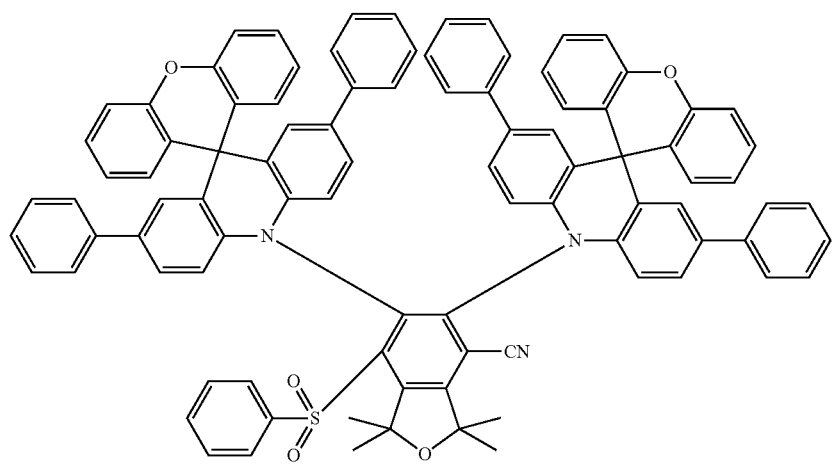
(I-212)
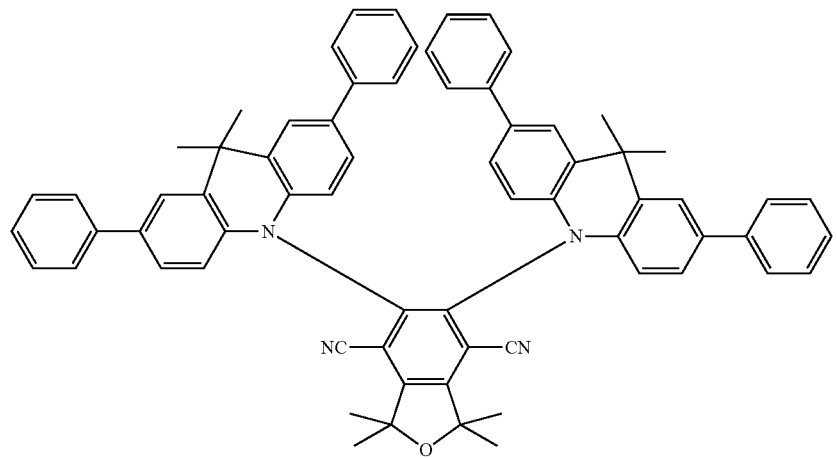
(I-213)
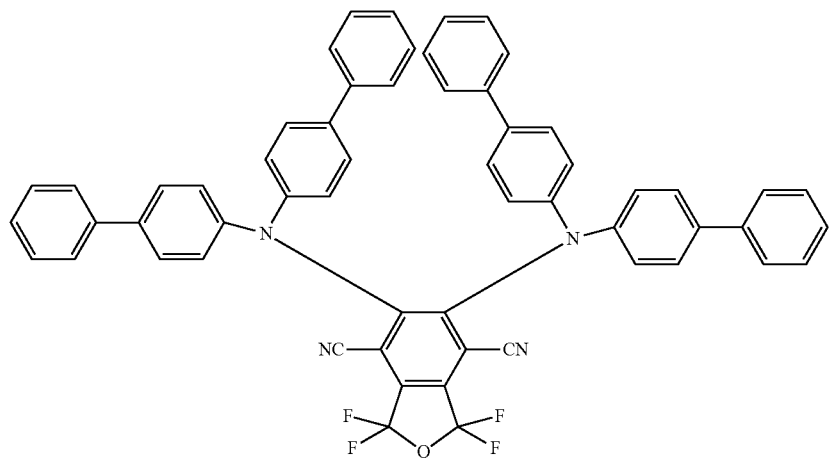

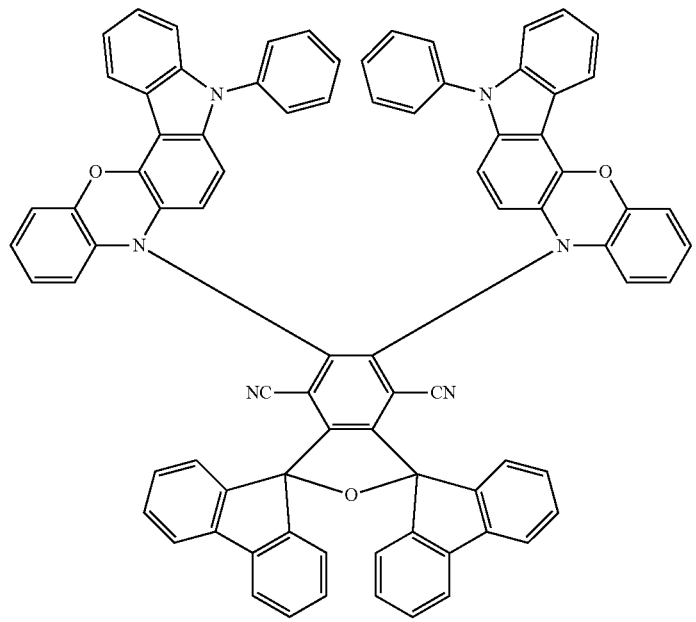
(I-214)
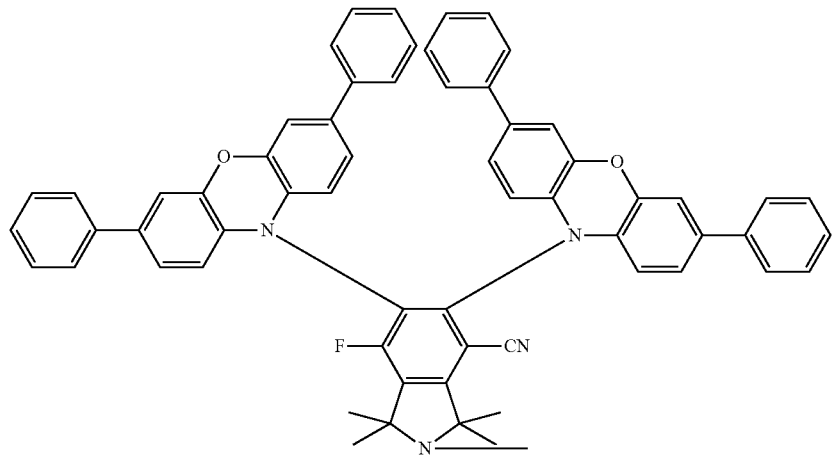
(I-215)
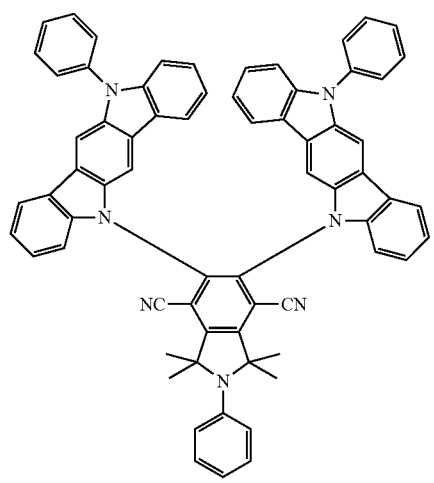
(I-216)
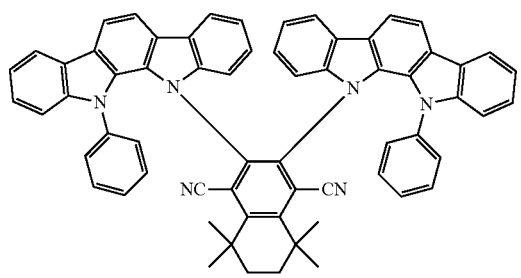
(I-217)

-continued
(I-218)
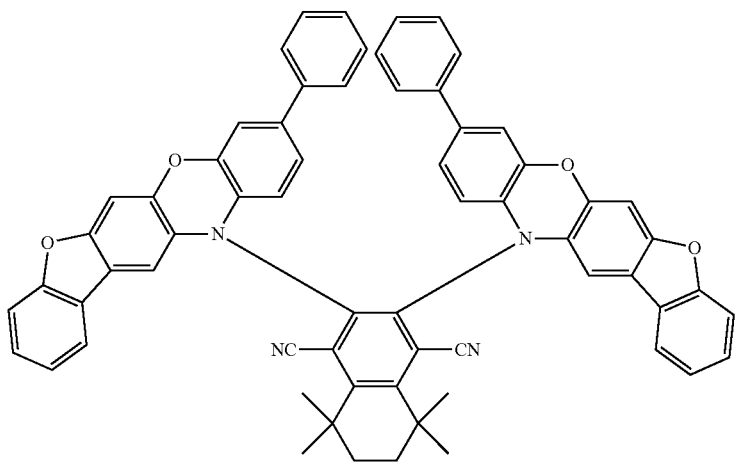
(I-219)
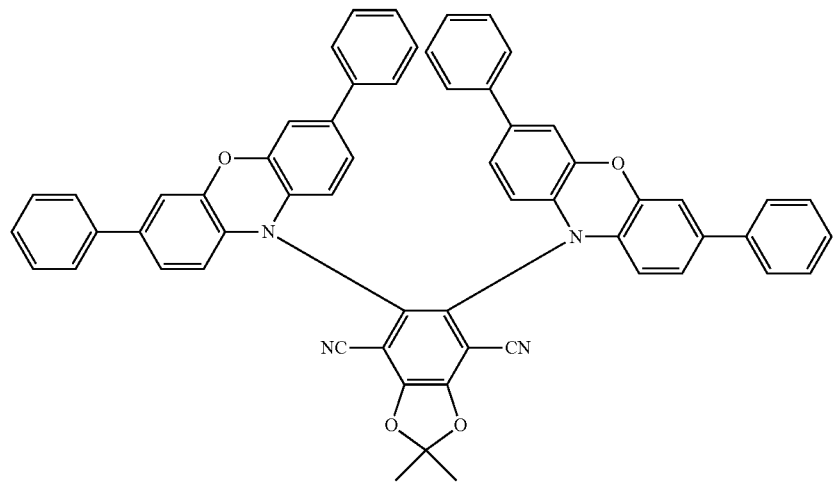
(I-220)
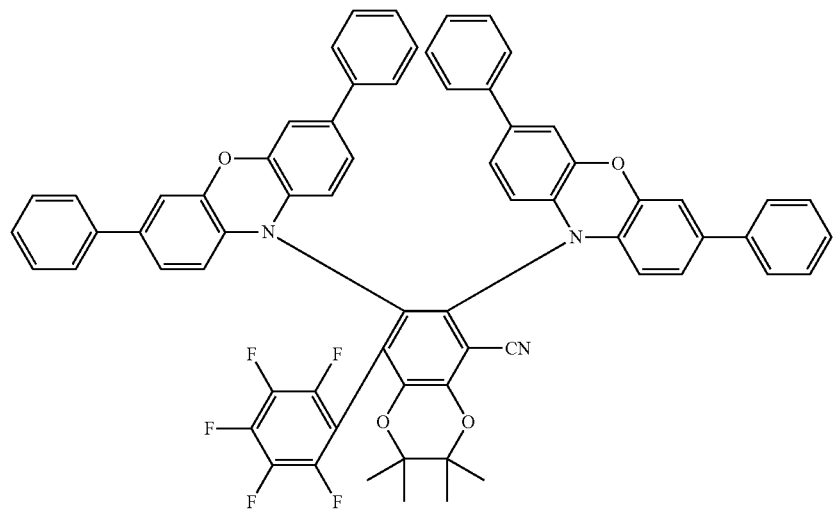

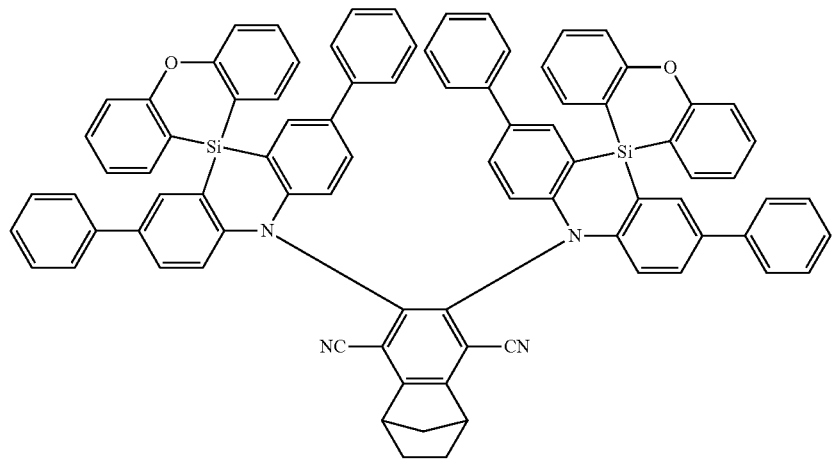
(I-221)
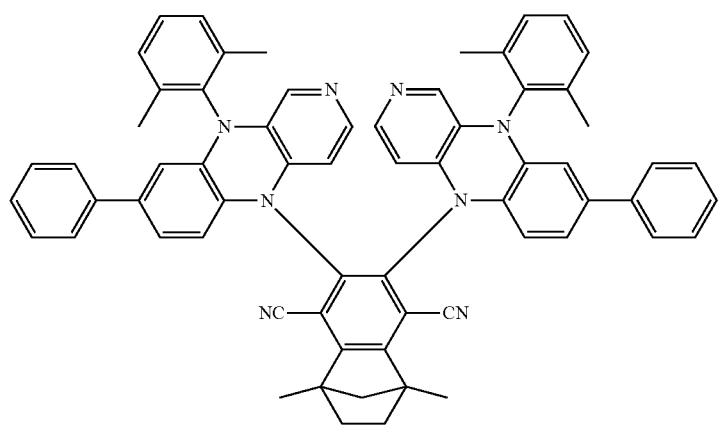
(I-222)
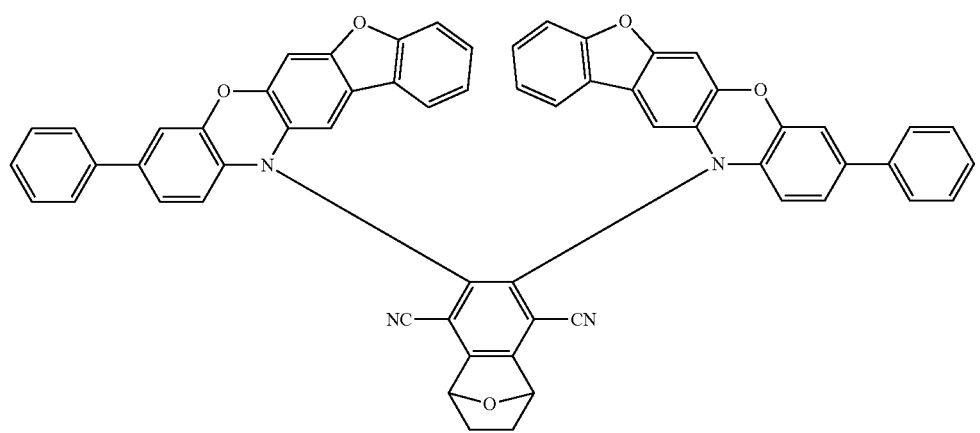
(I-223)

-continued
(I-224)
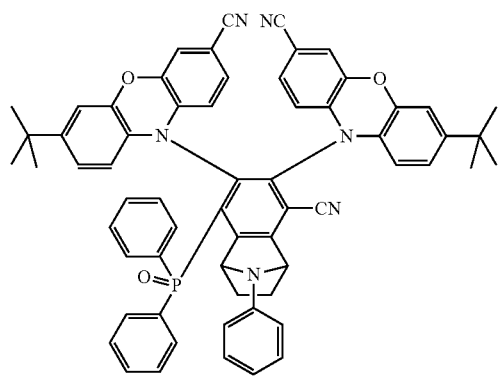
(I-225)
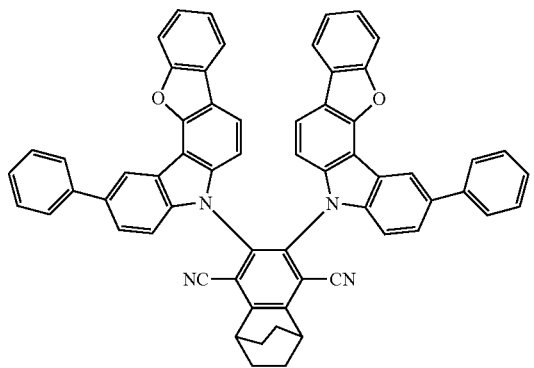
(I-226)
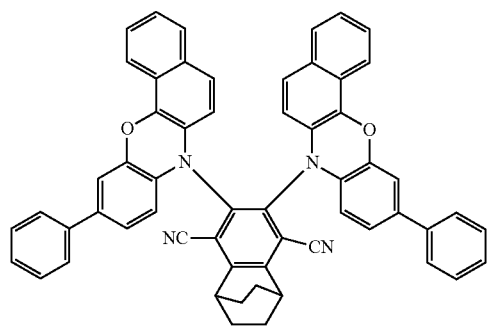
(I-227)
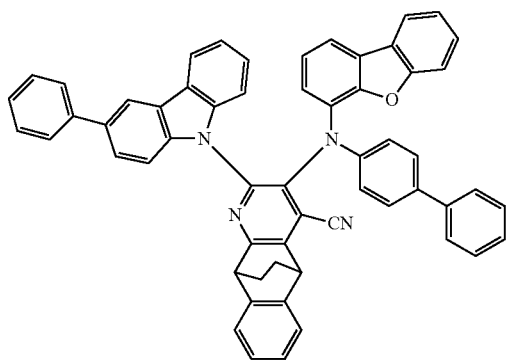
(I-228)
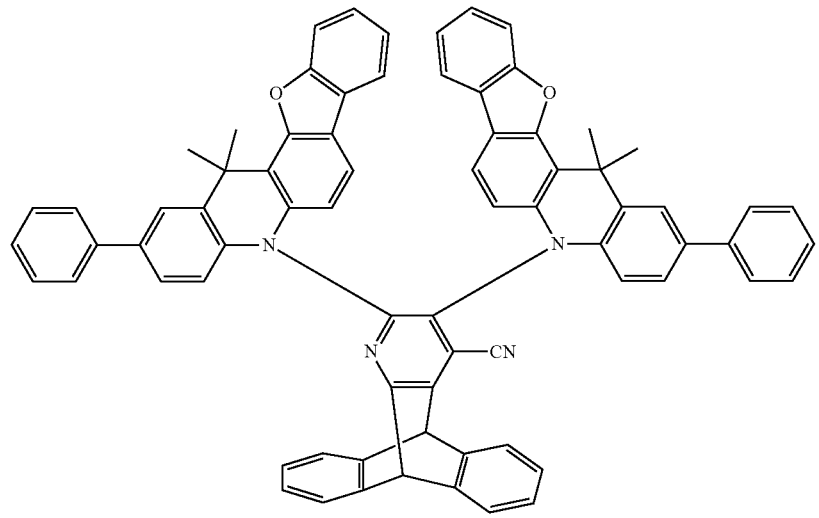

(I-229) 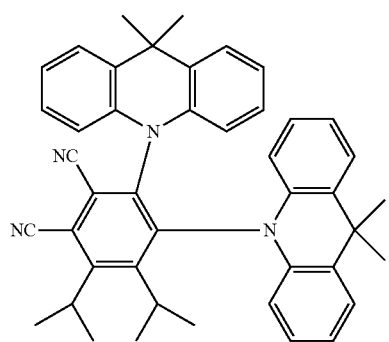
(I-230) 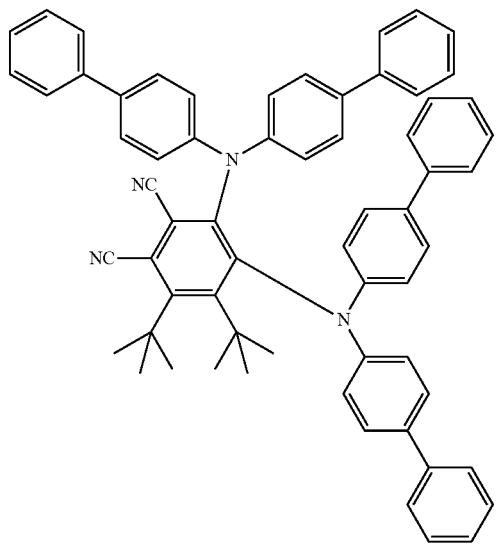
(I-231) 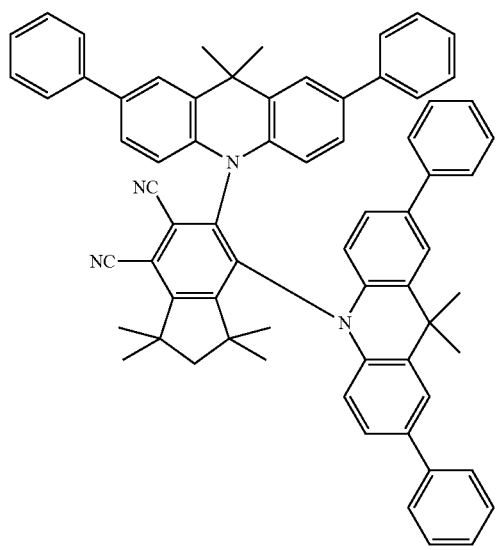
(I-232) 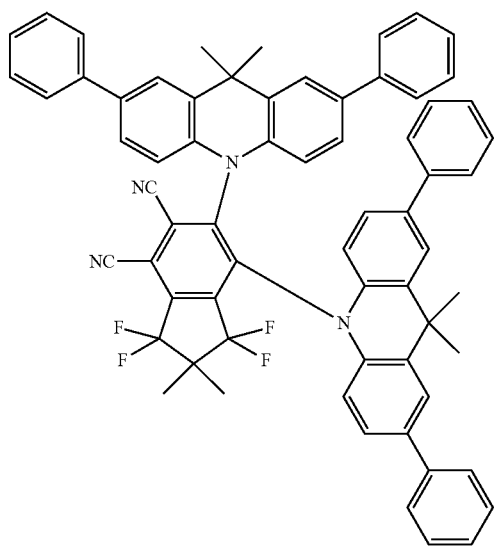
(I-233) 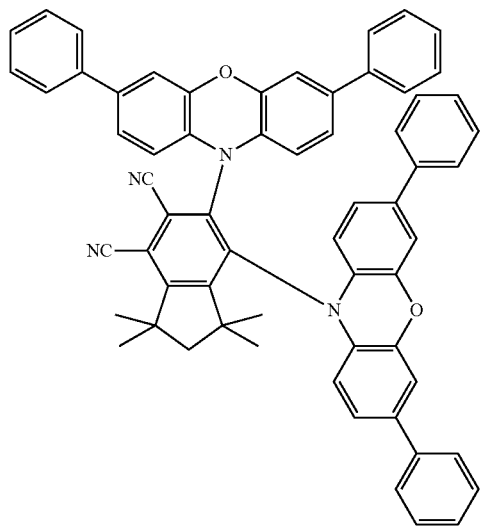
(I-234) 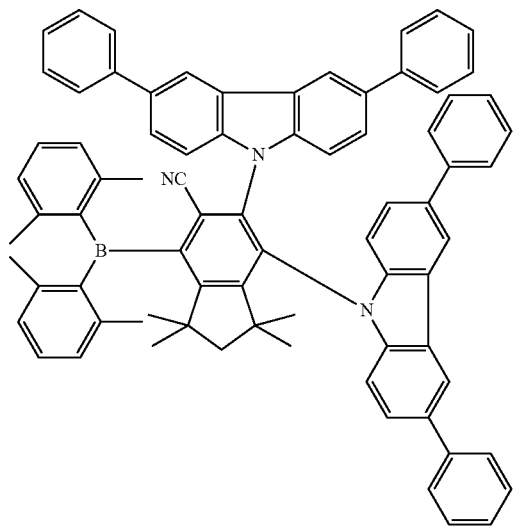

-continued
(I-235)
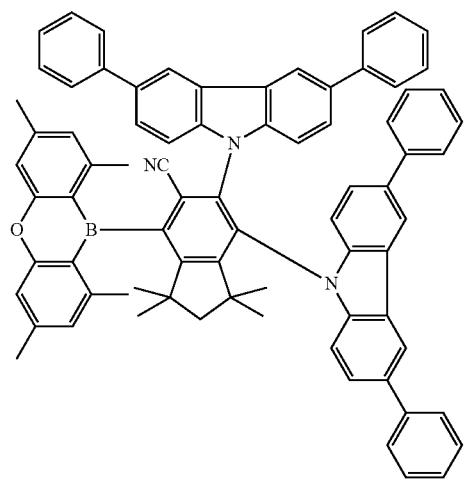
(I-236)
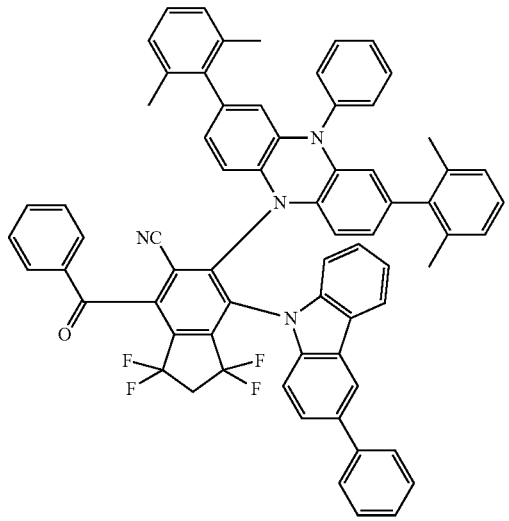
(I-237)
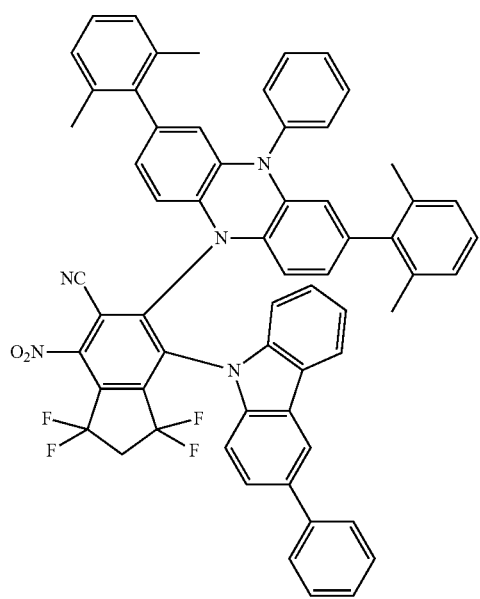
(I-238)
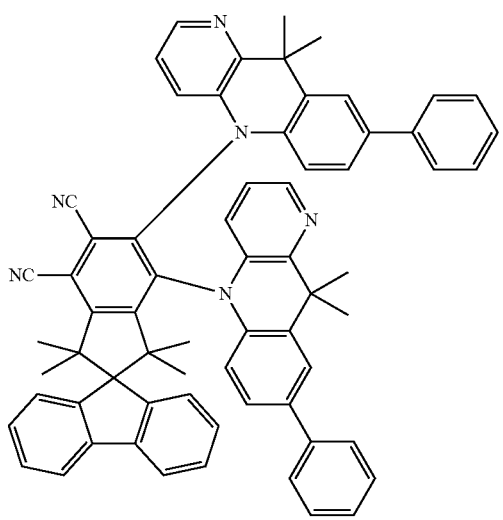

-continued
(I-239)
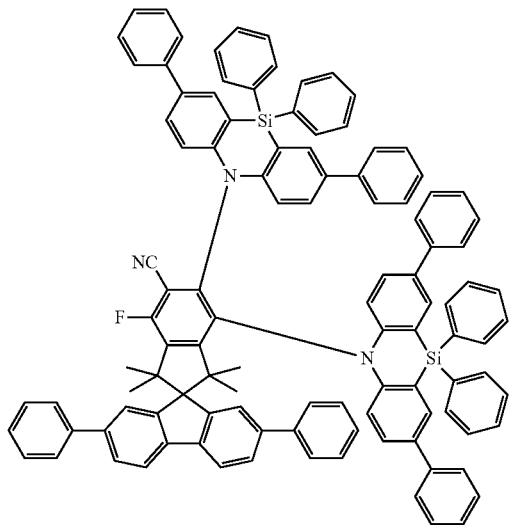
(I-240)
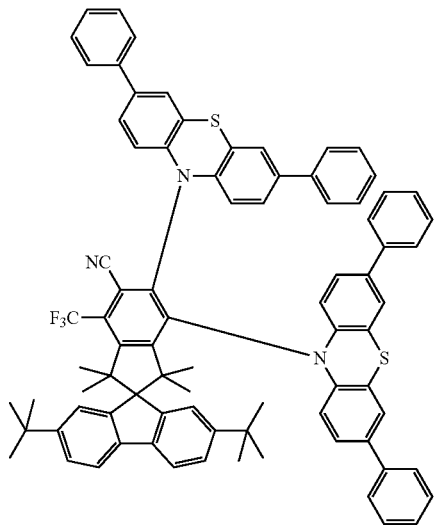
(I-241)
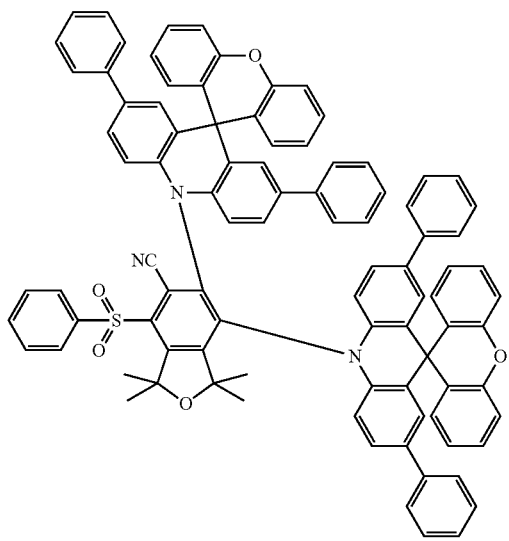
(I-242)
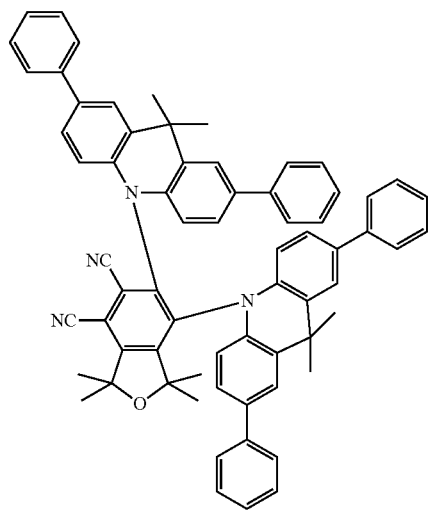

-continued
(I-243)
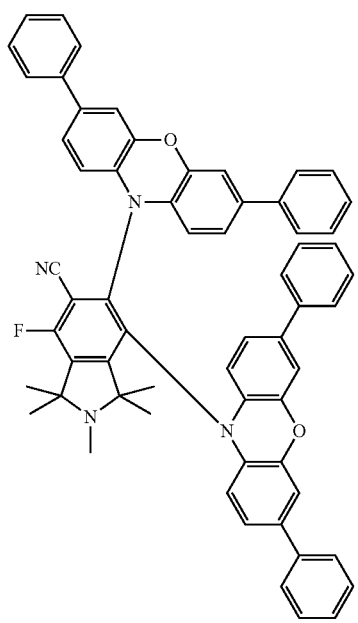
(I-244)
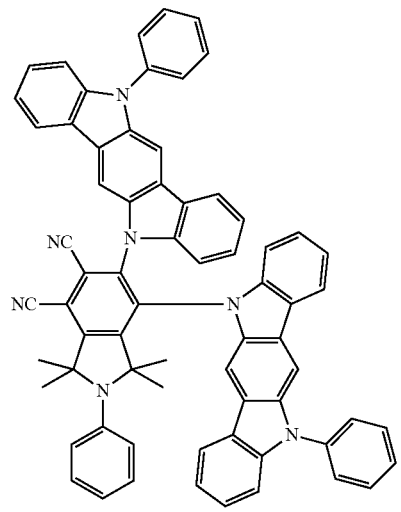
(I-245)
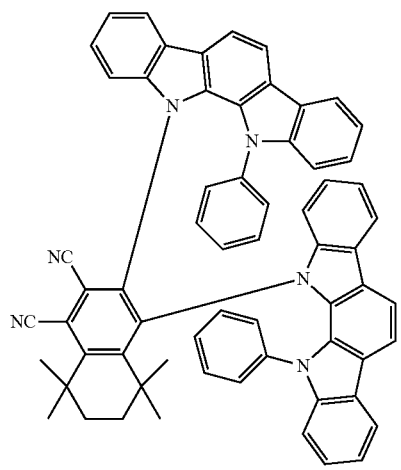
(I-246)
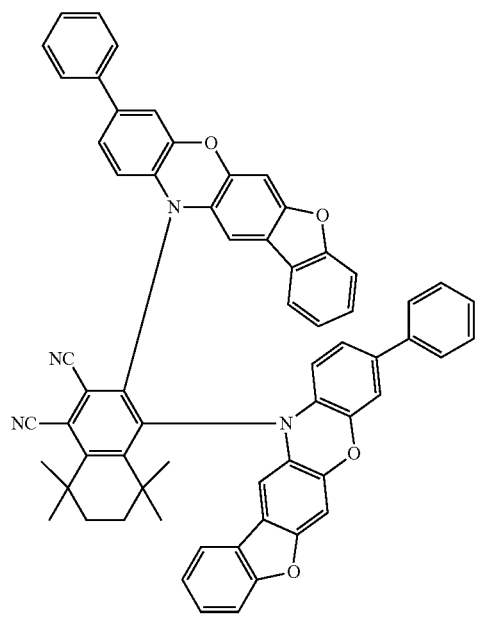

-continued
(I-247)
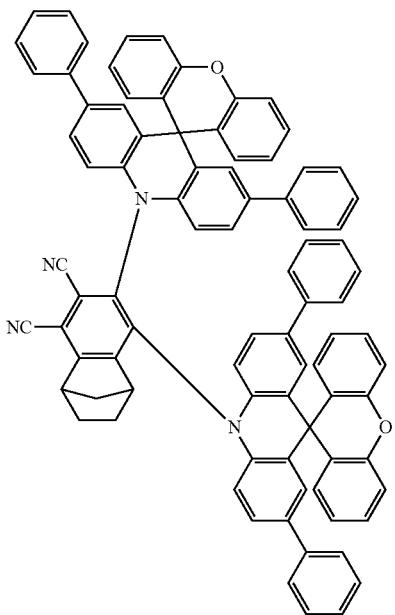
(I-248)
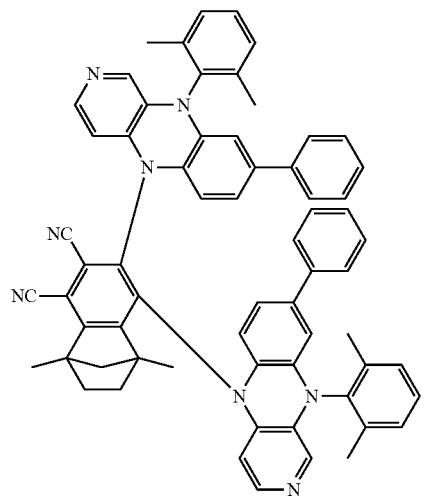
(I-249)
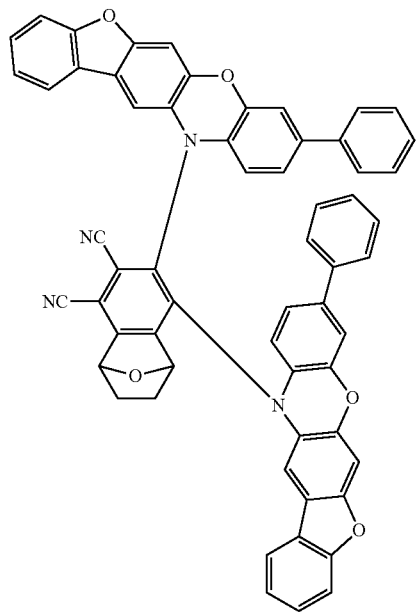
(I-250)
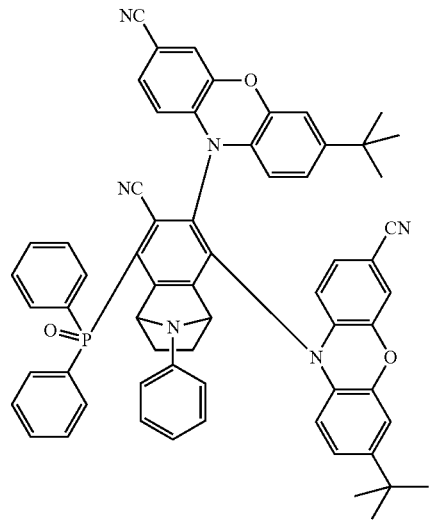

-continued
(I-251)
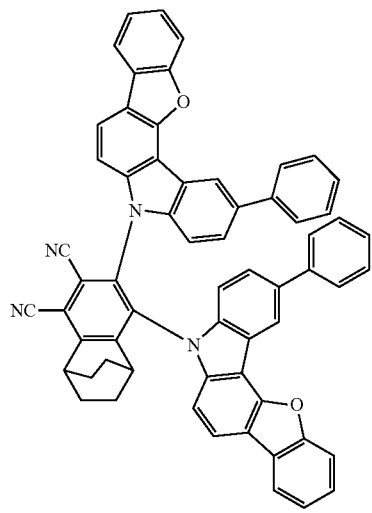
(I-252)
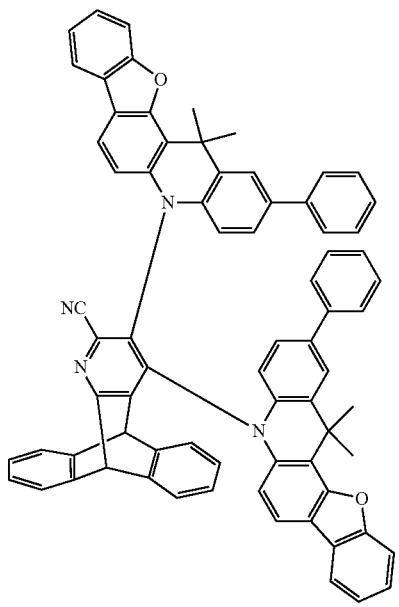
(I-253)
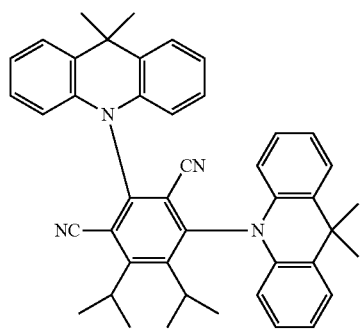
(I-254)
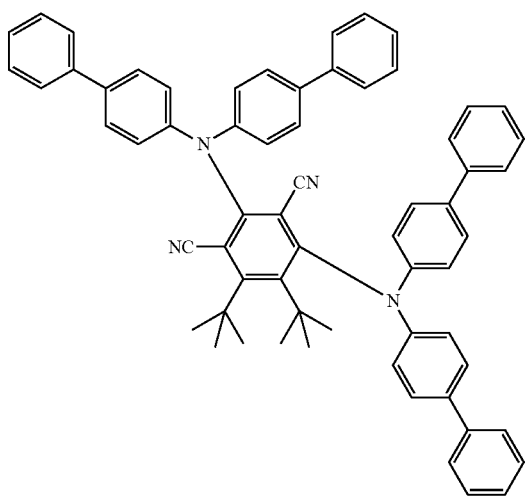
(I-255)
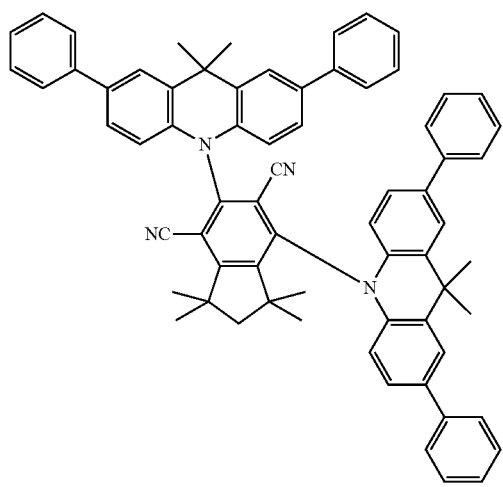
(I-256)
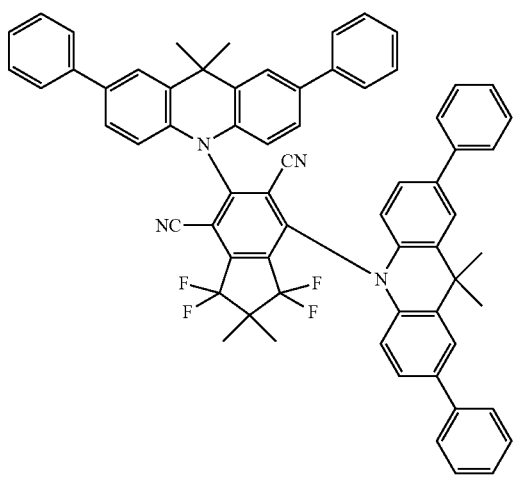

-continued
(I-257)
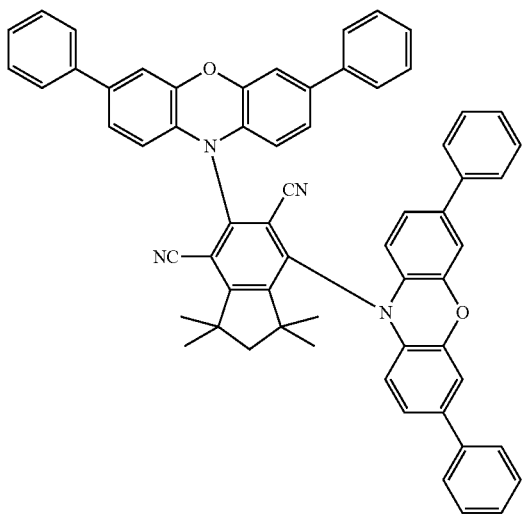
(I-258)
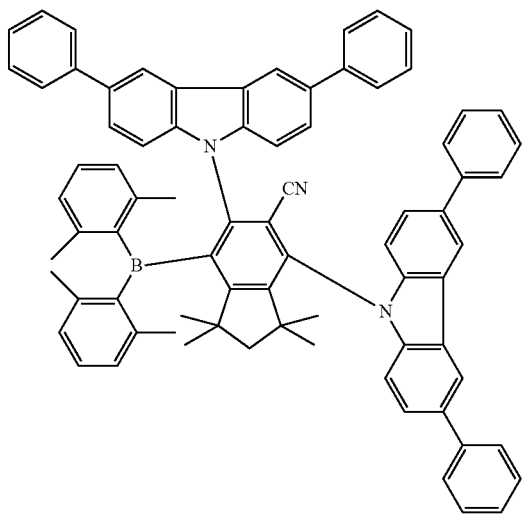
(I-259)
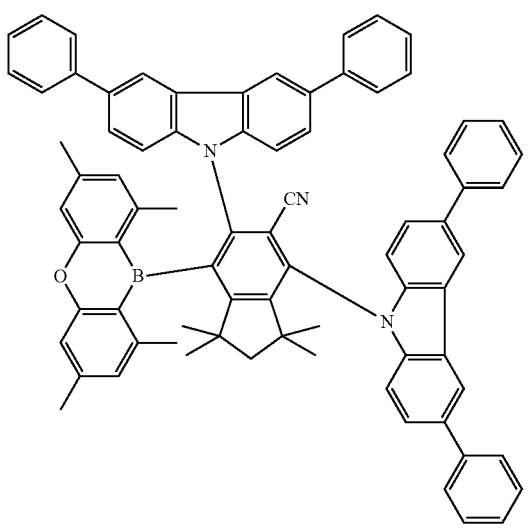
(I-260)
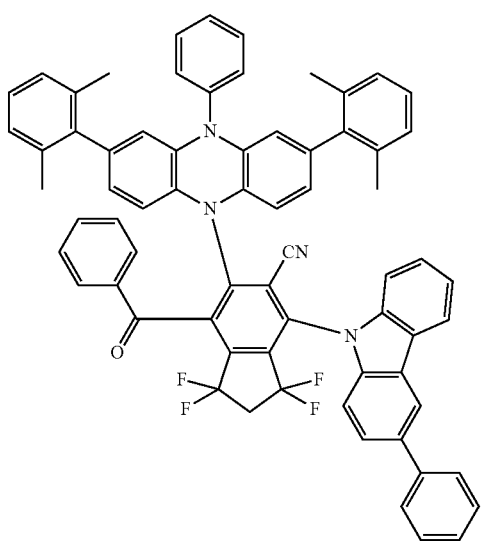
(I-261)
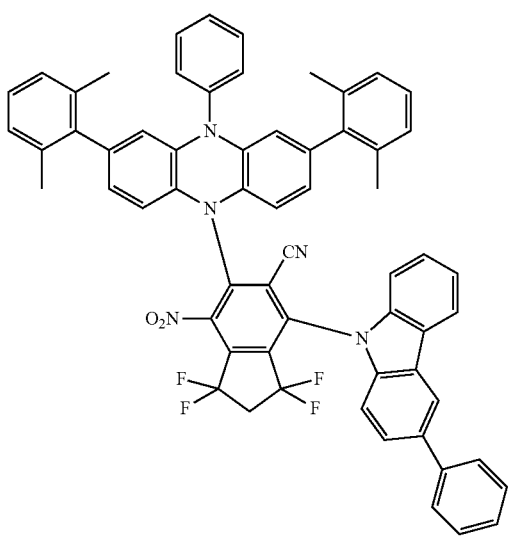
(I-262)
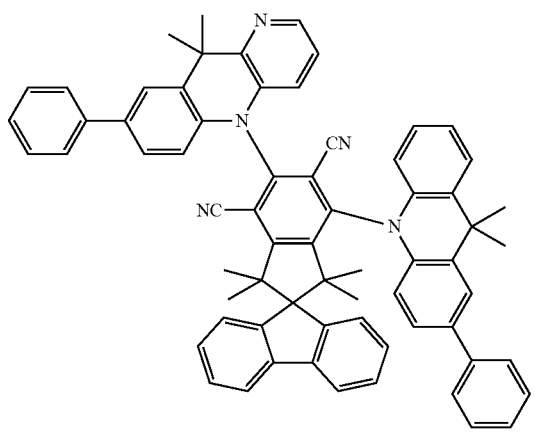

-continued
(I-263)
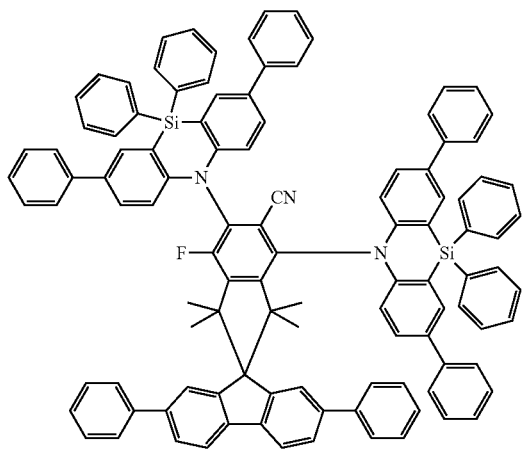
(I-264)
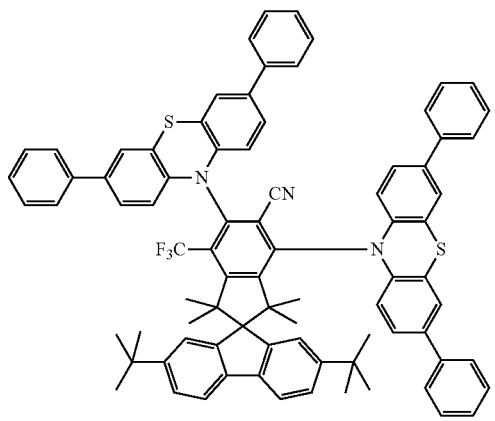
(I-265)
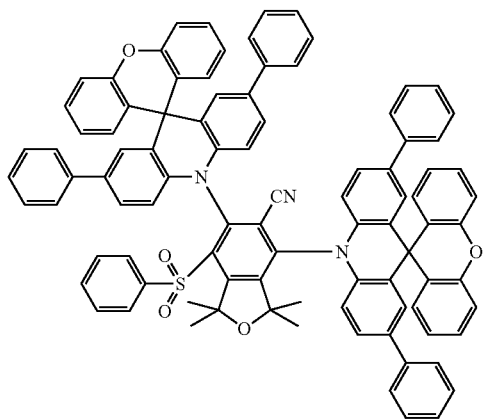
(I-266)
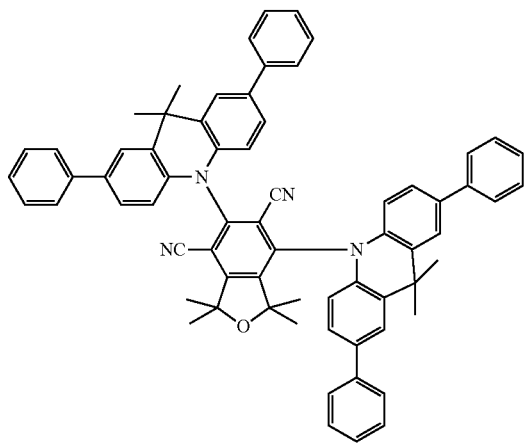
(I-267)
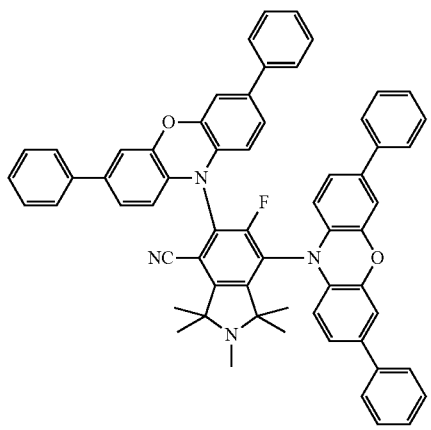
(I-268)
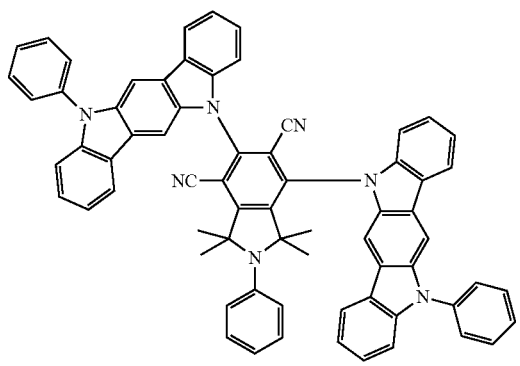

(I-269)
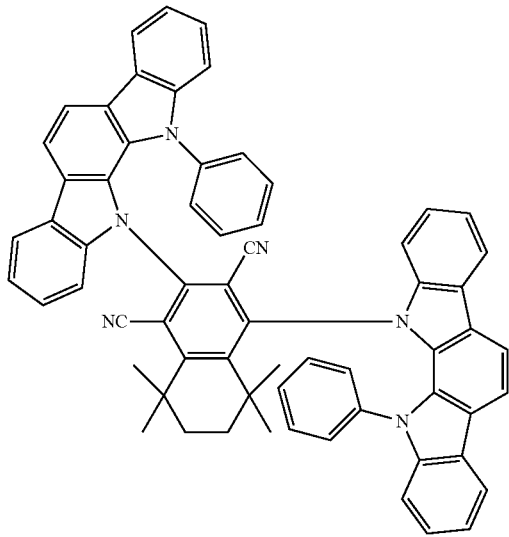
(I-270)
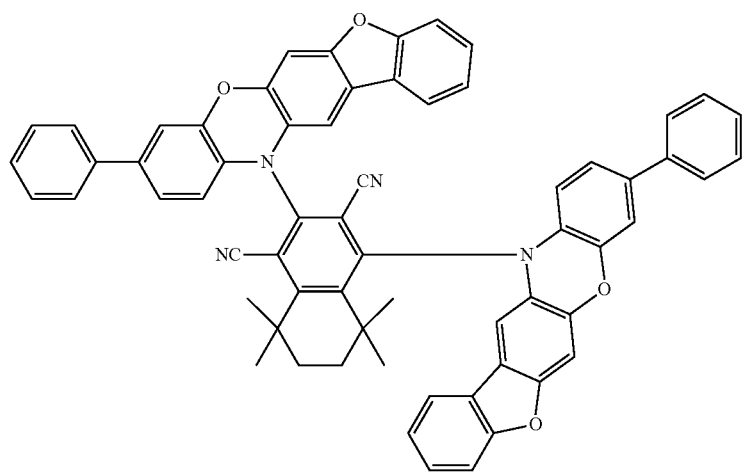
(I-271)
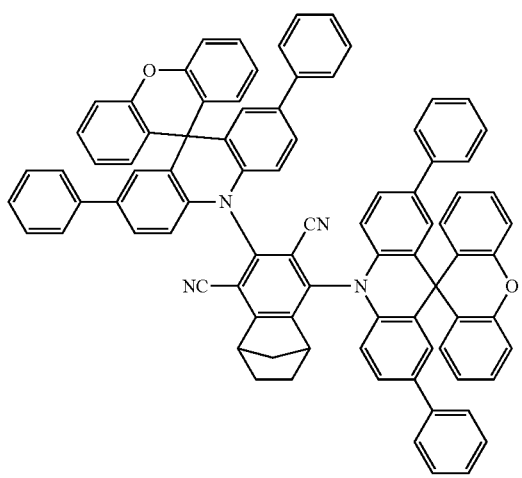
(I-272)
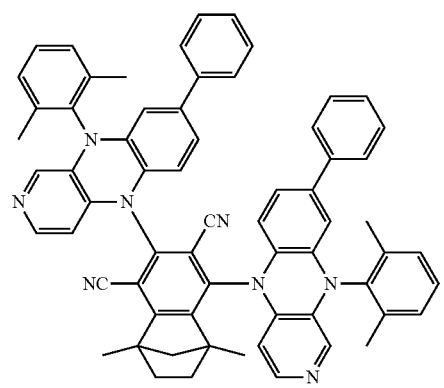

-continued
(I-273)
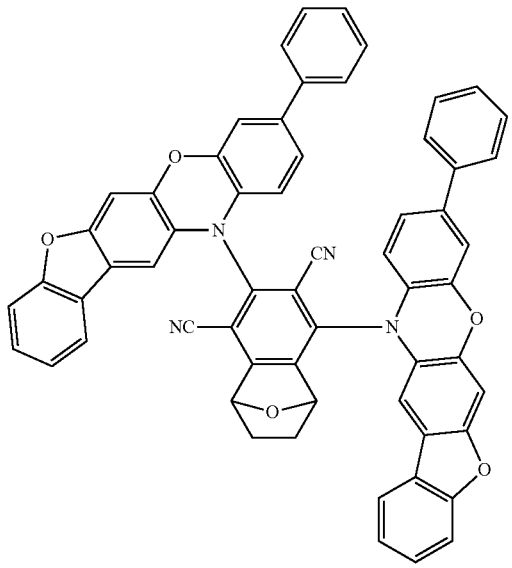
(I-274)
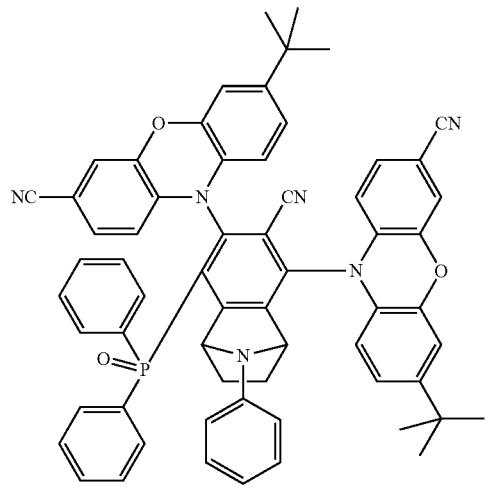
(I-275)
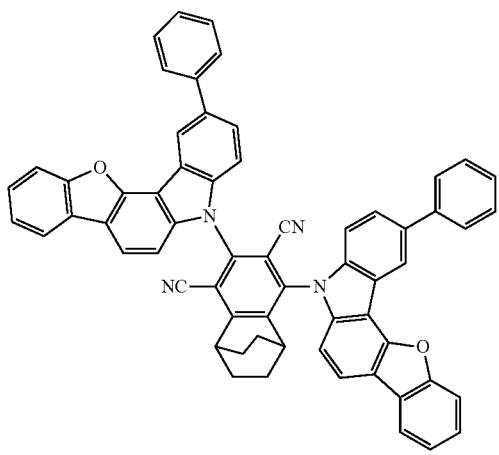
(I-276)
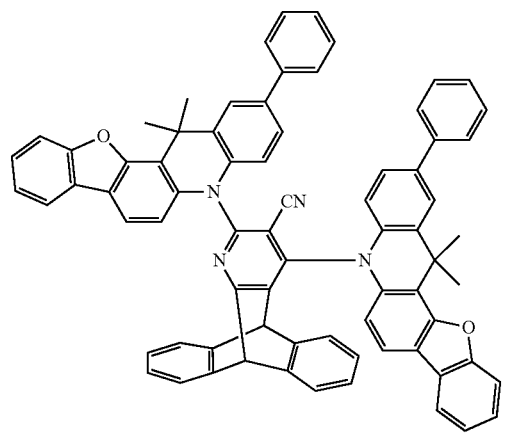
(I-277)
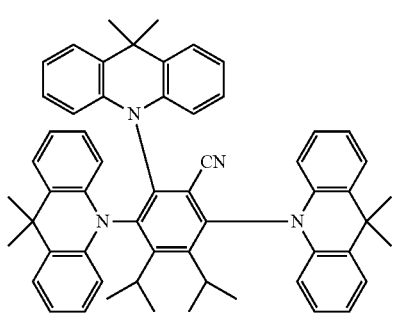
(I-278)
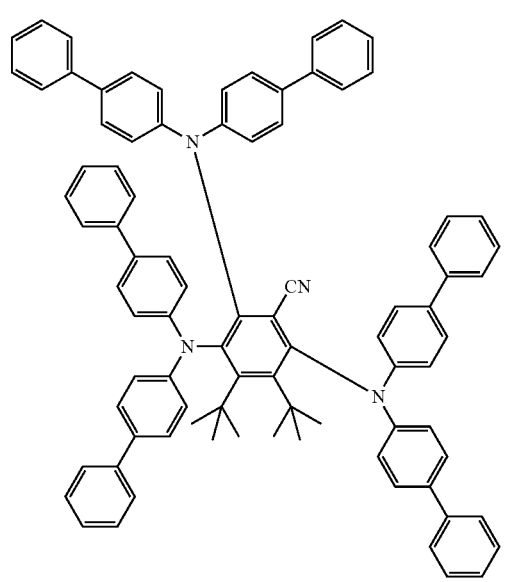

-continued
(I-279)
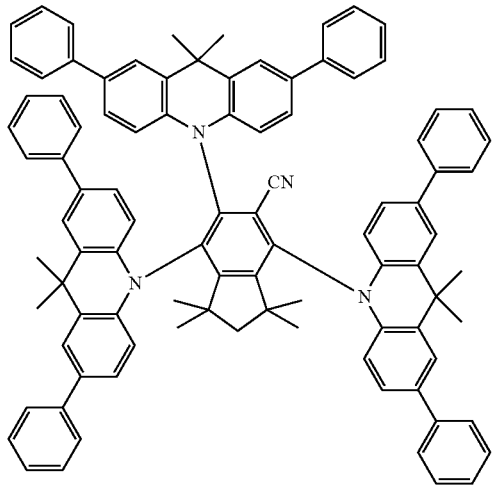
(I-280)
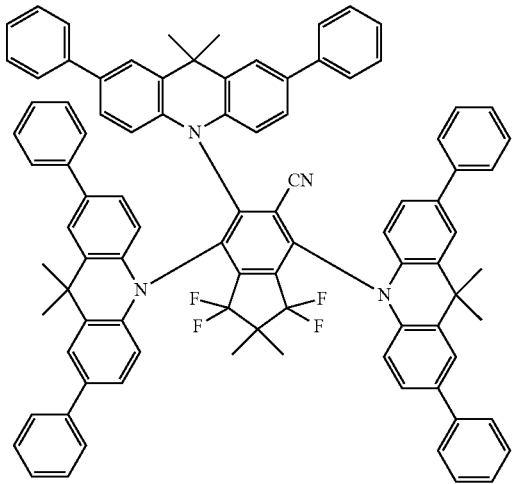
(I-281)
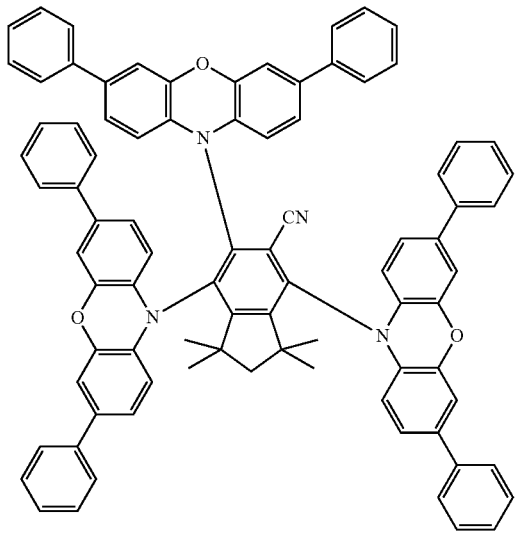
(I-282)
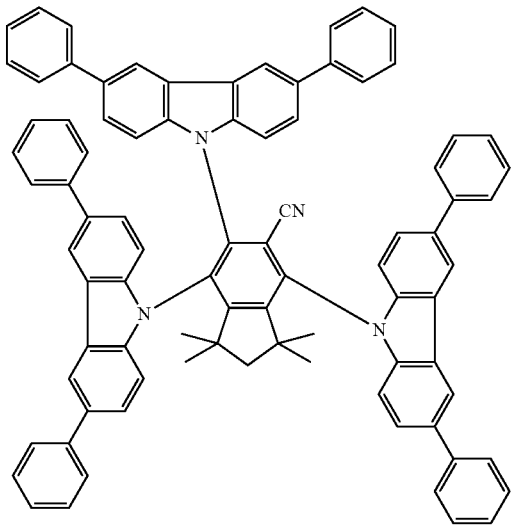
(I-283)
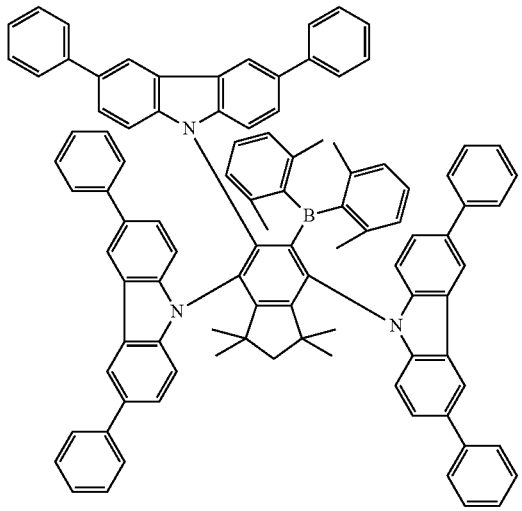
(I-284)
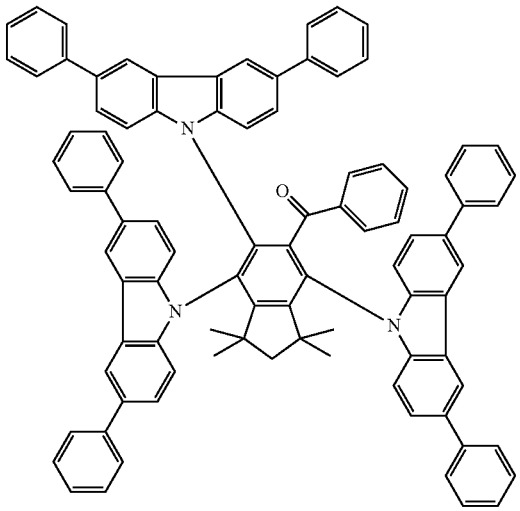

-continued
(I-285)
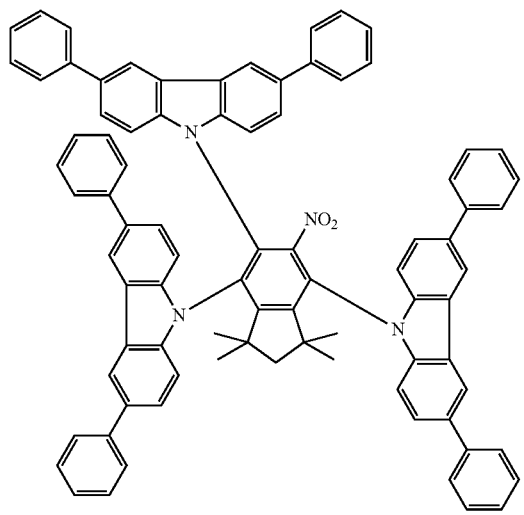
(I-286)
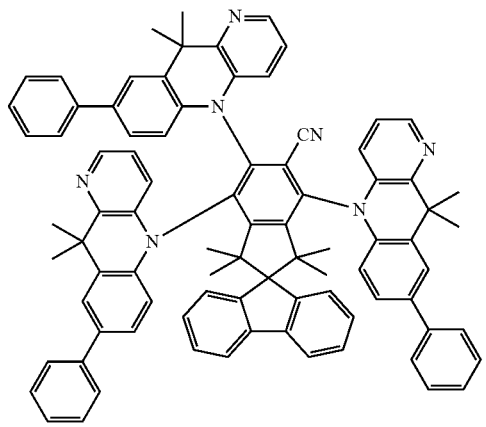
(I-287)
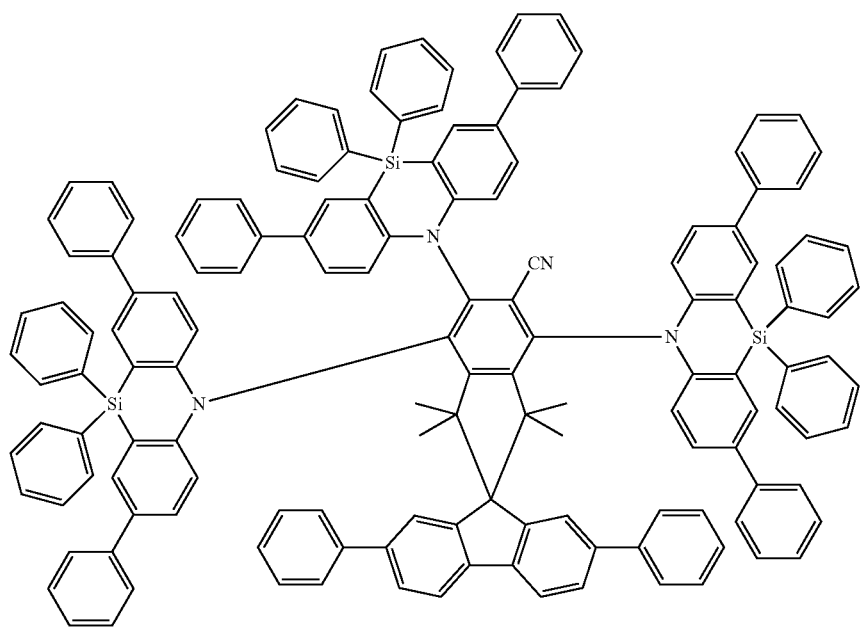

-continued
(I-288)
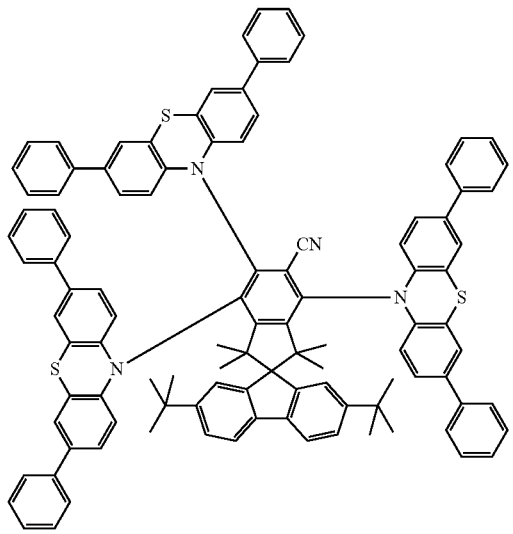
(I-289)
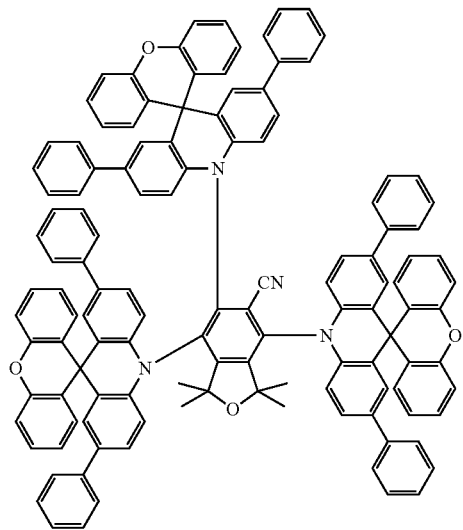
(I-290)
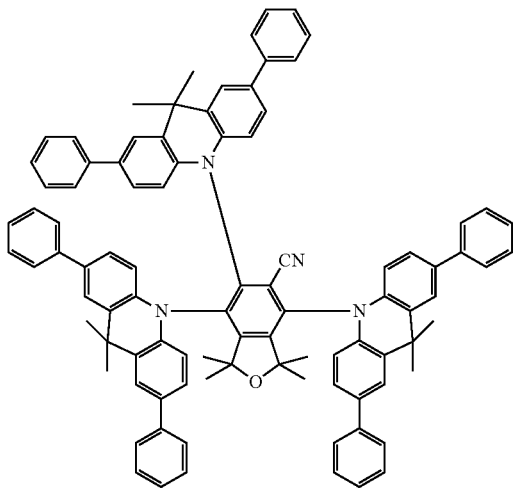
(I-291)
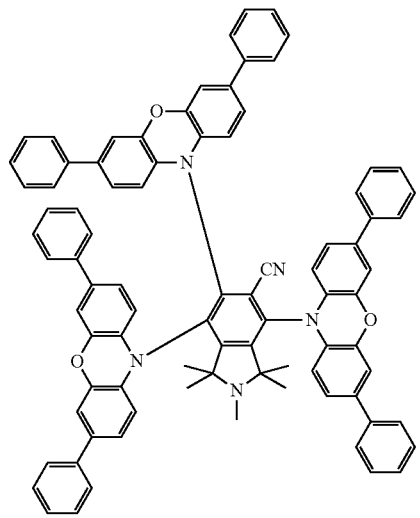

-continued
(I-292)
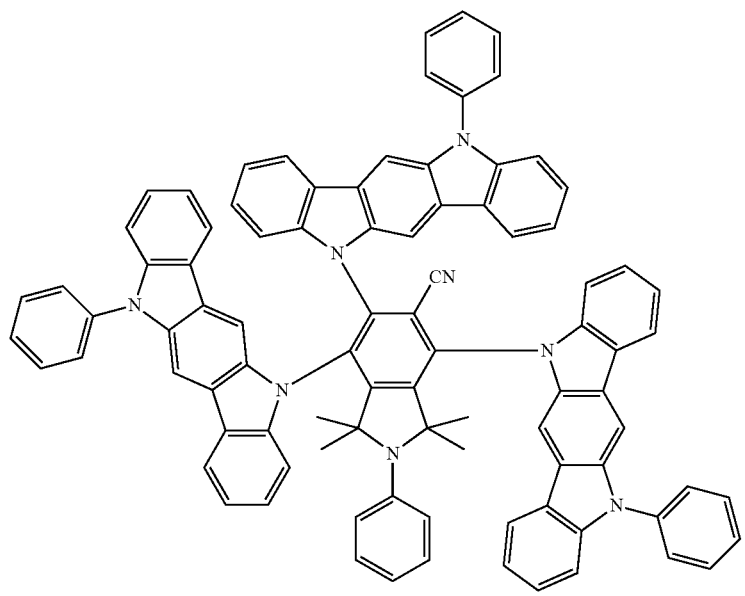
(I-293)
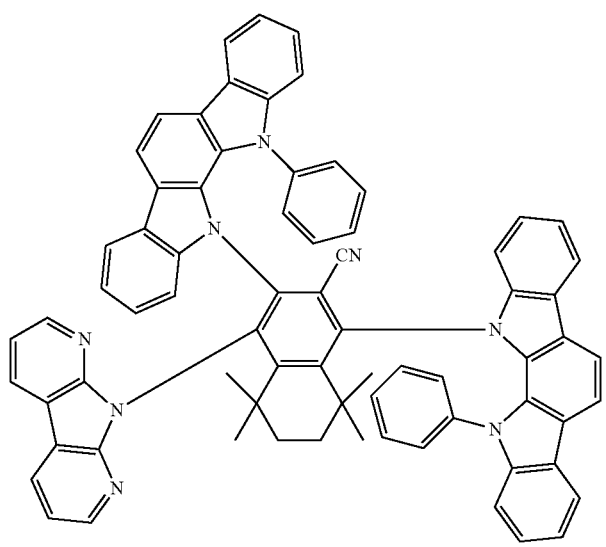
(I-294)
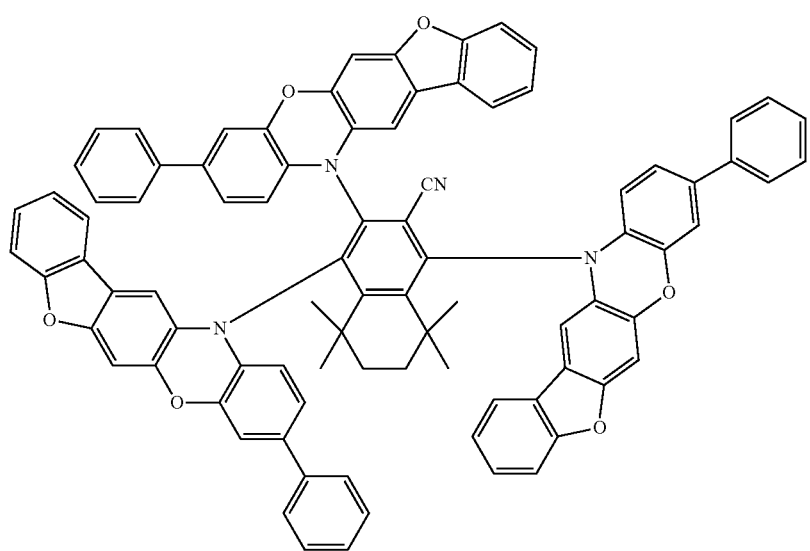

-continued
(I-295)
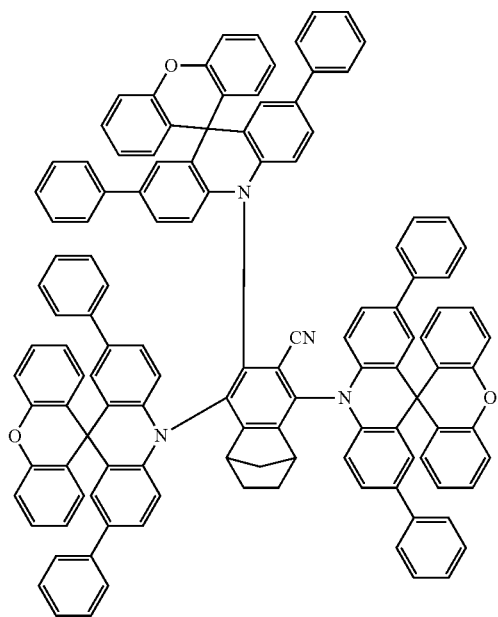
(I-296)
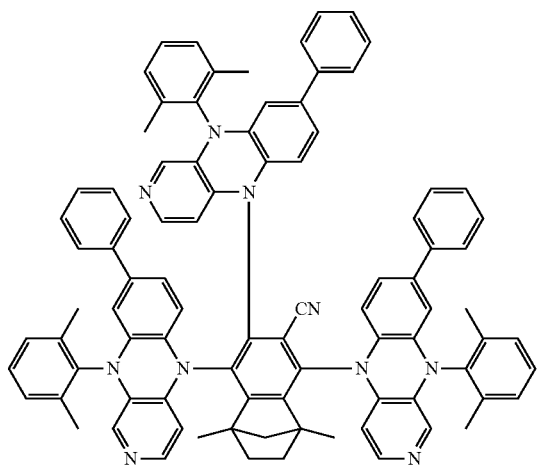
(I-297)
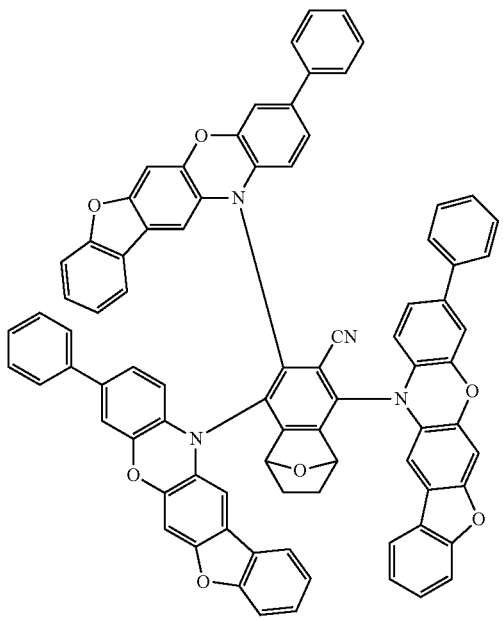
(I-298)
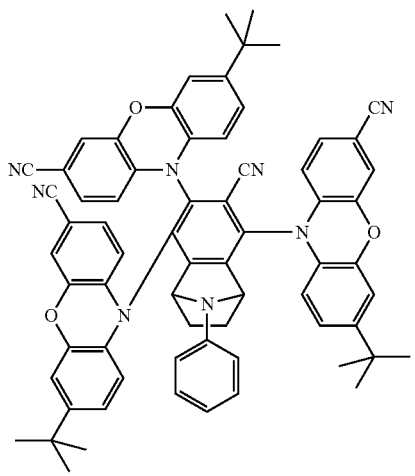

-continued
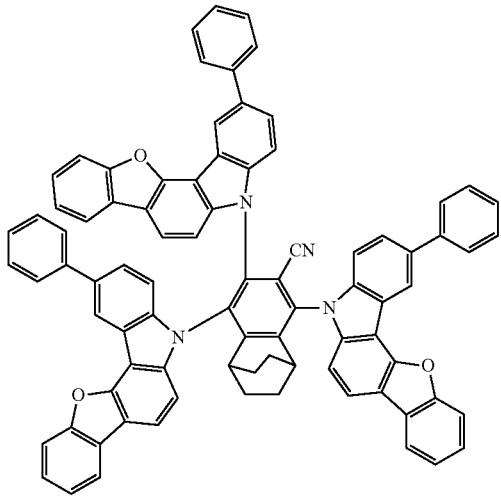
(I-299)
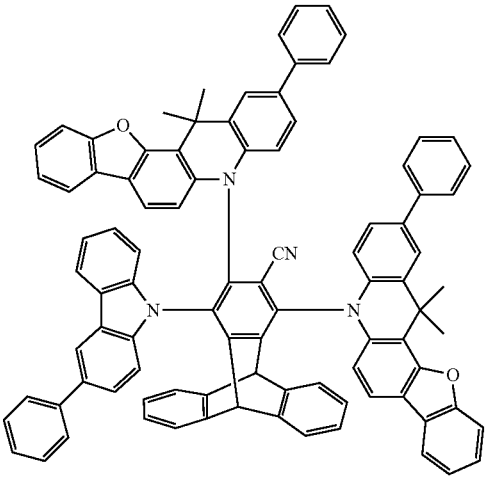
(I-300)
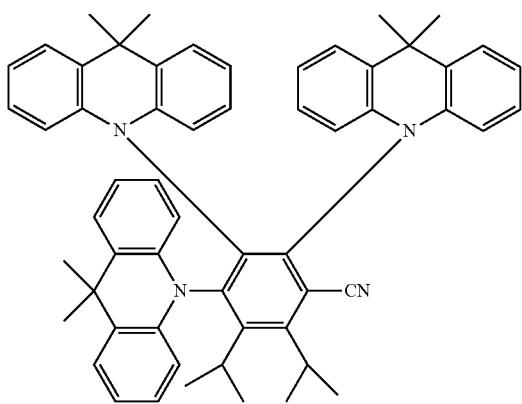
(I-301)
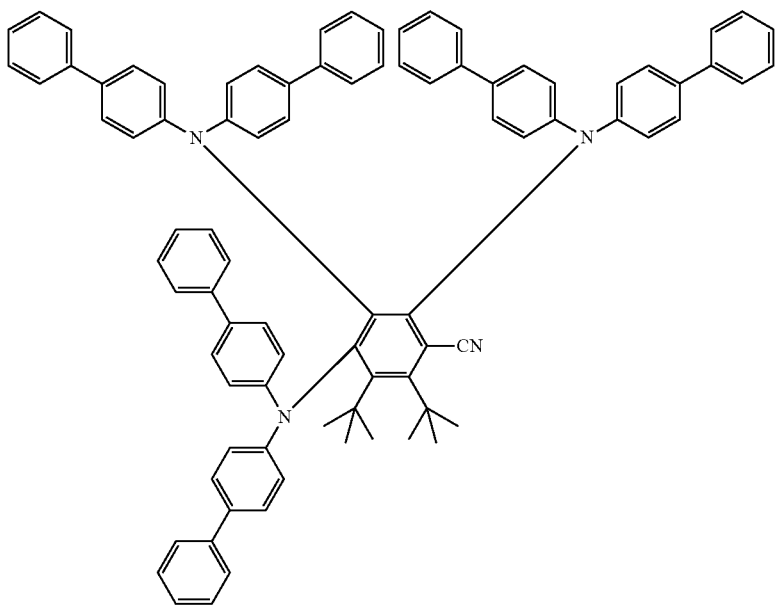
(I-302)

-continued
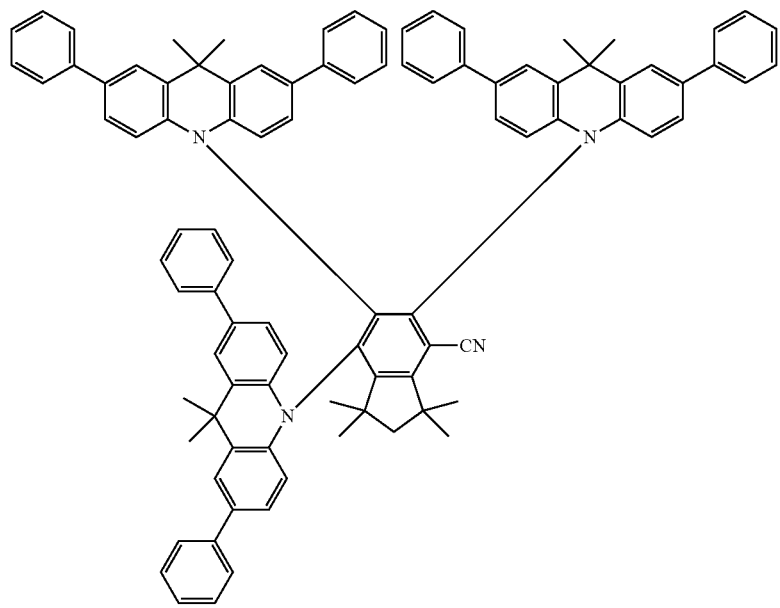
(I-303)
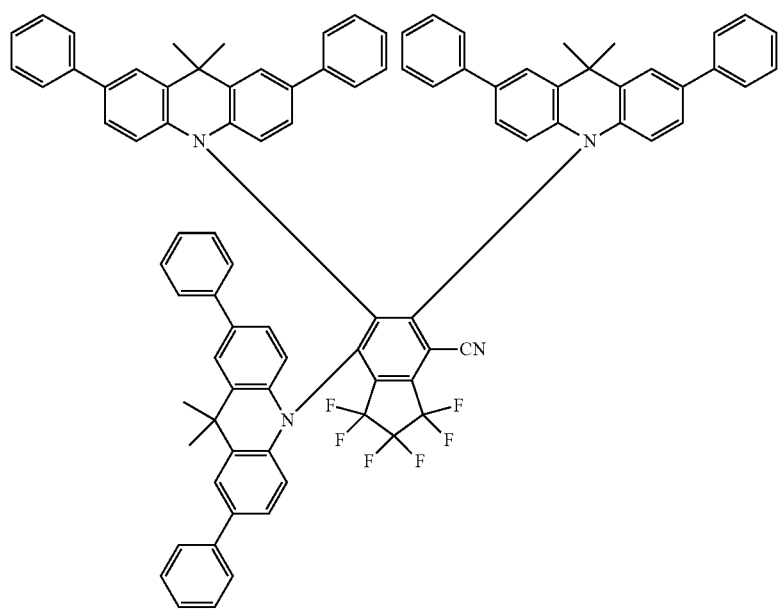
(I-304)

-continued
(I-305)
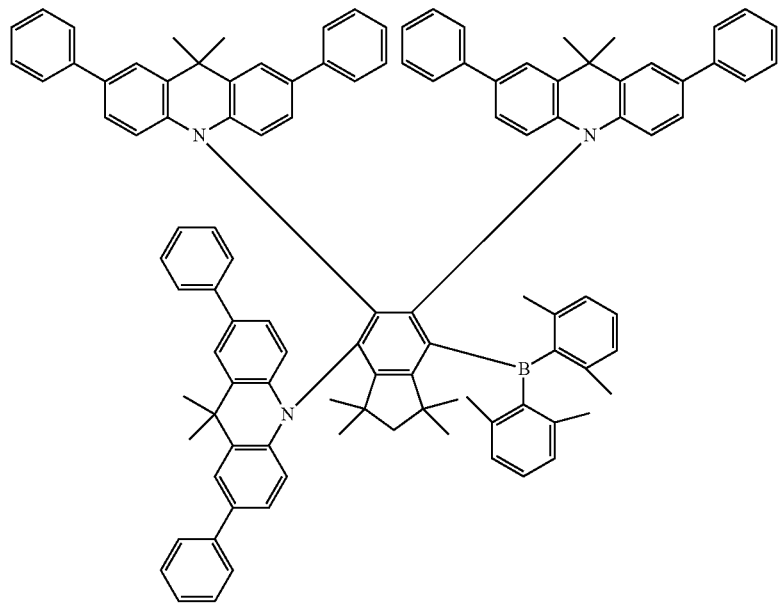
(I-306)
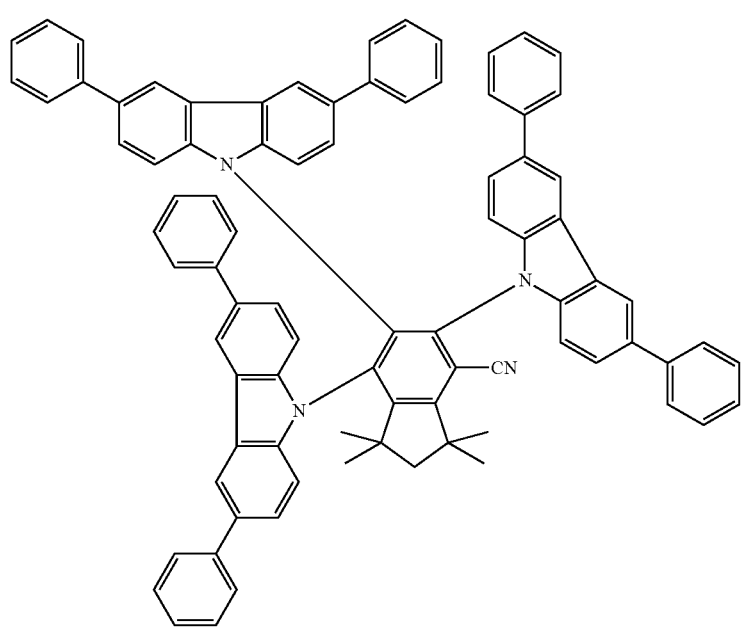

-continued
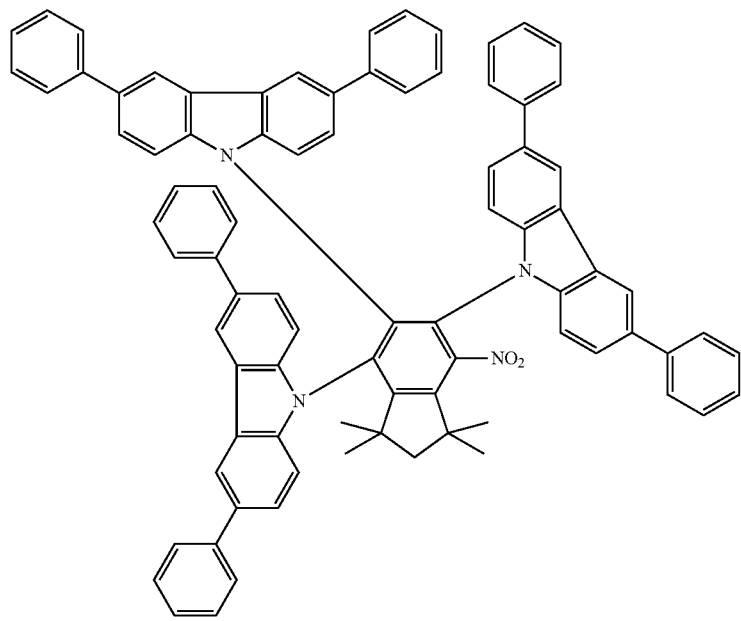
(I-307)
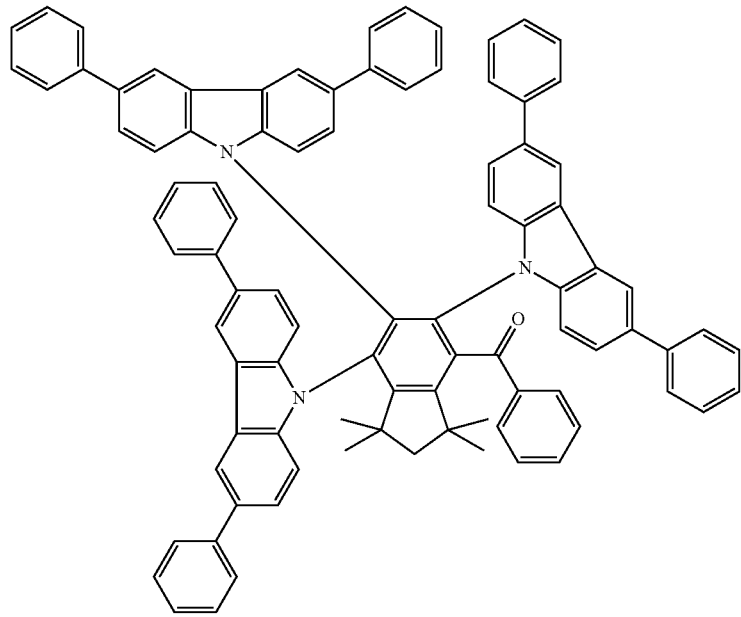
(I-308)

-continued
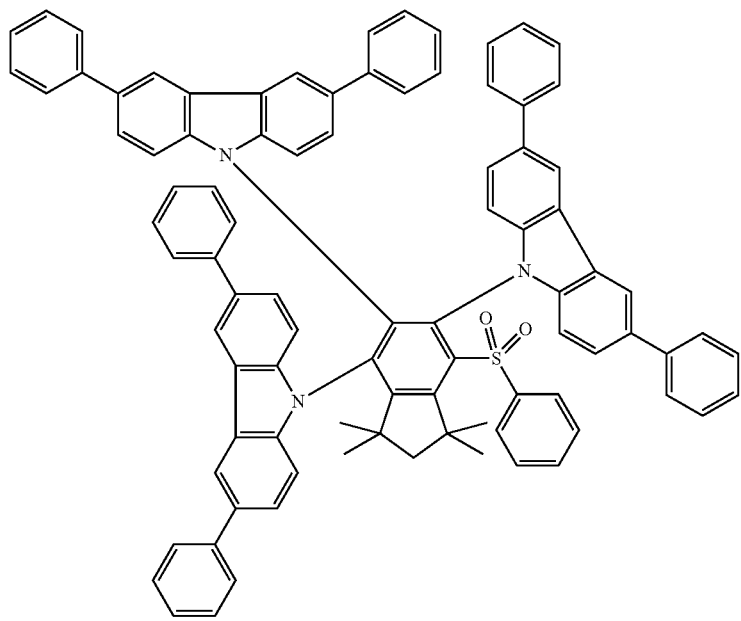
(I-309)
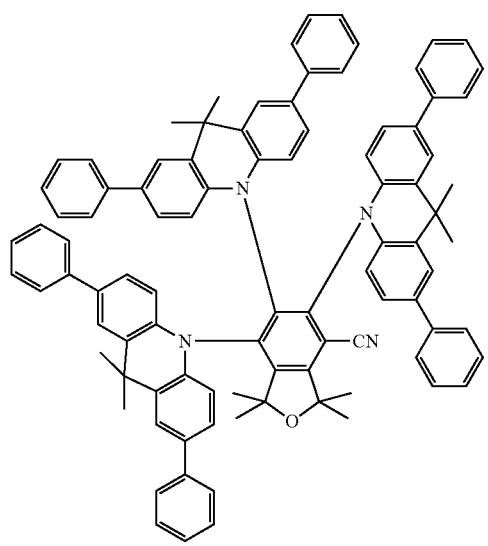
(I-310)
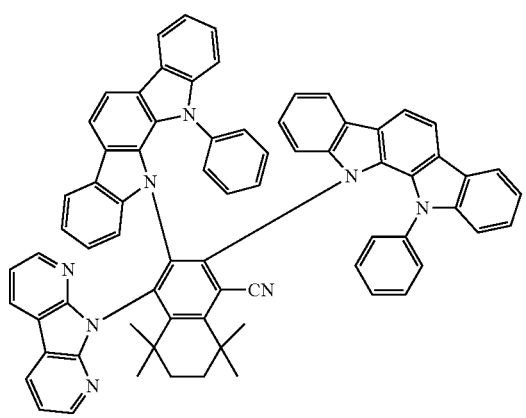
(I-311)

(I-312)

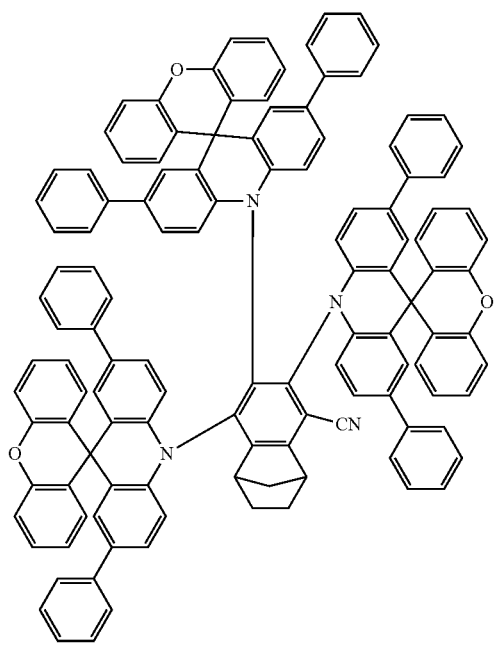

(I-313)

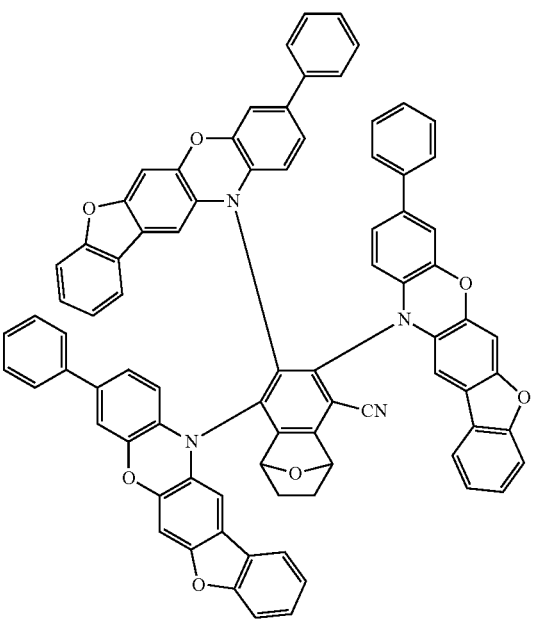

(I-314)

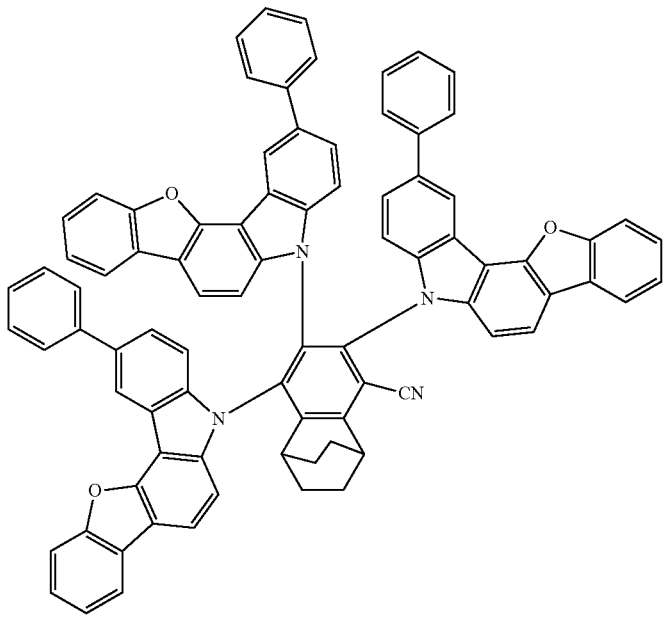

Oligomers, Polymers, Dendrimers

The compounds of general formula (I), particularly such compounds comprising reactive groups, may be used as monomers for the production of the respective oligomers, polymers or dendrimers. The present invention therefore also provides for oligomers, polymers and dendrimers comprising the compound of general formula (I).

Exemplary reactive groups may—independently of each other if more than one such group is present—be selected from the group consisting of Cl, Br, I, boronic acid, esters of boronic acid, amines, alkenyl with terminal C—C-double bond, alkynyl with terminal C—C-triple bond, oxirane, oextane, groups capable of undergoing a cycloaddition, particularly a 1,3-dipolar cycloaddition (such as for example dienes or azides), derivatives of carbonic acids, alcohols and silanes. Such reactive groups may be comprised in the compounds of general formula (I) for example in groups $R^A$, $R^D$ and $R^S$ and/or also directly on a ring carbon atom, as for example in any one or more of groups $Q^1$, $Q^2$, $Z^1$ and $Z^2$. Depending upon the position of the reactive group(s) in the compound of formula (I), compound (I) may eventually be located in the main chain and/or in a side chain of the oligomer, polymer or dendrimer.

For the purposes of the present application an oligomer is understood to comprise at least 3 repeating units, and a polymer is understood to comprise at least 10 repeating units, such repeating units comprising at least one compound of general formula (I). It is noted that the above definitions in respect to the compound of formula (I) also apply here.

The oligomers, polymers and dendrimers of the present invention may be conjugated, partially conjugated or not conjugated. They may also be linear, branched or dendritic. In a linear structure the repeating units may either consist of a suitable compound of formula (I) or may be linked by means of a bivalent group, such as for example a substituted or unsubstituted alkylene group, a heteroatom or a bivalent aromatic or heteroaromatic group. In branched or dendritic structures three or even more suitable compounds of general formula (I) may be linked by means of a tri- or even higher-valent group, for example by means of a trivalent or higher-valent aromatic or heteroaromatic group, so as to form a branched or dendritic oligomer or polymer.

The present oligomers or polymers may be either homopolymerized or copolymerized in presence of at least one further monomer, in the following referred to as "comonomer". Suitable comonomers may be selected from the list consisting of fluorenes (for example those disclosed in EP 842208 or WO 00/22026), spirobifluorenes (for example those disclosed in EP 707020, EP 894107 or WO 06/061181), para-phenylenes (for example those disclosed in WO 1992/18552), carbazoles (for example those disclosed in WO 04/070772 or WO 2004/113468), thiophenes (for example those disclosed in EP 1028136), dihydrophenanthrenes (for example those disclosed in WO 2005/014689 or WO 2007/006383), cis- and trans-indenofluorenes (for example those disclosed in WO 2004/041901 or WO 2004/113412), ketones (for example those disclosed in WO 2005/040302), phenanthrenes (for example those disclosed in WO 2005/104264 or WO 2007/017066) and blends of any one or more of these.

The present oligomers, polymers and dendrimers may comprise further components such as for example emitting compounds, of which vinyltriarylamines (for example those disclosed in WO 2007/068325) or metal complexes (for example those disclosed in WO 2006/003000), and/or charge transporting components, particularly those comprising triarylamines.

The present oligomers, polymers and dendrimers may generally be produced by well known polymerization methods. As particularly well suited polymerization methods leading to the formation of C—C or C—N bonds the following may be mentioned:
  (A) SUZUKI-polymerization;
  (B) YAMAMOTO-polymerization;
  (C) STILLE-polymerization; and
  (D) HARTWIG-BUCHWALD-polymerization.

These methods including the respective polymerization conditions are well known to the skilled person and are also described in detail in the literature, for example in WO 2003/048225, WO 2004/037887 and WO 2004/037887.

Hence, the present application also provides for a method to produce the above oligomers, and polymers by polymerization according to a method selected from the group consisting of Suzuki-polymerization, Yamamoto-polymerization, Stille-polymerization, and Hartwig-Buchwald-polymerization. The respective dendrimers may be produced according to these methods or similar methods. Suitable methods for producing such dendrimers are for example disclosed in Jean M. J. Frechet, Craig J. Hawker, "Hyperbranched polyphenylene and hyperbranched polyesters: new soluble, three-dimensional, reactive polymers", Reactive & Functional Polymers (1995), 26(1-3), 127-36; H. M. Janssen, E. W. Meijer, "The synthesis and characterization of dendritic molecules", Materials Science and Technology (1999), 20 (Synthesis of Polymers), 403-458; Donald A. Tomalia, "Dendrimer molecules", Scientific American (1995), 272(5), 62-6; WO 2002/067343 A1; and WO 2005/026144 A1.

The compounds and polymers according to the present invention can also be used in mixtures or polymer blends, for example together with monomeric compounds or together with other polymers having charge-transport, semi-conducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Formulation

Another aspect of the invention relates to a formulation comprising one or more compounds of formula (I), oligomers, polymers, dendrimers or polymer blends as described above and below and one or more organic solvents. Such formulation may be a solution, a suspension or an emulsion. The manufacture of such formulations is well known and for example disclosed in WO 2002/072714, WO 2003/019694 and the literature cited therein.

Suitable organic solvents may for example be selected from the group consisting of toluene, anisol, o-xylene, m-xylene, p-xylene, methylbenzoate, mesitylene, tetraline, 1,2-dimethoxybenzene (commonly known as "veratrole"), tetrahydrofurane (commonly abbreviated as "THF"), methyl-tetrahydrofurane, tetrahydropyrane (oxane), chlorobenzene, dioxane, phenoxytoluene, particularly 3-phenoxytoluene, (−)-fenchone, 1,2,3,5-tetramethylbenzene, 1,2,4,5-tetramethylbenzene, 1-methylnaphthaline, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butylbenzoate, cumene, cyclohexanol, cyclohexanone, cyclohexylbenzene, decalin, dodecylbenzene, ethylbenzoate, indane, N-methyl-2-pyrrolidone (commonly abbreviated as "NMP"), p-cymene, ethyl phenyl ether, 1,4-diisopropylbenzene, dibenzylether, diethylenglycolbutylmethylether, triethylenglycolbutylmethylether, diethylenglycoldibutylether, triethylenglycoldimethylether, diethylenglycolmonobutylether, tripropylenglycoldimethylether, tetraethylenglycoldimethylether, 2-isopropylnaphthaline, pentylbenzene, hexylbenzene, heptylbenzene, octylbenzene, 1,1-bis(3,4-dimethylphenyl)ethane and blends of any of these.

Organic Electronic Devices

The compound, oligomer, polymer and dendrimer of the present invention can be used as active material in an organic electronic device. The term "active material" is used herein to denote for example charge injection materials, charge transport materials, charge blocking materials, emitting materials or matrix materials.

Preferably such organic electronic device comprises an anode, a cathode and an active layer, said active layer comprising said active material. Organic electronic devices of the present invention include, without limitation, optical, electrooptical, electronic, electroluminescent and photoluminescent devices. Examples thereof include, without limitation, organic field effect transistors (OFETs), organic thin film transistors (OTFTs), organic light emitting diodes (OLEDs), organic light emitting transistors (OLETs), organic photovoltaic devices (OPVs), organic photodetectors (OPDs), organic solar cells, laser diodes, Schottky diodes, photoconductors, and photodiodes. Preferably, the present devices are selected from the group consisting of organic light emitting diodes, and organic light emitting transistors. Most preferably the present devices are organic light emitting diodes.

In addition to the anode, cathode and active layer, the present organic electronic device may optionally comprise at least one further layer selected from the group consisting of electron transport layer, hole transport layer, hole injection layer, electron injection layer, exciton blocking layer, interlayers, and charge generation layer. The presence (or absence) of such further layers depends upon the type of organic device and the respective final use.

Because the present compound, oligomer, polymer or dendrimer show particularly advantageous properties when used as light emitting material in organic electroluminescent devices, it is preferred to use these as light emitting materials in light emitting layers of such devices.

If the organic electronic device of the present invention is an organic electroluminescent device it comprises an anode, a cathode and a light emitting layer. Optionally, in addition to these it may comprise one or more further layers selected from the group consisting of hole injection layer, hole transport layer, hole blocking layer, electron injection layer, electron transport layer, electron blocking layer, charge generation layer, exciton blocking layer, organic p/n-transition layer and inorganic p/n-transition layer. It may also be possible that one or more hole transport layers comprise a p-dopant. Exemplary p-dopants are metal oxides and (per) fluorinated electron-deficient aromatics. Examples of suitable metal oxides are—without limitation—$MoO_3$ and $WO_3$. It is also possible that—independent of any doping of a hole transport layer—one or more electron transport layers are doped with a n-dopant. Optionally, interlayers may be present between two light emitting layers—if such are present, which for example have an exciton blocking function and/or direct the charge equilibrium in the organic electroluminescent device.

The present organic electronic devices may also have more than one light emitting layer. In such a case it is preferred that the different light emitting layers have different emission maxima between 380 nm and 750 nm, thereby allowing the emission of light of different colors, and resulting for example in the emission of white light. Particularly preferred in this respect are organic electronic devices comprising three light emitting layers, wherein preferably at least one of these comprises the compound, oligomer, polymer or dendrimer of the present application and the three light emitting layers emit in the blue, green, and orange or red. For a description of the basic structure of such a device it is for example referred to WO 2005/011013. It is noted that instead of several different light emitting compounds it is also possible to use one compound that emits in a broad range of wavelength and in sum emits white light.

In a preferred aspect of the present invention the compound of general formula (I) is used as emitter in or more light emitting layers.

If used as an emitter in a light emitting layer, the compound of formula (I) is preferably used in combination with one or more matrix materials. The mixture comprising compound of formula (I) and a matrix material preferably comprises between 0.1 vol % and 99 vol %, preferably between 1 vol % and 90 vol %, even more preferably between 3 and 40 vol %, and most preferably between 5 vol % and 15 vol % of the compound of formula (I), relative to the total volume of the mixture.

As matrix materials any suitable materials known to the skilled person may be used, preferably such materials wherein the triplet-level of the matrix material is higher than the triplet-level of the emitter.

Suitable matrix materials used herein may be selected from the following: ketones, phosphinoxides, sulfoxides, sulfones, triarylamines, carbazol-derivatives, indolocarbazole-derivatives, indenocarbazole-derivatives, azacarbazoles, bipolar matrix materials, silanes, azaboroles, boronic acid esters, diazasilole-derivatives, triazine-derivatives, zinc-complexes, dibenzofurane-derivatives and bridged carbazole-derivatives. Suitable examples of sulfoxides and sulfones are for example disclosed in WO 2004/013080, WO 2004/093207, WO 2006/005627 or WO 2010/006680. Suitable derivatives of carbazoles are for example CBP (N,N-Bis-carbazolylbiphenyl), m-CBP or the ones disclosed in WO 2005/039246, US 2005/0069729, JP 2004/288381, EP 1205527, WO 2008/086851 and US 2009/0134784. Suitable derivatives of indolocarbazole are for example the ones disclosed in WO 2007/063754 or WO 2008/056746. Suitable examples of derivatives of indenocarbazole are for example the ones disclosed in WO 2010/136109 or WO 2011/000455. Suitable examples of azacarbazoles are for example disclosed in EP 1617710, EP 1617711, EP 1731584, or JP 2005/347160. Suitable examples of bipolar matrix materials are for example disclosed in WO 2007/137725. Suitable examples of silanes are for example disclosed in WO 2005/111172. Suitable examples of azaboroles or boronic acid esters are for example disclosed in WO 2006/117052. Suitable derivatives of diazasiloles are for example disclosed in WO 2010/054729. Suitable derivatives of diazaphospholes are for example disclosed in WO 2010/054730. Suitable derivatives of triazine are for example disclosed in WO 2010/015306, WO 2007/063754 or WO 2008/056746. Suitable zinc-complexes are for example disclosed in EP 652273 or WO 2009/062578. Suitable derivatives of dibenzofuranes are for example disclosed in WO 2009/148015. Suitable examples of bridged derivatives of carbazole are for example disclosed in US 2009/0136779, WO 2010/050778, WO 2011/042107 or WO 2011/088877.

Alternatively the compound, oligomer, polymer or dendrimer of the present application may be present in any of the other layers present in the organic electronic device, such as for example in the electron transport layer.

Preferably, the sequence of layers is as follows:
anode,
optional hole injection layer,
optional one or more hole transport layer,
light emitting layer,
optional electron transport layer,
optional electron injection layer, and
cathode.

It is noted that any layer indicated as "optional" may either be present or absent, depending upon the intended use and/or desired properties of the resulting device.

The anode is generally formed of an electrically conductive material. Exemplary electrically conductive materials include electrically conductive metals, electrically conductive alloys, electrically conductive polymers, and electrically conductive metal oxides. Exemplary electrically conductive metals include gold, silver, copper, aluminum, nickel, palladium, platinum, and titanium. Exemplary electrically conductive alloys include stainless steel (e.g., 332 stainless steel, 316 stainless steel), alloys of gold, alloys of silver, alloys of copper, alloys of aluminum, alloys of nickel, alloys of palladium, alloys of platinum, and alloys of titanium. Exemplary electrically conducting polymers include polythiophenes (e.g., doped poly(3,4-ethylenedioxythiophene)), polyanilines (e.g., doped polyanilines), polypyrroles (e.g., doped polypyrroles). Exemplary electrically conducting metal oxides include indium tin oxide, indium zinc oxide, fluorinated tin oxide, tin oxide and zinc oxide. It is preferred that the anode is formed of a material with high work function, for example with a work function of at least 4.5 eV versus vacuum. In some embodiments, blends or combinations of electrically conductive materials are used. In some embodiment, it may be advantageous to form the anode of transparent material, such as for example indium tin oxide or indium zinc oxide. Alternatively the anode may comprise more than one layer, for example it may comprise an inner layer of indium tin oxide and an outer layer of tungsten oxide, molybdenum oxide or vanadium oxide.

The cathode is generally formed of an electrically conductive material, preferably one with a low work function. Exemplary materials suitable are metals such as earth alkaline metal, main group metals or lanthanide. Particular examples of such metals are Ca, Ba, Mg, Al, In, Yb, Sm and Eu as well as alloys thereof. It is also possible to use alloys of silver and an alkaline metal or alkaline earth metal, such as for example an alloy of silver and magnesium. The cathode may also be formed of more than one layer, in which case metals or alloys having a higher work function may be present. Examples of such metals or alloys having a higher work function are Ag, Al, Ca/Ag alloy, Mg/Ag alloy and Ba/Ag alloy.

In some embodiments the cathode may also comprise a layer of material having a high dielectric constant. Examples of suitable materials are metal fluorides, oxides or carbonates with the metal selected from the alkaline and alkaline earth metals. Specific examples of such materials are LiF, $Li_2O$, $BaF_2$, MgO, NaF, CsF, $Cs_2CO_3$ or $CaF_2$. Lithium chinolate may also be used.

Further suitable materials for a charge transport layer, for example for a hole transport layer or an electron transport layer, are for example disclosed in Y. Shirota et al., Chemical Reviews 2007, 107(4), 953-1010. Suitable examples are aluminum complexes, zirconium complexes, benzimidazole, triazine, pyridine, pyrimidine, pyrazine, chinoxaline, chinoline, oxadiazole, aromatic ketones, lactame, borane, diazaphosphole, phosphinoxide and their derivatives as for example disclosed in JP 2000/053957, WO 2003/060956, WO 2004/028217, WO 2004/080975 or WO 2010/072300.

Preferred examples of hole transport materials, which may be used in a hole transport, hole injection or electron blocking layer, are derivatives of indenofluorene amine (e.g. disclosed in WO 06/122630 or WO 06/100896), amines (e.g. the amines disclosed in EP 1661888 or those disclosed in WO 95/09147), derivatives of hexaazatriphenylene (e.g. disclosed in WO 01/049806), derivatives of amines with annealed aryls (e.g. as disclosed in U.S. Pat. No. 5,061,569), monobenzoindenofluorenamines (for example as disclosed in WO 08/006449), dibenzoindenofluorenamines (for example as disclosed in WO 07/140847), spirobifluoreneamines (for example as disclosed in WO 2012/034627), fluorene-amines, spiro-dibenzopyrane-amines and derivatives of acridine.

In order to avoid or reduce the damaging effects of water and air the organic electronic device of the present invention is subsequently enclosed and sealed.

The present compound, oligomers, polymers or dendrimers as defined above, or alternatively their respective formulations as defined above, may be used in the production of organic electronic devices, particularly organic light emitting diodes (OLEDs). In particular, they are useful in the production of the light emitting layer of an organic light emitting diode.

The organic electronic device of the present invention may be produced by any suitable method. For example, one or more layer comprised in such organic electronic device may be deposited by sublimation, by organic vapor phase deposition (OPVD), by carrier gas sublimation, by organic vapor jet printing, by spin-coating or by any printing method, such as for example screen-printing, ink-jet printing, flexographic printing, or light induced thermal imaging.

Hence, the present invention also provides for a method for producing the present electronic devices, said method comprising the steps of
(a) providing the compound, polymer, oligomer or dendrimer of the present invention; and
(b) depositing said compound, polymer, oligomer or dendrimer on a supporting layer.

The present organic electronic devices may for example be used in displays, light sources in lighting appliances as well as for example in medical and cosmetic appliances.

It is believed that the compounds, oligomers, polymers and dendrimers of the present invention are to have particularly advantageous properties in organic light emitting devices because of the reduced energy difference between S1-level and T1-level, which have been confirmed by calculations. Without wishing to be bound by theory it is believed that this is the result of the particular arrangement of substituents on the six-membered ring of the compound of the present invention. Calculations furthermore indicate that the compounds of the present invention will emit in the blue region and as such are particularly desirable for use in organic light emitting compounds.

EXAMPLES

The following syntheses are, if not indicated otherwise, performed in dried solvents under an inert atmosphere. Solvents and reagents may be purchased for example from Sigma-ALDRICH or ABCR.

The following abbreviations are used: "THF" for tetrahydrofurane; "DMF" for dimethylformamide; "FEP" for fluorinated ethylene propylene; "DCM" for dichlormethane ($CH_2Cl_2$); "NMR" for nuclear magnetic resonance.

Example S1—Synthesis of 5,6-dibromo-1,1,2,2,3,3-hexamethylindane (S1)

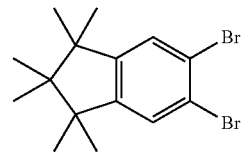 [SMILES: CC1(C)c2cc(Br)c(Br)cc2C(C)(C)C1(C)C]

To a solution of 101.2 g (500 mmol) 1,1,2,2,3,3-hexamethyl-indane (CAS-no. 91324-94-6) in 2000 ml dichloromethane 1.3 g water-free iron(III) chloride are added. Then a mixture of 64.0 ml (1.25 mol) bromine and 300 ml dichloromethane is added in the absence of light in such a way that the temperature does not exceed 25° C., if necessary by cooling with a cold water bath. After stirring the reaction mixture for 16 hours at room temperature 500 ml of a saturated aqueous solution of sodium sulfite are slowly added, followed by separation of the aqueous phase. The organic phase is successively washed three times with 1000 ml water each, dried over sodium sulfate, and filtered through a short column of silica gel. Subsequently the solvent is evaporated. The obtained solid is re-crystallized from ca. 100 ml ethanol.

The following compounds S2 to S5 may be synthesized accordingly:

| Ex. | Starting material | Product |
|---|---|---|
| S2 | (CAS no. 577-55-9) | S2 |
| S3 | (CAS no. 4834-33-7) | S3 |
| S4 | (CAS no. 113710-83-1) | S4 |
| S5 | (CAS no. 4175-52-4) | S5 |

Example S6—Synthesis of 5,6-dicyano-1,1,2,2,3,3-hexamethylindane (S6)

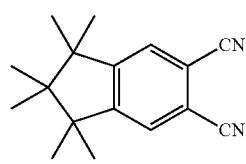 [SMILES: CC1(C)c2cc(C#N)c(C#N)cc2C(C)(C)C1(C)C]

The synthesis may be conducted according to T. Schareina et al., Chem. Eur. J., 2007, 13, 6249. In an autoclave a mixture of 36.0 g (100 mmol) 5,6-bromo-1,1,2,2,3,3-hexamethylindane (S1), 18.4 g (50 mmol) K₄[Fe(CN)₆] (water-free, CAS no. 13943-58-3), 1.9 g (10 mmol) copper (I) iodide, 26.4 ml (200 mmol) 1-butyl-imidazole and 200 ml toluene is heated to 110° C. for 20 h. After cooling to room temperature the reaction mixture is diluted with 300 ml toluene. The organic phases are successively washed three times with 300 ml water each, dried over magnesium sulfate and filtered through Celite. Following the removal of the toluene in vacuum, the residue is re-crystallized twice from dimethylformamide/ethanol.

The following compounds S7 to S11 may be synthesized accordingly:

| Ex. | Starting material | Product |
|---|---|---|
| S7 | S2 | S7 (purified by chromatography) |
| S8 | S3 | S8 (CAS no. 137818-51-0) |
| S9 | S4 | S9 |
| S10 | (CAS no. 42810-32-2) | S10 (CAS no. 52477-73-3) |
| S11 | S5 | S11 |

Example S12—Synthesis of 4,7-dibromo-5,6-dicyano-1,1,2,2,3,3-hexamethylindane (S12)

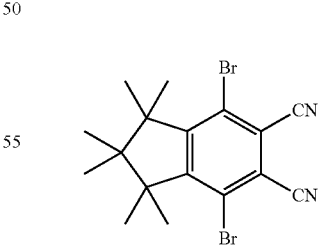

The synthesis may be conducted according to B. Du et al., J. Org. Chem., 2013, 78, 2786. A mixture of 12.6 g (50 mmol) 5,6-dicyano-1,1,2,2,3,3-hexamethylindane (S6), 21.4 g (120 mmol) N-bromosuccinimide, 1.1 g (5 mmol) palladium(II) acetate, 951 mg (5 mmol) p-toluenesulfonic acid monohydrate and 300 ml 1,2-dichloroethane is stirred at 80° C. for 30 h. After cooling to room temperature the reaction mixture is successively washed three times with 300 ml each of 5 wt % aqueous solution of ammonia, then once with saturated sodium chloride solution, dried over magnesium sulfate and filtered over Celite. After removal of the solvent under vacuum the residue is purified by chromatography on silica gel with ethyl acetate/n-heptane in a 1:1 volume ratio.

The following compounds S13 to S17 may be synthesized accordingly:

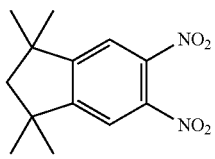 [SMILES: CC1(C)CC(C)(C)c2cc([N+](=O)[O-])c([N+](=O)[O-])cc21]

Example S18—Synthesis of 1,1,3,3-tetramethyl-indane-5,6-diamine

Step A: Synthesis of 5,6-dinitro-1,1,3,3-tetramethyl-indane (S18a)

At 0° C. 350 ml nitric acid (100%) are slowly added to a well-stirred mixture of 87.2 g (500 mmol) 1,1,3,3-tetramethylindan (CAS-no. 4834-33-7) and 350 ml sulfuric acid (95%) so that the temperature does not exceed +5° C. The reaction mixture is then allowed to slowly warm to room temperature over a period of 2 to 3 h and is subsequently added to a well-stirred mixture of 6 kg ice and 2 kg water. The pH is adjusted to between 8 and 9 by the addition of 40 wt % aqueous sodium hydroxide solution. Subsequently one extracts three times with 1000 ml ethyl acetate each, successively washes the combined organic phases twice with 1000 ml water each, dries over magnesium sulfate, and under vacuum almost completely removes the ethyl acetate until crystallization commences. Crystallization is then completed by the addition of 500 ml heptane. The beige-colored crystals are separated by vacuum filtration and dried in vacuo.

Step B—Synthesis of 1,1,3,3-Tetramethyl-indan-5,6-diamin (S18)

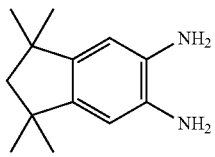

126.9 g (480 mmol) 5,6-dinitro-1,1,3,3-tetramethylindane (S18a) in 1200 ml ethanol are hydrogenated in presence of 10 g palladium on carbon as catalyst under 3 bars of hydrogen pressure for a period of 24 h. The reaction mixture is successively filtered twice over a bed of Celite. The ethanol is removed. The obtained brown solid is purified by Kugelrohr distillation at a temperature of about 160° C. at a pressure of about $10^{-4}$ mbar.

The following compounds S19 to S23 may be synthesized accordingly:

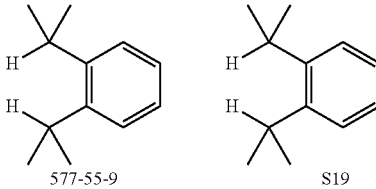

| Ex. | Starting material | Product |
|---|---|---|
| S20 | 91324-94-6 | S20 |
| S21 | 113710-83-1 | S21 |
| S22 | 4486-29-7 | 124639-03-8/S22 |
| S23 | 4175-52-4 | S23 |

Example S24—Synthesis of 5,6-difluoro-1,1,3,3-tetramethylindane (S24)

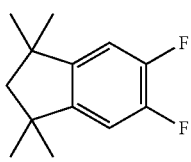

The synthesis may be conducted according to K. Sasaki et al., J. Fluorine Chem., 1996, 76, 59. In a FEP flask 100 ml of a mixture of HF and pyridine in a 60:40 weight ratio are cooled to 5° C. Then 6.4 g (30 mmol) 1,1,3,3-tetramethyl-indane-5,6-diamine (S18) and 4.5 g (65 mmol) sodium nitrite are successively added in small portions. The reaction mixture is allowed to warm to 10° C. and stirred for 45 min. Subsequently 11.4 g (60 mmol) tin(II) chloride and 18.1 g (60 mmol) tetrabutylammonium dihydrogen trifluoride are added. The resulting reaction mixture is then slowly warmed to 100° C. (Attention: Foaming and evolution of gas) and is stirred at 100° C. for 5 h. After cooling the reaction mixture is poured into 1000 g of ice and water, followed by successive extraction with 300 ml of dichloromethane three times each. 'The combined organic phases are then washed with 300 ml of a saturated aqueous solution of calcium chloride and dried over magnesium sulfate. After removal of the solvent the product is purified first by chromatography on silica gel with a mixture of n-heptane and DCM in a 9:1 volume ratio and then by Kugelrohr distillation.

The following compounds S25 to S29 may be synthesized accordingly:

| Ex. | Starting material | Product |
|---|---|---|
| S25 | S19 | S25 |
| S26 | S20 | S26 |
| S27 | S21 | S27 |
| S28 | S22 CAS no. 124639-03-8 | S28 |
| S29 | S23 | S29 |

Example S30—Synthesis of 4,7-dibromo-5,6-difluoro-1,1,2,2,3,3-hexamethylindane

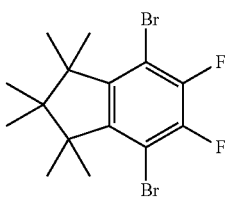 [SMILES: CC1(C)c2c(Br)c(F)c(F)c(Br)c2C(C)(C)C1(C)C]

A freshly prepared solution of 110 mmol lithium diisoproylamide (LDA) in 110 ml THF is added dropwise to a solution of 11.9 g (50 mmol) 5,6-difluoro-1,1,3,3-tetramethylindane in 300 ml THF cooled to −78° C. and then stirred for an hour. In the following a solution of 36.5 g (110 mmol) tetrabromomethane in 200 ml THF is added quickly and stirring is continued for 30 min. The reaction mixture is allowed to warm to −20° C. and quenched by the addition of 20 ml methanol. The solvent is removed and the residue is purified by chromatography on silica gel with a mixture of n-heptane and DCM in a 9:1 volume ratio.

The following compounds S31 to S35 may be synthesized accordingly:

| Ex. | Starting material | Product |
|---|---|---|
| S31 | S25 | S31 |
| S32 | S26 | S32 |
| S33 | S27 | S33 |
| S34 | S28 | S34 |
| S35 | S29 | S35 |

Example S36—Synthesis of 4,7-dicyano-5,6-difluoro-1,1,2,2,3,3-hexamethylindane

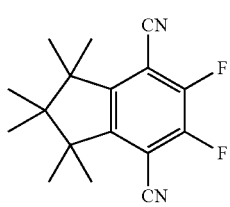 [SMILES: CC1(C)c2c(C#N)c(F)c(F)c(C#N)c2C(C)(C)C1(C)C]

The synthesis may be conducted in accordance with Example S6, except that instead of 5,6-bromo-1,1,2,2,3,3-hexamethylindane (S1) 4.0 g (10 mmol) 4,7-dibromo-5,6-difluoro-1,1,2,2,3,3-hexamethylindane (S30) is used and the respective amounts of the other reactants are adapted in proportion to the amount of S30.

The following compounds S37 to S41 may be synthesized accordingly:

| Ex. | Starting material | Product |
|---|---|---|
| S37 | S31 | S37 |
| S38 | S32 | S38 |
| S39 | S33 | S39 |
| S40 | S34 | S40 |
| S41 | S35 | S41 |

Example B1—Synthesis of 4,7-bis-N-carbazolyl-5,6-dicyano-1,1,2,2,3,3-hexamethylindane (B1)

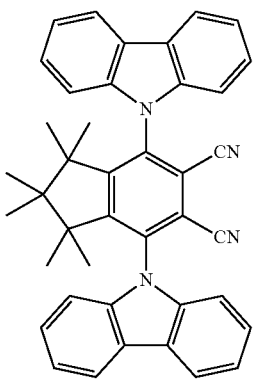 [SMILES: CC1(C)c2c(-n3c4ccccc4c4ccccc43)c(C#N)c(C#N)c(-n3c4ccccc4c4ccccc43)c2C(C)(C)C1(C)C]

The synthesis may be conducted in accordance with B. Hu et al., Tetrahedron, 2010, 66(38), 7583. A mixture of 20.5 g (50 mmol) 4,7-dibromo-5,6-dicyano-1,1,2,2,3,3-hexamethylindane (S12), 33.4 g (200 mmol) carbazole (CAS no. 86-74-8), 55.3 g (400 mmol) potassium carbonate, 635 mg (10 mmol) copper powder, 26.4 g (100 mmol) 18-crown-6, 100 g glass beads (4 mm diameter) and 500 ml dimethylformamide are heated to slight reflux under good stirring for 48 h while evolving water is collected in a Dean-Stark trap and removed from time to time. After cooling 500 ml of ethyl acetate are added. Glass beads and salts are removed by vacuum filtration over Celite. The filtrate is successively washed five times with 500 ml water each, once with 500 ml aqueous saturated solution of sodium chloride and dried over magnesium sulfate. After removal of the solvent the residue is successively re-crystallized five times from DMF/ethanol and subsequently purified at a temperature of about 310° C. under a pressure of about $10^{-5}$ mbar by three successive fractionated sublimations.

The following compounds B2 to B7 may be synthesized accordingly:

| Ex. | Starting materials | Product |
|---|---|---|
| B4 | 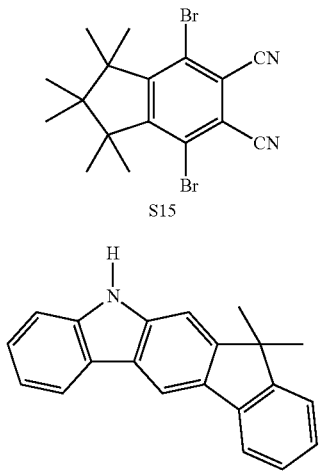<br>S15<br><br>CAS no. 1257220-47-5 | 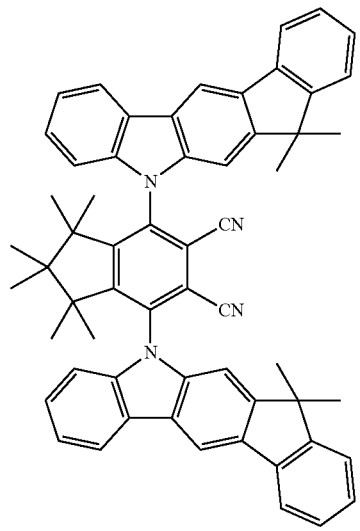 [SMILES: CC1(C)c2ccccc2-c2cc3c4ccccc4n(-c4c(C#N)c(C#N)c(-n5c6ccccc6c6cc7c(cc65)C(C)(C)c5ccccc5-7)c5c4C(C)(C)C(C)(C)C5(C)C)c3cc21]<br>B4 |
| B5 | 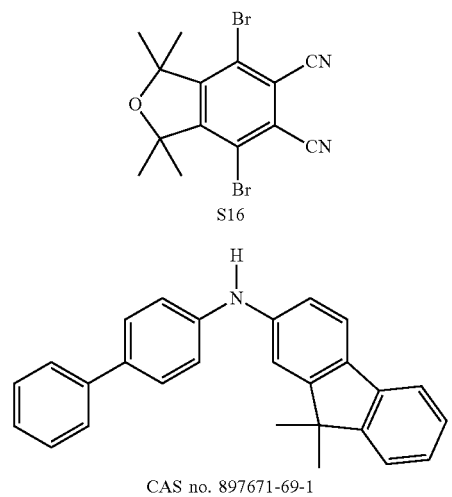<br>S16<br><br>CAS no. 897671-69-1 | 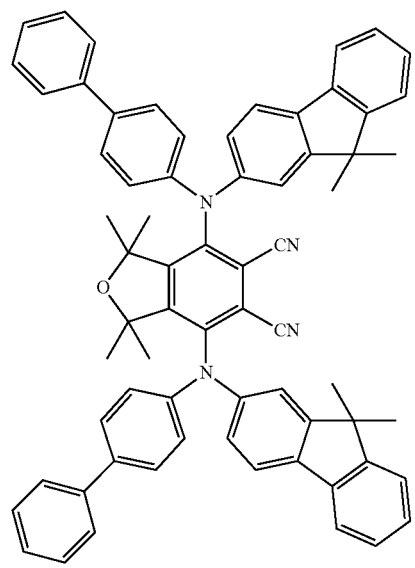 [SMILES: CC1(C)OC(C)(C)c2c(N(c3ccc(-c4ccccc4)cc3)c3ccc4c(c3)C(C)(C)c3ccccc3-4)c(C#N)c(C#N)c(N(c3ccc(-c4ccccc4)cc3)c3ccc4c(c3)C(C)(C)c3ccccc3-4)c21]<br>B5 |

| Ex. | Starting materials | Product |
|---|---|---|
| B6 | 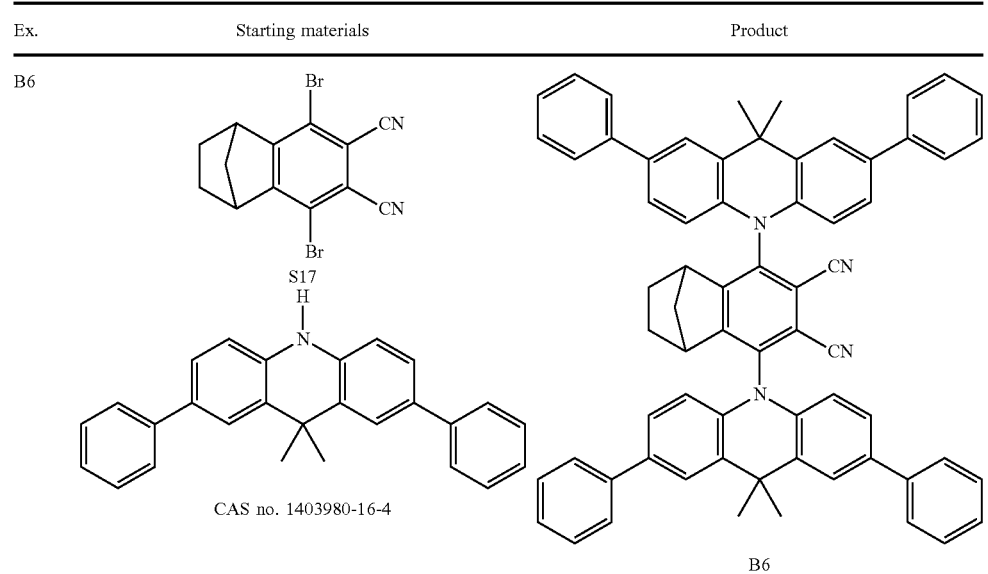 | |
| B7 | 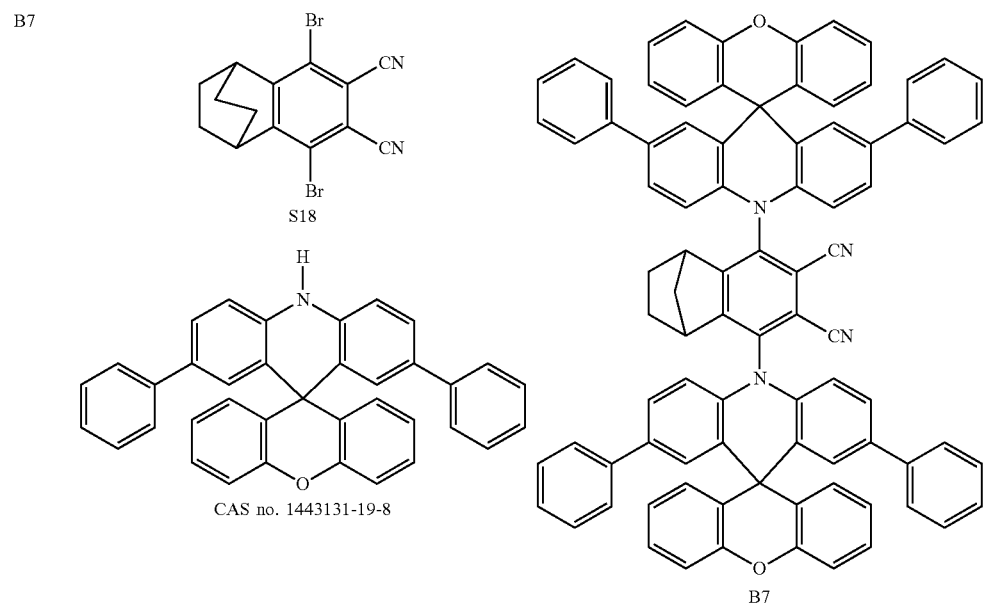 | |

Example B8—Synthesis of 4,7-dicyano-5,6-bis-N-carbazolyl-1,1,2,2,3,3-hexamethylindane (B8)

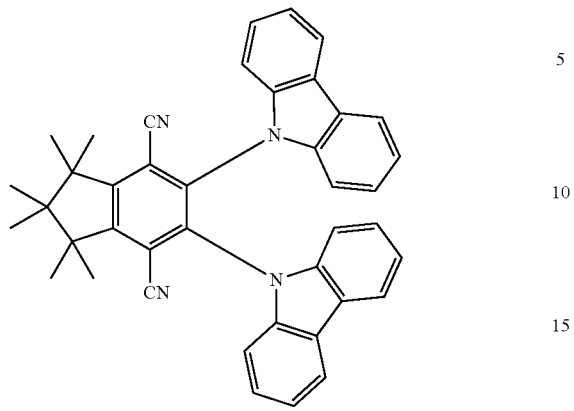

A suspension of 960 mg (40 mmol) sodium hydride in 50 ml THF is cooled to 0° C. Then 6.7 g (40 mmol) carbazole (CAS no. 86-74-8) is added in portions (Attention: Evolution of hydrogen, foaming). After warming to room temperature the reaction mixture is stirred for ane hour, following which a solution of 2.9 g (10 mmol) 4,7-dicyano-5,6-difluoro-1,1,2,2,3,3-hexamethylindane (S36) in 50 ml THF is added slowly. After the exothermic reaction has stopped one continues to stir at 50° C. for 16 h, the adds 50 ml ethanol and removes the solvent in vacuo. The residue is dissolved in 300 ml DCM. The organic phase is successively washed three times with 200 ml water each and once with 100 ml of an aqueous saturated sodium chloride solution, dried over magnesium sulfate and then filtered over Celite. After removal of the solvent the residue is re-crystallized five times from DMF/ethanol and is then purified by three successive fractionated sublimations at a temperature of about 320° C. at a pressure of about $10^{-5}$ mbar.

The following compounds B9 to B13 mayn be synthesized accordingly:

| Ex. | Starting materials | Product |
|---|---|---|
| B9 | S37, CAS no. 1257220-49-7 | B9 |

| Ex. | Starting materials | Product |
|---|---|---|
| B10 | 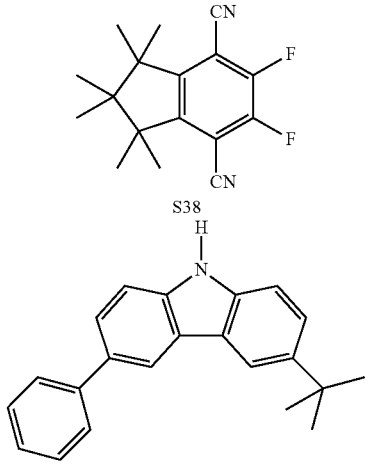
S38
CAS no. 1335126-51-6 | 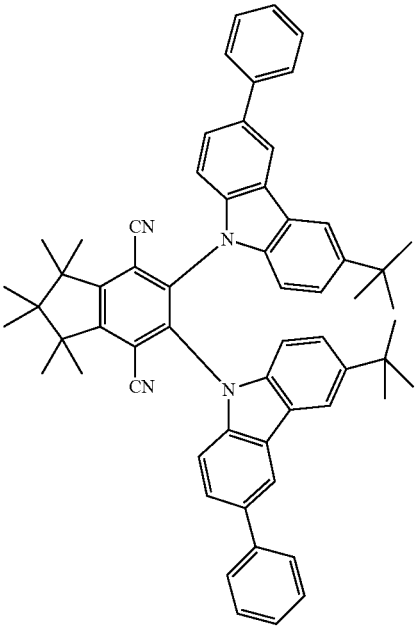 [SMILES: CC(C)(C)c1ccc2c(c1)c1cc(-c3ccccc3)ccc1n2-c1c(C#N)c2c(c(C#N)c1-n1c3ccc(-c4ccccc4)cc3c3cc(C(C)(C)C)ccc31)C(C)(C)C(C)(C)C2(C)C]
B10 |
| B11 | 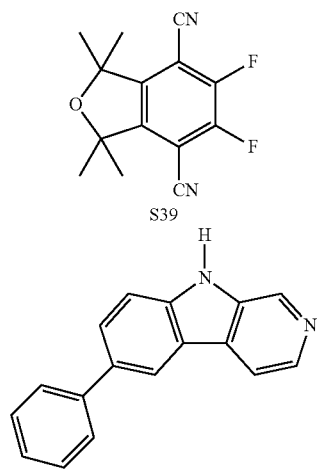
S39
CAS no. 99822-95-4 | 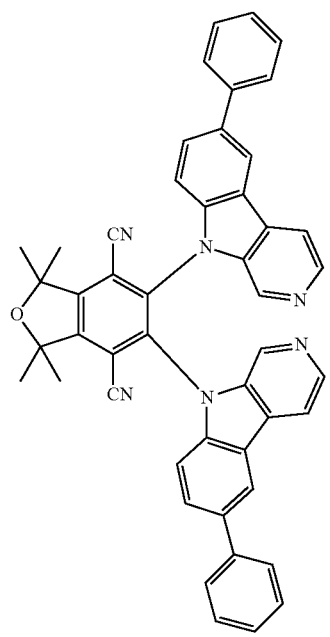 [SMILES: CC1(C)OC(C)(C)c2c(C#N)c(-n3c4ccc(-c5ccccc5)cc4c4ccncc43)c(-n3c4ccc(-c5ccccc5)cc4c4ccncc43)c(C#N)c21]
B11 |

-continued

| Ex. | Starting materials | Product |
|---|---|---|

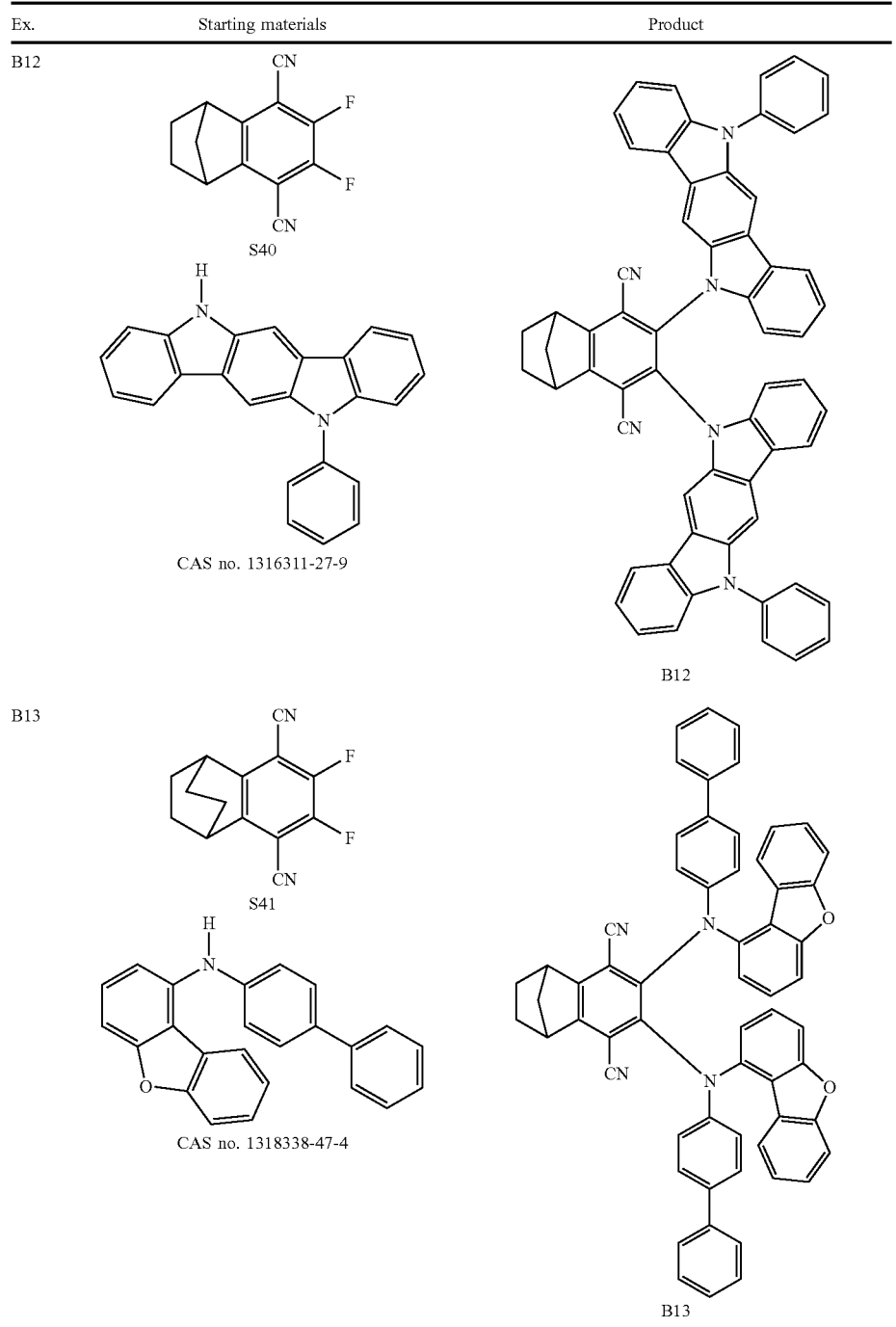

Example—Production of OLEDs a) Vacuum-Processed Devices

OLEDs according to the invention and OLEDs in accordance with the prior art are produced by a general process in accordance with WO 2004/058911, which is adapted to the circumstances described here (layer-thickness variation, materials used). Glass plates with structured ITO (indium tin oxide, 50 nm) form the substrates to which the OLEDs are applied. The substrates are cleaned by a wet cleaning process (dishwasher, detergent Extran from Merck), then dried for 15 min at 250° C. and treated with an $O_2$-plasma prior to use.

The OLEDs have in principle the following layer structure: substrate/hole-transport layer (HTL)/optional electron blocking layer (EBL)/emission layer (EML)/optional hole blocking layer/electron-transport layer (ETL)/optional electron-injection layer (EIL) and finally a cathode. The cathode is formed by an aluminium layer with a thickness of 100 nm.

Firstly, vacuum-processed OLEDs are described. For this purpose, all materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as matrix M:B (95%:5%) here means that material M is present in the layer in a proportion by volume of 95% and the dopant B is present in the layer in a proportion of 5%. Analogously, the electron-transport layer may also consist of a mixture of two materials. The precise structure of such OLEDs is shown in Table 1. The materials used for the production of such OLEDs are shown in Table 2.

TABLE 1

Structure of the OLEDs

| Ex. | HTL Thickness | EBL Thickness | EML Thickness | HBL Thickness | ETL Thickness | EIL Thickness |
|---|---|---|---|---|---|---|
| D-Ref reference | HTM 90 nm | — | M1:DR (95%:5%) 20 nm | — | ETM 50 nm | EIM 3 nm |
| D-B1 | HTM 90 nm | EBM 10 nm | M2:M3:B1 (65%:30%:5%) 20 nm | HBM 10 nm | ETM 50 nm | EIM 3 nm |
| D-B8 | HTM 90 nm | — | M1:B8 (95%:5%) 20 nm | — | ETM 50 nm | EIM 3 nm |

TABLE 2

Structural formulae of the materials

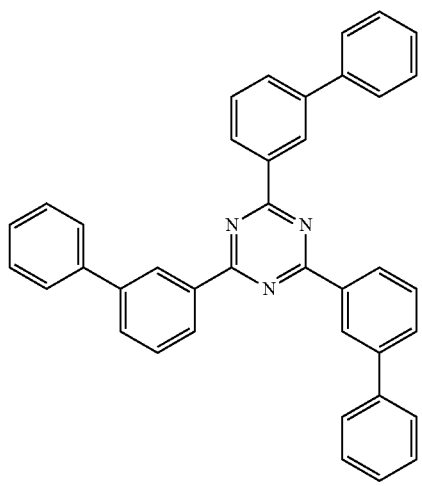 [SMILES: c1ccc(-c2cccc(-c3nc(-c4cccc(-c5ccccc5)c4)nc(-c4cccc(-c5ccccc5)c4)n3)c2)cc1]

CAS no. 123847-85-8
HTM = NPB

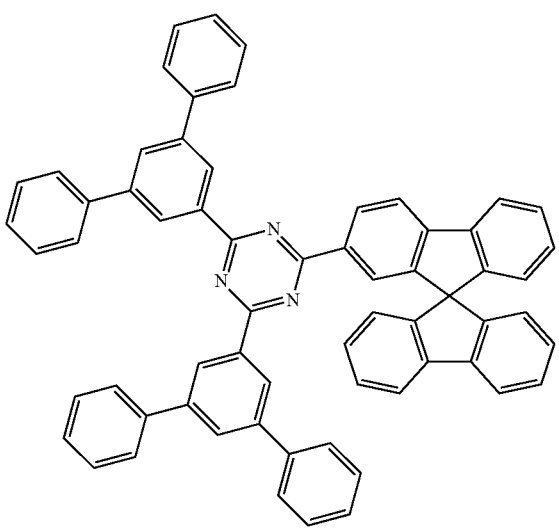 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

CAS no. 1206465-62-4
EBM

TABLE 2-continued

Structural formulae of the materials

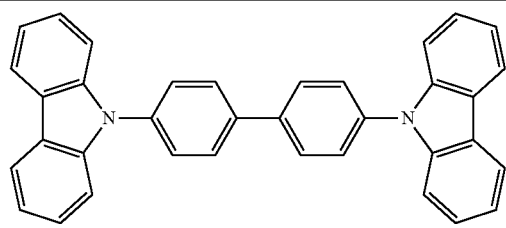

CAS no. 58328-31-7
M1 = CBP

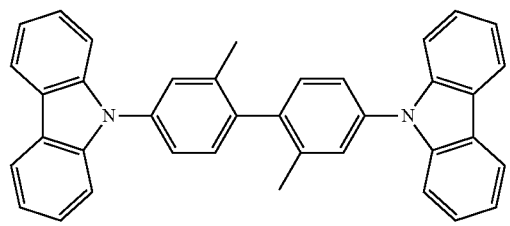 [SMILES: Cc1cc(-n2c3ccccc3c3ccccc32)ccc1-c1ccc(-n2c3ccccc3c3ccccc32)cc1C]

CAS no. 604785-54-8
M2

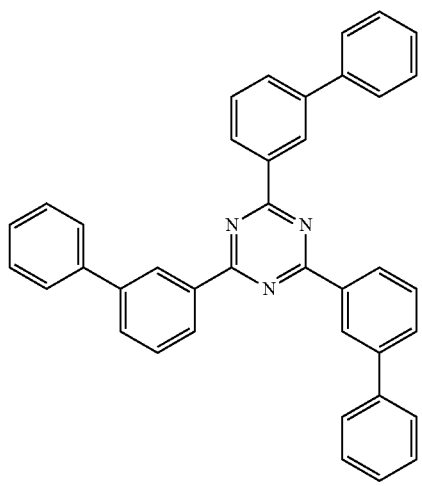 [SMILES: c1ccc(-c2cccc(-c3nc(-c4cccc(-c5ccccc5)c4)nc(-c4cccc(-c5ccccc5)c4)n3)c2)cc1]

CAS no. 1201800-83-0
M3/HBM

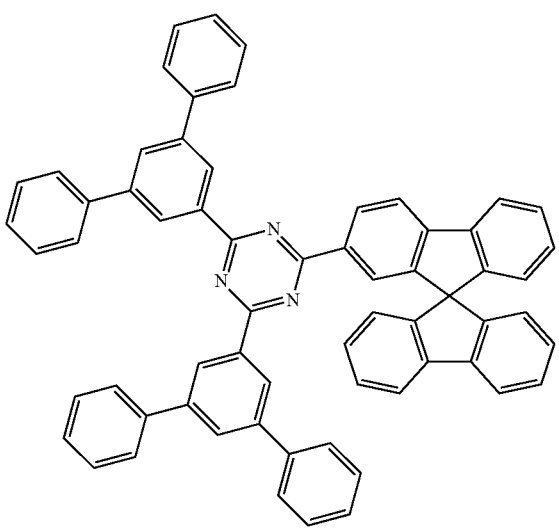 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

CAS no. 1233200-52-6
ETM

TABLE 2-continued

Structural formulae of the materials

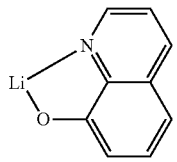

CAS no. 25387-93-3
EIM

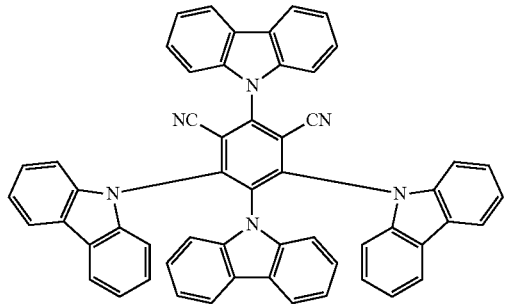 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]

CAS no. 1416881-52-1
DR

The OLEDs are characterised by standard methods. For this purpose, the electroluminescence spectra, the current efficiency (measured in cd/A) and the voltage (measured at 1000 cd/m² in V) are determined from current/voltage/luminance characteristic lines (IUL characteristic lines). For selected experiments, the lifetime is determined. The lifetime is defined as the time after which the luminous density has dropped to a certain proportion from a certain initial luminous density. The expression LT80 means that the lifetime given is the time at which the luminous density has dropped to 80% of the initial luminous density, i.e. from, for example, 1000 cd/m² to 800 cd/m². Depending on the emission colour, different initial luminances were selected. The values for the lifetime can be converted to a figure for other initial luminous densities with the aid of conversion formulae known to the person skilled in the art. The lifetime for an initial luminous density of 1000 cd/m² is a usual figure here.

b) Use of Compounds According to the Invention as Emitter Materials in OLEDs

The compounds according to the invention can be employed, inter alia, as emitter materials (dopants) in the emission layer in OLEDs. The compound DR is used as comparison in accordance with the prior art.

The invention claimed is:

1. A compound selected from the group consisting of

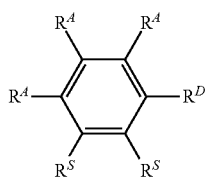

(I-a)

(I-b)

(I-c)

(I-d)

(I-e)

(I-f)

(I-g) and (I-h)

wherein
$R^A$ wherein at each occurrence $R^A$ is independently of each other selected from the group consisting of fluoroalkyl, F, $BR^1{}_2$, $B(OR^1)_2$, CHO, $C(=O)R^1$, $C(=O)OR^1$, $C(=O)N(R^1)_2$, $CR^1=C(CN)_2$, $N_3$, $NO_2$, $P(=O)(R^1)_2$, $S(=O)R^1$, $S(=O)_2R^1$, heteroaryl, heteroaryl substituted with one or more electron withdrawing groups and aryl substituted with one or more electron withdrawing groups, wherein the electron withdrawing groups are selected from the group consisting of fluoroalkyl, F, $B(OR^1)_2$, CHO, $C(=O)R^1$, CN, $C(=O)OR^1$, $C(=O)N(R^1)_2$, $NO_2$, $P(=O)(R^1)_2$, $S(=O)R^1$, and $S(=O)_2R^1$;

$R^D$ is independently of each other of general formula (N-a)

wherein
$Ar^{1'}$ is a substituted or unsubstituted aromatic with 6 to 30 aromatic ring atoms, or a heteroaromatic ring system with 5 to 30 aromatic ring atoms;
m is 0 or 1;
and
two $R^S$ together form a five-membered ring,
wherein two groups $R^S$ together form a five-membered ring of the following formulae (II-A)

 (II-A)

$A^1$ and $A^3$ are at each occurrence independently selected from the group consisting of $C(R^3)_2$, O, S, $NR^3$ and C(=O);
$A^2$ is at each occurrence independently selected from the group consisting of $C(R^1)_2$, O, S, $NR^3$ and C(=O); and in case two groups $A^2$ are adjacent to each other, $A^2$-$A^2$ may also be selected from the group consisting of ortho-linked arylene- or heteroarylene-group with 5 to 14 aromatic ring atoms, each of which may independently of the other be substituted with $R^2$ as defined above;
$R^1$ is at each occurrence independently selected from the group consisting of H, D, F, Cl, Br, I, $B(OR^2)_2$, CHO, C(=O)$R^2$, $CR^2$=C($R^2)_2$, CN, C(=O)$OR^2$, C(=O)N($R^2)_2$, Si($R^2)_3$, N($R^2)_2$, $NO_2$, P(=O)($R^2)_2$, $OSO_2R^2$, $OR^2$, S(=O)$R^2$, S(=O)$_2R^2$, OH, SH, linear alkyl-, alkoxy- or thioalkyl-group with 1 to 20 C-atoms or a branched or cyclic alkyl-, alkoxy- or thioalkyl-group with 3 to 20 C-atoms or a alkenyl- or alkinyl-group with 2 to 20 C-atoms, wherein the group may be substituted with one or more of groups $R^2$ and wherein one or more $CH_2$-groups in the group may be replaced by —$R^2$C=$CR^2$—, —C≡C—, Si($R^2)_2$, C=O, C=S, C=$NR^2$, C(=O)O—, C(=O)$NR^2$—, $NR^2$, P(=O)($R^2$), O, S, SO or $SO_2$, and wherein one or more H-atoms in the group may be replaced by D, F, Cl, Br, I, CN or $NO_2$, or an aromatic or heteroaromatic ring system with 5 to 60 aromatic ring atoms, which can be substituted with one or more groups $R^2$, or an aryloxy- or heteroaryloxy-group with 5 to 60 aromatic ring atoms, which can be substituted with one or more groups $R^2$, or an aralkyl- or heteroaralkyl-group with 5 to 60 aromatic ring atoms, which can be substituted with one or more groups $R^2$, wherein two or more groups $R^2$ may be linked with each other and form an aliphatic or aromatic or heteroaromatic ring;
$R^2$ is at each occurrence independently selected from the group consisting of H, D, F, alkyl having from 1 to 20 C-atoms, aromatic groups having from 1 to 20 aromatic carbon atoms and heteroaromatic groups having from 1 to 20 aromatic ring atoms, wherein the aromatic groups and the heteroaromatic groups may be substituted with an alkyl having from 1 to 20 carbon atoms; and
$R^3$ is at each occurrence independently selected from the group consisting of F, linear alkyl- or alkoxy-group with 1 to 20 C-atoms, a branched or cyclic alkyl- or alkoxy-group with 3 to 20 C-atoms, each of which may be substituted with one or more of groups $R^2$, wherein one or more non-adjacent $CH_2$-groups may be replaced by $R^2$C=$CR^2$, C≡C, Si($R^2)_2$, C=O, $NR^2$, O, S or $CONR^2$, and wherein one or more H-atom may be replaced with D or F, or an aromatic or heteroaromatic ring system with 5 to 24 aromatic ring atoms, each of which may each be substituted with one or more of groups $R^2$, or an aryloxy- or heteroaryloxy-group with 5 to 24 aromatic ring atoms, which can be substituted with one or more groups $R^2$, or an aralkyl- or heteroaralkyl-group with 5 to 24 aromatic ring atoms, which can be substituted with one or more groups $R^2$, wherein two $R^2$ bound to the same carbon atom may form an aliphatic or aromatic ring system and thus a spiro system; or $R^3$ can form together with a neighboring group $R^1$ or $R^2$ an aliphatic ring system,
provided that in $A^1$-$A^2$-$A^3$ no two heteroatoms are adjacent.

2. The compound according to claim 1 of the formula (I-e).

3. The compound according to claim 1, wherein at each occurrence $R^D$ is

 (N-b)

wherein
$Ar^1$ is a substituted or unsubstituted aromatic with 6 to 30 aromatic ring atoms, or a heteroaromatic ring system with 5 to 30 aromatic ring atoms;
$Ar^2$ is a substituted or unsubstituted aromatic or heteroaromatic ring system with 5 to 30 aromatic carbon atoms, wherein the two groups $Ar^2$ may be linked by a group Y, so that together with the N-atom of the $NAr^2_2$-group, irrespective of any N-atoms that might be present in $Ar^2$, a ring is formed;
Y is selected from the group consisting of a single bond, $BR^1$, $C(R^1)_2$, Si($R^1)_2$, $NR^1$, $PR^1$, P(=O)$R^1$, P(=S)$R^1$, O, S, S=O and S(=O)$_2$; and
$R^1$ is at each occurrence independently selected from the group consisting of H, D, F, Cl, Br, I, $B(OR^2)_2$, CHO, C(=O)$R^2$, $CR^2$=C($R^2)_2$, CN, C(=O)$OR^2$, C(=O)N($R^2)_2$, Si($R^2)_3$, N($R^2)_2$, $NO_2$, P(=O)($R^2)_2$, $OSO_2R^2$, $OR^2$, S(=O)$R^2$, S(=O)$_2R^2$, OH, SH, linear alkyl-, alkoxy- or thioalkyl-group with 1 to 20 C-atoms or a branched or cyclic alkyl-, alkoxy- or thioalkyl-group with 3 to 20 C-atoms or a alkenyl- or alkinyl-group with 2 to 20 C-atoms, wherein the group may be substituted with one or more of groups $R^2$ and wherein one or more $CH_2$-groups in the group may be replaced by —$R^2$C=$CR^2$—, —C≡C—, Si($R^2)_2$, C=O, C=S, C=$NR^2$, C(=O)O, C(=O)$NR^2$, $NR^2$, P(=O)($R^2$), O, S, SO or $SO_2$, and wherein one or more H-atoms in the group may be replaced by D, F, Cl, Br, I, CN or $NO_2$, or an aromatic or heteroaromatic ring system with 5 to 60 aromatic ring atoms, which can be substituted with one or more groups $R^2$, or an aryloxy- or heteroaryloxy-group with 5 to 60 aromatic ring atoms, which can be substituted with one or more groups $R^2$, or an aralkyl- or heteroaralkyl-group with 5 to 60 aromatic ring atoms, which can be substituted with one or more groups $R^2$, wherein two or more groups $R^2$ may be linked with each other and form an aliphatic or aromatic or heteroaromatic ring;
$R^2$ is at each occurrence independently selected from the group consisting of H, D, F, alkyl having from 1 to 20 C-atoms, aromatic groups having from 1 to 20 aromatic carbon atoms and heteroaromatic groups having from 1 to 20 aromatic ring atoms, wherein the aromatic groups and the heteroaromatic groups may be substituted with an alkyl having from 1 to 20 carbon atoms; and m is 0 or 1.

4. The compound according to claim 1, wherein at each occurrence $R^D$ is independently of each other selected from the group consisting of groups of formula (N-b)

 (N-b)

wherein $Ar^1$ is a substituted or unsubstituted aromatic with 6 to 30 aromatic ring atoms, or a heteroaromatic ring system with 5 to 30 aromatic ring atoms; and $NAr^2_2$ is selected from the group consisting of aromatic amines, heteroaromatic amines, carbazoles, azacarbazoles, annealed carbazoles, annealed azacarbazoles, 5,10-dihydro-phenazaboranes, 9,10-dihydroacridines, 9,10-dihydro-10-sila-acridines, 9,10-dihyddro-phenazine, 10-hydro-phenoxazine, and 10-hydro-phentiazine, all of which may be substituted or unsubstituted; and m is 0 or 1.

5. The compound according to claim 4, wherein in formula (N-b) the group $NAr^2_2$ is selected from the group consisting of aromatic amines, heteroaromatic amines, carbazoles, azacarbazoles, annealed carbazoles, annealed azacarbazoles, 5,10-dihydro-phenazaboranes, 9,10-dihydroacridines, 9,10-dihydro-10-sila-acridines, 9,10-dihydrophenazine, and 10-hydro-phenoxazine, and 10-hydro-phentiazine, all of which may be substituted or unsubstituted.

6. The compound according to claim 1, comprising at least two identical groups $R^D$.

7. The compound according to claim 1 comprising at least two identical $R^A$.

8. An oligomer, polymer or dendrimer comprising one or more of the compounds of claim 1, wherein at least one bond to the oligomer, polymer or dendrimer is on any one or more of groups $R^A$, $R^D$ or $R^S$.

9. A formulation comprising a solvent and the oligomer, polymer or dendrimer of claim 8.

10. A method of producing an electronic device, said method comprising the steps of
(a) an oligomer, polymer or dendrimer of claim 8; and
(b) depositing said oligomer, polymer or dendrimer on a supporting layer.

11. A formulation comprising a solvent and the compound of claim 1.

12. A method of producing an electronic device, said method comprising the steps of
(a) providing the compound of claim 1; and
(b) depositing said compound on a supporting layer.

13. An electronic device selected from the group consisting of organic integrated circuits (OICs), organic field-effect transistors (OFETs), organic thin-film transistors (OTFTs), organic light-emitting transistors (OLETs), organic photovoltaic cells, organic optical detectors, organic photoreceptors, organic field-quench-devices (OFQDs), organic light-emitting electrochemical cells (OLECs), organic laser diodes (O-Laser) and organic electroluminescence devices (OLEDs), characterized in that the electronic devices comprises the compound of claim 1.

14. An organic electroluminescent device, comprising an anode, a cathode and at least one organic layer, said organic layer comprising the compound of claim 1 as matrix material in an emitting layer in combination with one or more dopants, or that it is comprised as electron transport material in an electron transport layer, an electron injection layer or a hole blocking layer.

15. An organic electroluminescent device comprising an anode, a cathode and at least one organic layer, said organic layer comprising the compound of claim 1 as light emitting material.

* * * * *